(12) United States Patent
Cook et al.

(10) Patent No.: US 11,427,582 B2
(45) Date of Patent: Aug. 30, 2022

(54) LIGANDS SELECTIVE TO ALPHA 6 SUBUNIT-CONTAINING GABAA RECEPTORS AND THEIR METHODS OF USE

(71) Applicant: UWM Research Foundation, Inc., Milwaukee, WI (US)

(72) Inventors: James Cook, Milwaukee, WI (US); Daniel Knutson, Elkhorn, WI (US)

(73) Assignee: UWM Research Foundation, Inc., Milwaukee, WI (US)

( * ) Notice: Subject to any disclaimer, the term of this patent is extended or adjusted under 35 U.S.C. 154(b) by 0 days.

(21) Appl. No.: 17/078,739

(22) Filed: Oct. 23, 2020

(65) Prior Publication Data
US 2021/0047322 A1 Feb. 18, 2021

Related U.S. Application Data

(63) Continuation of application No. 15/578,790, filed as application No. PCT/US2016/035761 on Jun. 3, 2016, now Pat. No. 10,865,203.

(60) Provisional application No. 62/307,836, filed on Mar. 14, 2016, provisional application No. 62/170,552, filed on Jun. 3, 2015.

(51) Int. Cl.
| | | |
|---|---|---|
| *C07D 471/04* | (2006.01) | |
| *C07D 471/14* | (2006.01) | |
| *A61K 31/4745* | (2006.01) | |
| *C07D 498/14* | (2006.01) | |
| *C07D 495/14* | (2006.01) | |
| *C07D 491/147* | (2006.01) | |
| *A61P 25/18* | (2006.01) | |
| *A61P 25/24* | (2006.01) | |
| *A61P 27/16* | (2006.01) | |
| *A61P 25/06* | (2006.01) | |

(52) U.S. Cl.
CPC ........ *C07D 471/04* (2013.01); *A61K 31/4745* (2013.01); *A61P 25/06* (2018.01); *A61P 25/18* (2018.01); *A61P 25/24* (2018.01); *A61P 27/16* (2018.01); *C07D 471/14* (2013.01); *C07D 491/147* (2013.01); *C07D 495/14* (2013.01); *C07D 498/14* (2013.01)

(58) Field of Classification Search
CPC .. C07D 471/04; C07D 471/14; C07D 498/14; C07D 495/14; A61K 31/4745; A61P 25/18; A61P 25/24; A61P 25/06
USPC ....................................................... 514/293
See application file for complete search history.

(56) References Cited

U.S. PATENT DOCUMENTS

| 4,312,870 A | 1/1982 | Yokoyama |
| 4,459,298 A | 7/1984 | Bernard |
| 8,895,580 B2 * | 11/2014 | Beshore ............... C07D 401/14 |
| | | 514/293 |
| 9,249,149 B2 | 2/2016 | Silverman et al. |
| 10,865,203 B2 | 12/2020 | Cook et al. |
| 2003/0045532 A1 | 3/2003 | Chambers et al. |
| 2006/0258643 A1 | 11/2006 | Cook et al. |

FOREIGN PATENT DOCUMENTS

| WO | 199906399 A1 | 2/1999 |
| WO | 199906401 A1 | 2/1999 |

OTHER PUBLICATIONS

Varagic et al., British Journal of Pharmacology (2013), 169(2), 371-383.*
Briens et al., "Optimalization of pharmacokinetics—an essential aspect of drug development—by "metabolic stabilization,"" Strategy in Drug Research, Pharmaco Chemistry Library 4, edited by J.A. Keverling Buisman, 1982, 165-178.
Braff D, Stone C, Callaway E, Geyer M, Glick I, Bali L., "Prestimulus effects on human startle reflex in normals and schizophrenics," Psychophysiology. 15(4):339-43 (1978).
Castellanos FX, Fine EJ, Kaysen D, Marsh WL, Rapoport JL, Hallett M., "Sensorimotor gating in boys with Tourette's syndrome and ADHD: preliminary results," Biol Psychiatry. 39(1):33-41 (1996).
Di et al., "Optimization of a Higher Throughput Microsomal Stability Screening Assay for Profiling Drug Discovery Candidates," Journal of Biomolecular Screening, 2003, 8(4):453-462.
Dworkin S.F., K.H. Huggins, L. LeResche, M. Von Korff, J. Howard, E. Truelove, E. Sommers, "Epidemiology of signs and symptoms in temporomandibular disorders: clinical signs in cases and controls," J Am Dent Assoc 120:273-281 (1990).
European Patent Office Extended Search Report for Application No. 16804541.7 dated Mar. 1, 2019 (10 pages).
Fan PC, Huang WJ, Chiou LC., "Intractable chronic motor tics dramatically respond to *Clerodendrum inerme* (L) Gaertn," J Child Neurol. 24(7):887-90 (2009).
Fan PC, Kuo PH, Hu JW, Chang SH, Hsieh ST and Chiou LC, "Different trigeminovascular responsiveness between adolescent and adult rats in a migraine model," Cephalalgia 32:979-90 (2012).
Fisher, M. B. et al., "The complexities inherent in attempts to decrease drug clearance by blocking site of GYP-mediated metabolism," Curr. Op. Drug Disc & Develop. 2006, 9(1), 101-109.
Foster, "Deuterium Isotope Effects in the Metabolism of Drugs and Xenobiotics: Implications for Drug Design," Advances in Drug Research, 1985, 14, 1-40.

(Continued)

*Primary Examiner* — Niloofar Rahmani
(74) *Attorney, Agent, or Firm* — Michael Best & Friedrich LLP

(57) ABSTRACT

Provided herein are novel pyrazoloquinolinone compounds and method of using such compounds to treat disorders such as neuropsychiatric disorders with sensorimotor gating deficits, such as schizophrenia, tic disorders, attention deficit hyperactivity disorder, obsessive compulsive disorder, panic disorder, Huntington's disease and nocturnal enuresis; depression; temporomandibular myofascial pain; disorders of trigeminal nerve, such as trigeminal neuralgia and trigeminal neuropathy; migraine; and tinnitus.

2 Claims, 36 Drawing Sheets

(56) References Cited

OTHER PUBLICATIONS

Fryer et al., "Structure Activity Relationship studies at the Benzodiazepine Receptor (BZR): A Comparison of the Substituent Effects of Pyrazoloquinolinone Analogs," J. Med. Chem., 1993, 36, 1669-1673.
Fukuto, "Determination of the Mechanism of Demethylenation of (Methylenedioxy)phenyl Compounds by Cytochrome P450 Using Deuterium Isotope Effects," Journal of Medical Chemistry, 1991, 34, 2871-2876.
Geyer MA and Moghaddam, "Animal models relevant to schizophrenia disorders. Neuropsychopharmacology: The fifth generation of progress," (Davids KL, Charney D, Coyle JT and Nemeroff C eds) pp. 689-701, American College of Neuropsychopharmacology (2002).
Gutierrez A, Khan ZU, De Blas AL., "Immunocytochemical localization of the α6 subunit of the γ-aminobutyric acid receptor in the rat nervous system," J Comp Neurol. 365: 504-510 (1996).
Harbeson et al., "Deuterium in Drug Discovery and Development," Annual Reports in Medicinal Chemistry, 2011, vol. 46, Chapter 12, 403-417.
He X, Huang Q, Yu S, Ma C, McKernan R, Cook JM, "Studies of molecular pharmacophore/receptor models for GABAA/BzR subtypes: binding affinities of symmetrically substituted pyrazolo[4,3-c]quinolin-3-ones at recombinant alpha x beta 3 gamma 2 subtypes and quantitative structure-activity relationship studies via a comparative molecular field analysis," Drug Des Discov. 16(1): 77-91 (1999).
Hoenig K, Hochrein A, Quednow BB, Maier W, Wagner M., "Impaired prepulse inhibition of acoustic startle in obsessive-compulsive disorder," Biol Psychiatry, 57(10):11538 (2005).
Knutson, et al., "Design and Synthesis of Novel Deuterated Ligands Functionally Selective for the g-Aminobutyric Acid Type A Receptor (GABAAR) a6 Subtype with Improved Metabolic Stability and Enhanced Bioavailability," J. Med. Chem. 2018, 61, 2422-2446.
Kumari V, Gray JA, Geyer MA, ffytche D, Soni W, Mitterschiffthaler MT, Vythelingum GN, Simmons A, Williams SC, Sharma T.,"Neural correlates of tactile prepulse inhibition: a functional MRI study in normal and schizophrenic subjects," Psychiatry Res. 122(2):99-113 (2003).
Liu et al., "CTP-354: A novel deuterated subtype-selective GABA(A) modulator for treatment of neuropathic pain, spasticity and anxiety disorders," CoNCERT Pharmaceuticals, 2012.
Masimirembwa et al., "Metabolic Stability for Drug Discovery and Development: Pharmacokinetic and Biochemical Challenges," Clin Pharmacokinet., 2003, 42(6):515-528.
Mirheydar P, Ramerstorfer J, Varagic Z, Scholze P, Wimmer L, Mihovilovic MM, Sieghart W, Ernst M., "Unexpected Properties of δ-Containing GABAA Receptors in Response to Ligands Interacting with the α+ β− Site," Neurochem Res., 2014, 39:1057-1067.
Mittleman G, Goldowitz D, Heck DH, Blaha CD., "Cerebellar modulation of frontal cortex dopamine efflux in mice: relevance to autism and schizophrenia," Synapse. 62(7):544-50. (2008).
Miwa, G. T. and Lu, A. Y. H., "Kinetic Isotope Effects and 'Metabolic Switching' in Cytochrome P450-Catalyzed Reactions," BioEssays 1987, 7(5), 215-19.
Nassar et al., "Improving the decision-making process in the structural modification of drug candidates: enhancing metabolic stability," Drug Discov Today, 2004, 9(23): 1020-1028.
Nelson, et al., "The use of Deuterium Isotope Effects to Probe the Active Site Properties, Mechanism of Cytochrome P450-Catalyzed Reactions, and Mechanisms of Metabolically Dependent Toxicity," Drug Metabolism and Disposition, 2003, 31(12), 1481-1498.
Olsen RW, Sieghart W, "International Union of Pharmacology. LXX. Subtypes of gamma-aminobutyric acid(A) receptors: classification on the basis of subunit composition, pharmacology, and function," Update. Pharmacol Rev. 60:243-260 (2008).
Ornitz EM, Hanna GL, de Traversay. "Prestimulation-induced startle modulation in attention-deficit hyperactivity disorder and nocturnal enuresis," J Psychophysiology. 29(4):437-51 (1992).
International Search Report and Written Opinion for Application No. PCT/US2016/035761 dated Oct. 27, 2016 (12 pages).
Petryshen TL, Middleton FA, Tahl AR, Rockwell GN, Purcell S, Aldinger KA, Kirby A, Morley CP, McGann L, Gentile KL, Waggoner SG, Medeiros HM, Carvalho C, Macedo A, Albus M, Maier W, Trixler M, Eichhammer P, Schwab SG, Wildenauer DB, Azevedo MH, Pato MT, Pato CN, Daly MJ, Sklar P., "Genetic investigation of chromosome 5q GABAA receptor subunit genes in schizophrenia," Mol Psychiatry. 10(12):1074-88, (2005).
Pirker S, Schwarzer C, Wieselthaler A, Sieghart W, Sperk G., "GABAA receptors: immunocytochemical distribution of 13 subunits in the adult rat brain," Neurosci. 101(4): 815-850 (2000).
Plesh O., S.H. Adams, S.A. Gansky, "Racial/ethnic and gender prevalences in reported common pains in a national sample," J Orofac Pain 25:25-31 (2011).
Puri J, Vinothini P, Reuben J, Bellinger LL, Ailing L, Peng YB, Kramer PR., "Reduced GABA(A) receptor α6 expression in the trigeminal ganglion alters inflammatory TMJ hypersensitivity," Neuroscience. 213:179-90 (2012).
Ramerstorfer J, Furtmuller R, Sarto-Jackson I, Varagic Z, Sieghart W, Ernst M,"The GABAA receptor alpha+beta-interface: a novel target for subtype selective drugs," J Neurosci. 31:870-877 (2011).
Savini et al. "Pyrazolo [4,3-c] quinolines synthesis and specific inhibition of benzodiazepine receptor binding (Note I)," 1993, IL Farmaco, 48(1):65-76.
Savini et al., "High affinity central benzodiazepine receptor ligands. Part 2: quantitative structure-activity relationships and comparative molecular field analysis of pyrazolo[4,3-c]quinolin-3-ones," Bioorganic & Medicinal Chemistry, 2001, vol. 9, pp. 431-444.
Savini et al., "High Affinity Central Benzodiazepine Receptor Ligands: Synthesis and Structure-Activity Relationship Studies of a New Series of Pyrazolo[4,3-c]quinolin-3-ones," Bioorganic & Medicinal Chemistry, 1998, vol. 6, pp. 389-399.
Shigenaga Y, Sera M, Nishimori T, Suemune S, Nishimura M, Yoshida A, Tsuru K.,"The central projection of masticatory afferent fibers to the trigeminal sensory nuclear complex and upper cervical spinal cord," J Comp Neurol., 268(4):489-507 (1988).
Singer HS., "Tourette's syndrome: from behaviour to biology." Lancet Neurol., 2005, 4(3):149-59.
Swerdlow NR, Geyer MA, Braff DL. "Neural circuit regulation of prepulse inhibition of startle in the rat: current knowledge and future challenges," Psychopharmacology, 2001, 156(2-3):194-215.
Swerdlow NR, Karban B, Ploum Y, Sharp R, Geyer MA, Eastvoid A., "Tactile prepuff inhibition of startle in children with Tourette's syndrome: in search of an "fMRIfriendly" startle paradigm," Biol Psychiatry. 50(8):578-85 (2001).
TAM," Individual Variation in First-Pass Metabolism," Clin Pharmacokinet., 1993, 25(4):300-328.
Thompson, "Optimization of Metabolic Stability as a Goal of Modern Drug Design," Medicinal Research Reviews, 2001, 21(5):412-449.
Varagic et al., "Subtype selectivity of α+β− site ligands of GABAA receptors: identification of the first highly specific positive modulators at α6β2/3γ2 receptors," British Journal of Pharmacology, 2013, vol. 169, pp. 384-399.
Varagic Z, Wimmer L, Schnuerch M, Mihovilovic MD, Huang S, Rallapalli S. et al. "Identification of novel positive allosteric modulators and null modulators at the GABAA receptor α+β− interface," Br J Pharmacol. 169(2): 371-383 (2013).
Wiberg, "The Deuterium Isotope Effect," Department of Chemistry, University of Washington, Seattle, Washington, Apr. 6, 1955, 713-743.
Zhang et al., "Synthesis of novel imidazobenzodiazepines as probes of the pharmacophore for "diazepam-insensitive" GABAa receptors," 1995, Journal of Medicinal Chemistry, American Chemical Society, 38(10):1679-1688.
Wermuth, "Molecular Variations Based on Isosteric Replacements," The Practice of Medicinal Chemistry, 1996, Chapter 13, 203-237.

\* cited by examiner

| Compound | R8 | R7 | R6 | X9 | X8 | X7 | X6 | R4' | R3' | R2' | X3' |
|---|---|---|---|---|---|---|---|---|---|---|---|
| Comp 6 | H | OCH3 | H | C | C | C | C | OCH3 | H | H | C |
| DK-I-56-1 | H | OCH3 | H | C | C | C | C | OCD3 | H | H | C |
| RV-I-029 | H | OCD3 | H | C | C | C | C | OCH3 | H | H | C |
| DK-I-60-3 | H | OCD3 | H | C | C | C | C | OCD3 | H | H | C |
| DK-I-94-1 | H | OCD3 | H | C | C | C | C | H | OCD3 | H | C |
| DK-I-88-1 | H | OCH3 | H | C | C | C | C | H | H | OCD3 | C |
| DK-I-90-1 | H | OCD3 | H | C | C | C | C | H | H | OCD3 | C |
| CW-03-030 | H | OCH3 | H | C | N | C | C | OCH3 | H | H | C |
| DK-II-13-1 | H | OCH3 | H | C | C | C | C | OCH3 | H | H | N |
| DK-I-86-1 | H | OCD3 | H | C | C | C | C | OCH3 | H | H | N |
| DK-II-60-1 | H | OCH3 | H | C | C | C | C | OCD3 | H | H | N |
| RV-I-37 | H | OCD3 | H | C | C | C | C | H | H | H | C |
| CW-02-073 | H | OCH3 | CH3 | C | C | C | C | OCH3 | H | H | C |

FIG. 23

| Name | | | | | | | | | | |
|------|---|---|---|---|---|---|---|---|---|---|
| CW-02-078 | H | OCH3 | OCH3 | C | C | C | H | H | H | C |
| CW-02-079 | H | OCH3 | CH3 | C | C | C | OCF3 | H | H | C |
| CW-02-082 | H | OCH3 | CH3 | C | C | C | OCF3 | H | H | C |
| MM-I-03 | Br | H | H | C | C | C | OCH3 | H | H | C |
| MM-I-13 | Br | H | F | C | C | C | Cl | H | H | C |
| MM-I-18 | Br | H | F | C | C | C | F | H | H | C |
| Comp 11 | Cl | H | F | C | C | C | OCH3 | H | H | C |
| DK-I-93-1 | Cl | H | H | C | C | C | OCD3 | H | H | C |
| LAU 159 | Cl | H | H | C | C | C | H | OCH3 | H | C |
| DK-I-59-1 | Cl | H | H | C | C | C | H | OCD3 | H | C |
| LAU 165 | Cl | H | H | C | C | C | H | H | OCH3 | C |
| DK-I-87-1 | Cl | H | H | C | C | C | H | H | OCD3 | N |
| DK-II-18-1 | Cl | H | H | C | N | C | OCH3 | H | H | N |
| DK-II-59-1 | H | Cl | H | C | C | C | OCD3 | H | H | C |
| CW-03-033 | H | Br | H | C | C | C | OCD3 | H | H | C |
| LAU 463 | H | Br | H | C | C | C | OCD3 | H | H | C |
| DK-I-58-1 | H | Br | H | C | C | C | H | OCD3 | OCH3 | C |
| DK-I-92-1 | H | Br | H | C | C | C | H | H | H | C |
| DK-I-89-1 | H | Br | H | C | C | C | OCH3 | H | OCD3 | C |
| DK-II-48-1 | H | Br | H | C | C | C | OCH3 | H | H | N |

FIG. 23 (cont'd)

| | | | | | | | | | | |
|---|---|---|---|---|---|---|---|---|---|---|
| DK-II-58-1 | H | Br | H | C | C | C | OCD3 | H | H | N |
| LAU 176 | OCH3 | H | H | C | C | C | OCH3 | H | H | C |
| DK-I-95-3 | OCD3 | H | H | C | C | C | OCD3 | H | H | C |
| DK-I-97-1 | OCD3 | H | H | C | C | C | H | OCD3 | H | C |
| DK-98-1 | OCD3 | H | H | C | C | C | H | H | OCD3 | C |
| RV-I-071 | H | H | H | C | N | C | OCH3 | H | H | H |
| MM-I-06 | H | CF3 | H | C | C | C | OCH3 | H | H | C |
| MM-I-08 | H | CF3 | H | C | C | C | Cl | H | H | C |
| MM-I-09 | H | CF3 | H | C | C | C | NO2 | H | H | C |
| MM-I-10 | H | CF3 | H | C | C | C | OCF3 | H | H | C |
| MM-I-11 | H | CF3 | H | C | C | C | F | H | H | C |
| MM-I-12 | H | CF3 | H | C | C | C | H | OCH3 | H | C |

FIG. 23 (cont'd)

| Compound | [μM] | αxβ3γ2 | | | | | | |
|---|---|---|---|---|---|---|---|---|
| | | α6β3γ2 | α1β3γ2 | α2β3γ2 | α3β3γ2 | α4β3γ2 | α5β3γ2 | α1β1γ2 |
| Compound 6 | 0.1 | 154.27±14.31 | 106.33±3.48 | | | 113.67±5.67 | | |
| | 1 | 317.18±16.78 | 115.23±7.41 | 99.57±4.64 | 105.75±5.53 | 133.22±7.73 | 111.07±9.74 | 116.43±9.61 |
| | 10 | 671.73±49.67 | 193.25±23.94 | 159.76±7.61 | 176.46±12.69 | 218.7±14.78 | 217.77±9.99 | 191.83±21.47 |
| DK-I-56-1 | 0.1 | 107.9±11.5 | | | | | | |
| | 1 | 260.68±20.2 | 110.5±5.15 | 104.97±15.62 | 133.5±10.64 | 86.55±8.05 | 104.55±4.55 | 118.5±18.37 |
| | 10 | 503.76±55.71 | 161.56±10.29 | 178.4±15.9 | 140.83±15.2 | 138.35±9.15 | 105.2±0.5 | 150.77±20.42 |
| RV-I-029 | 0.1 | 184.28±17.8 | | | | | 115.95±2.05 | |
| | 1 | 339.62±28.79 | | | | | 199.9±2.9 | |
| | 10 | | | | | | | |
| DK-I-60-3 | 0.1 | 289.03±29.68 | 128.84±10.12 | 110.27±9.47 | 118.63±6.29 | 112.75±3.25 | 148.6±11.69 | 153.1±5.1 |
| | 1 | 632.96±78.53 | 221.4±10.01 | 197.87±13.57 | 197.73±0.58 | 198.55±8.05 | 320.28±40.14 | 230.65±5.15 |
| | 10 | | | | | | | |
| DK-I-86-1 | 0.1 | 109.36±4.94 | | | | | 80.13±11.27 | 108.8±3.1 |
| | 1 | 160.68±8.86 | 100.96±3.89 | 87.77±2.48 | 93.77±2.83 | 104.45±1.75 | 79.73±11.39 | 126.8±2.3 |
| | 10 | 253.63±12.31 | 100.58±2.54 | 87.27±2.47 | 96.77±2.86 | 118.3±7.3 | | |
| CW-03-030a | 0.1 | 123.5±4.38 | | | | | 106.2±6.2 | |
| | 1 | 214.25±12.85 | | | | | 125.35±2.45 | |
| | 10 | | | | | | | |
| LAU463 | 0.1 | 182.4±20.04 | 98.35±3.75 | 103.1±2 | 124.27±12.33 | 112.95±0.35 | 110.8±0 | |
| | 1 | 311.68±24.36 | 161.25±27.88 | 149.7±17.25 | 199±40.72 | 134.48±14.49 | 133.78±7.74 | |
| | 10 | 706.91±50.88 | 238.33±58.04 | 276.86±60.66 | | 231.25±18.52 | 223.48±29.39 | |
| DK-I-58-1 | 0.1 | 187.88±22.68 | 134.8±6.83 | 107.43±3.76 | 113.05±4.75 | 109.65±3.75 | 117.17±2.17 | |
| | 1 | 529.53±93.9 | 321.73±34.02 | 196.72±37.4 | 187.7±1.8 | 189.2±3.6 | 205.37±32.53 | |
| | 10 | | | | | | | |
| LAU159 | 0.1 | 130.33±9.27 | 100.13±0.13 | 96.3±3.7 | 101±1 | 98.9±1.1 | 96.4±3 | |
| | 1 | 184.01±16.12 | 114.97±12.6 | 89.3±0.2 | 102±9 | 101.55±4.75 | 90.67±3.53 | |
| | 10 | 275.08±23.48 | 111.5±4.74 | 103.6±1 | 103.5±10.5 | 103.3±1.2 | 81.71±6.4 | |
| DK-I-59-1 | 0.1 | 114.6±4.6 | 100±9.4 | | | | | |
| | 1 | 132.6±7.58 | | | | | | |
| | 10 | 204.83±16.55 | | | | | | |
| LAU165 | 0.1 | 103.45±17.31 | | | 106.65±11.05 | 85.1±1.3 | | |
| | 1 | 103.43±13.73 | | | 95.05±7.45 | | | |
| DK-I-87-1 | 0.1 | 106.66±4.88 | 99.5±0 | 119.37±18.65 | | | | |
| | 1 | 102.16±4.41 | 47.2±0 | 89.57±18.33 | | | | |

FIG. 24

| Compound | [µM] | α6β1γ2 | α6β3δ | α1β1 | α1β3 | αxβy α2β3 | α3β3 | α5β3 |
|---|---|---|---|---|---|---|---|---|
| Compound 6 | 0.1 | 126.3±1.3 | 120.4±4.2 | 150.92±20.42 | 120.76±8.33 | 116.93±20.71 | 133.93±20.93 | 104.22±12.78 |
|  | 1 | 173.53±14.87 | 192.05±22.83 | 167.88±9.73 | 190.28±11.48 | 139±25.44 | 226.03±14.12 | 246.02±19.57 |
|  | 10 | 191.95±19.02 | 239.94±25.93 | 296.98±23.53 |  |  |  |  |
| DK-I-56-1 | 0.1 | 105.15±1.75 | 210±50.79 | 112.77±4.14 | 116.3±25 | 124.5±18.53 |  |  |
|  | 1 | 132.88±6.86 | 386.35±151.75 | 144.63±9.25 | 144.3±24.3 | 164.27±65.66 |  |  |
|  | 10 | 159.23±11.62 |  | 231.57±12.05 |  |  |  |  |
| RV-I-029 | 0.1 |  |  |  | 137.2±17.7 |  |  |  |
|  | 1 |  |  |  | 191.8±69.4 |  |  |  |
|  | 10 |  |  |  |  |  |  |  |
| DK-I-60-3 | 0.1 | 129±4.6 | 178.8±44.58 | 110.25±3.21 | 175.5±59.5 | 160.7±32.49 |  |  |
|  | 1 | 170.35±8.15 | 350.3±127.57 | 185.8±14.3 | 184±66.5 | 198.27±35.15 |  |  |
|  | 10 |  |  | 318.23±8.23 |  |  |  |  |
| DK-I-86-1 | 0.1 | 97.9±1.1 | 102.65±1.65 | 118.38±8.4 | 122.95±2.95 | 92.3±11.76 | 90.5±7.2 |  |
|  | 1 | 99.58±6.25 | 140.1±25.1 | 118.63±1.54 | 114.05±0.45 | 54.37±20.75 | 88.05±3.65 |  |
|  | 10 | 121.88±6.2 |  | 168.17±14.34 |  |  |  |  |
| CW-03-030a | 0.1 |  |  |  |  |  |  |  |
|  | 1 |  |  |  |  |  |  |  |
|  | 10 |  |  |  |  |  |  |  |
| LAU463 | 0.1 | 125.25±14.15 | 131.15±18.85 | 107.6±1.7 |  | 95.18±1.43 |  |  |
|  | 1 | 132.8±12.37 | 202.38±28.54 | 127.65±1.15 |  | 113.6±10.5 |  |  |
|  | 10 | 172.9±7.18 |  | 302.8±17.5 |  |  |  |  |
| DK-I-58-1 | 0.1 | 101.7±1.7 | 114.25±15.75 | 87.5±20.8 | 173.07±31.62 | 104.6±11.5 |  |  |
|  | 1 | 109.28±3.54 | 232.75±112.25 | 144.5±25.5 | 177.17±39.76 | 124.65±10.85 |  |  |
|  | 10 | 147.39±10.62 |  | 296.85±20.65 |  |  |  |  |
| LAU159 | 0.1 | 121.25±25.33 | 109.9±1.9 | 119.2±10.65 | 101.18±5.49 |  |  |  |
|  | 1 | 119.5±19.5 | 121.75±15.52 | 176.98±24.01 | 105.37±4.82 |  |  |  |
|  | 10 | 112.68±17.63 | 142.58±23.6 | 260.68±43.71 | 117.4±10.52 |  |  |  |
| DK-I-59-1 | 0.1 | 92.86±5.09 | 103.75±15.25 | 131.88±9.66 | 101±1 |  |  |  |
|  | 1 | 101.12±6.83 | 113.35±5.65 | 188.95±30.96 | 112.85±5.15 |  |  |  |
|  | 10 | 91.78±10.95 |  | 315.58±37.32 |  |  |  |  |
| LAU165 | 0.1 | 117.65±7.35 |  |  |  | 93.4±2.9 |  |  |
|  | 1 | 113.95±12.74 |  |  |  | 104.5±14 |  |  |
|  | 10 | 126.18±18.5 |  |  |  |  |  |  |
| DK-I-87-1 | 0.1 | 110.5±9.1 |  |  | 87.25±12.75 |  |  |  |
|  | 1 | 103.9±0.3 |  |  | 90.85±12.35 |  |  |  |

FIG. 24 (cont'd)

Example Synthetic Route of Deuterated Analog DK-II-60-1

LIGANDS SELECTIVE TO ALPHA 6 SUBUNIT-CONTAINING GABAA RECEPTORS AND THEIR METHODS OF USE

CROSS-REFERENCE TO RELATED APPLICATIONS

This patent application is a continuation of U.S. patent application Ser. No. 15/578,790, filed on Dec. 1, 2017, which is the U.S. national stage entry, under 35 U.S.C. § 371, of International Application Number PCT/US2016/035761, filed Jun. 3, 2016, which claims priority to United States Provisional Patent Application Nos. 62/170,552, filed on Jun. 3, 2015, and 62/307,836, filed on Mar. 14, 2016, the entire contents of each of which are hereby incorporated by reference.

STATEMENT REGARDING FEDERALLY SPONSORED RESEARCH OR DEVELOPMENT

This invention was made with United States government support under NIH grant number 1 R01 MH09463-01A1. The United States government has certain rights to this invention.

This invention was made with Taiwan government support from the Minister of Science and Technology under grant number MOST 104-2923-B002-006-MY3 and MOST 105-2325-B002-004.

BACKGROUND

Gamma-aminobutyric acid (GABA) is the major inhibitory neurotransmitter in the central nervous system. GABA is released from GABAergic synapses and mediates its effect by interacting with GABA receptors. GABA receptors can be divided into two main classes: (1) $GABA_A$ receptors, which are members of the ligand-gated ion channel superfamily; and (2) $GABA_B$ receptors, which are members of the G-protein linked receptor superfamily.

$GABA_A$ receptors are composed of five subunits that form a central chloride channel. Binding of GABA to these receptors opens the chloride channel and usually causes an influx of chloride ions into the neurons and thus, an inhibition of their electrical activity. $GABA_A$ receptors, thus, predominantly function to inhibit and regulate neuronal activity, and fulfill other roles in non-neuronal cells. In the mammalian genome a total of 19 subunits (6α, 3β, 3γ, δ, ε, π, θ, 3ρ) belonging to 8 different subunit classes have been identified. The majority of the receptors are composed of two α, two β, and one γ subunit. Receptors composed of two α6, two β3, and one γ2 subunit are named α6β3γ2 receptors. $GABA_A$ receptors can also be composed of up to five different subunits. In this case, all subunits present in the receptor have to be mentioned to define the receptor subtype. Depending on the regional, cellular, and subcellular distribution of the individual subunits in the brain, a large variety of $GABA_A$ receptor subtypes with distinct subunit composition and unique pharmacology can be formed. Due to their specific localization in the nervous system each receptor subtype has a specific function and can more or less strongly influence the neuronal circuits on which the receptors are located and thus, modulate behavior elicited by these neuronal circuits (Olsen and Sieghart, Pharmacol Rev. 2008).

$GABA_A$ receptors are the site of action of a variety of pharmacologically and clinically important drugs, such as the benzodiazepines, barbiturates, neuroactive steroids, anesthetics, and also some convulsants. These drugs interact with a multitude of allosteric binding sites at $GABA_A$ receptors, many of which so far have not been identified, and by that, enhance or reduce GABA-induced chloride flux. For benzodiazepines, the binding sites are known to be at α+/γ- extracellular interfaces of α1,2,3,5, and γ2 containing receptors. The modulatory binding sites for pyrazoloquinolinones are at the extracellular α+/β- interfaces of all $GABA_A$ receptor subtypes that contain such interfaces (see FIG. 1).

Whereas benzodiazepines and pyrazoloquinolinones can only allosterically modulate GABA-induced chloride flux, other compounds such as barbiturates, neuroactive steroids and anesthetics exhibit a biphasic effect. At low concentrations, they allosterically modulate GABA-induced chloride currents, at higher concentrations they also can directly open the $GABA_A$ receptor-associated chloride channel in the absence of GABA. These latter compounds are thus much more toxic than the benzodiazepines or pyrazoloquinolinones that only can modulate ongoing GABAergic activity.

SUMMARY

In an aspect the invention provides a compound according to Formula I:

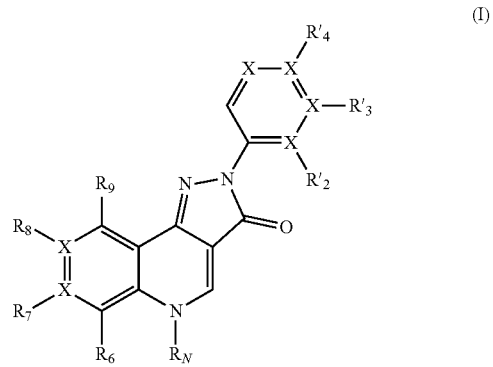

wherein
each X is independently C or N;
$R'_2$, $R'_3$ and $R'_4$ are independently selected from H, $C_{1-4}$ alkyl, $C_{1-4}$ alkoxy, halogen, $NR_{10}R_{11}$, $NO_2$, hydroxyl, cyano, $C_{1-4}$ alkylthio, $-C(O)C_{1-4}$ alkyl, or $-C(O)NR_{10}R_{11}$;
$R_6$, $R_7$, $R_8$ and $R_9$ are independently selected from H, $C_{1-4}$ alkyl, $C_{1-4}$ alkoxy, halogen, $NR_{10}R_{11}$, $NO_2$, hydroxyl, cyano, $C_{1-4}$ alkylthio, $-C(O)C_{1-4}$ alkyl, or $-C(O)NR_{10}R_{11}$, or $R_6$ and $R_7$ or $R_7$ and $R_8$ can form a 4-6 member ring;
$R_{10}$ and $R_{11}$ are independently selected from H and $C_{1-4}$ alkyl; and
$R_N$ is H or $C_{1-4}$ alkyl;

In an aspect the present invention provides a compound according to Formula (II):

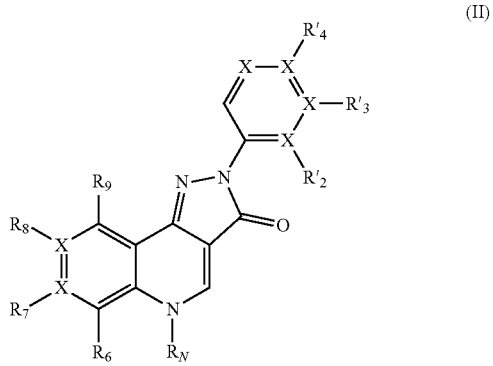

wherein
each X is independently C or N;
R'$_2$, R'$_3$ and R'$_4$ are independently selected from H, C$_{1-4}$ alkyl, C$_{1-4}$ alkoxy, halogen, NR$_{10}$R$_{11}$, NO$_2$, hydroxyl, cyano, C$_{1-4}$ alkylthio, —C(O)C$_{1-4}$ alkyl, or —C(O)NR$_{10}$R$_{11}$;
R$_6$, R$_7$, R$_8$ and R$_9$ are independently selected from H, C$_{1-4}$ alkyl, C$_{1-4}$ alkoxy, and halogen; NR$_{10}$R$_{11}$, NO$_2$, hydroxyl, cyano, C$_{1-4}$ alkylthio, —C(O)C$_{1-4}$ alkyl, or —C(O)NR$_{10}$R$_{11}$; or R$_6$ and R$_7$ or R$_7$ and R$_8$ can form a 4-6 member ring;
R$_{10}$ and R$_{11}$ are independently selected from H and C$_{1-4}$ alkyl; and
R$_N$ is H or C$_{1-4}$ alkyl;
wherein at least one of R'$_2$, R'$_3$, R'$_4$, R$_6$, R$_7$, R$_8$, R$_9$, R$_{10}$, R$_{11}$ and R$_N$ contains at least one deuterium.

In an aspect the invention provides a pharmaceutical composition comprising the compounds described herein and a pharmaceutically acceptable carrier.

In an aspect the invention provides a method of treating diseases and/or conditions which are regulated by the α6-GABA$_A$ receptor comprising administering a therapeutically effective amount of a compound described herein to a subject in need thereof.

In an aspect the invention provides a method of treating a disease and/or condition comprising administering a therapeutically effective amount of a compound described herein to a subject in need thereof; wherein the disease is modulated by the α6-subunit GABA$_A$ receptor.

Other aspects of the invention will become apparent by consideration of the detailed description and accompanying drawings.

BRIEF DESCRIPTION OF THE DRAWINGS

FIG. 23 shows compounds according to the present invention.

FIG. 24. Efficacy (% of modulation of control GABA EC3 current=100%) of test compounds at different recombinant rat αxβx, αxβ3γ2 and αβδ receptors expressed in Xenopus laevis oocytes. Values are reported as mean±SEM.

DETAILED DESCRIPTION

Figure 1:
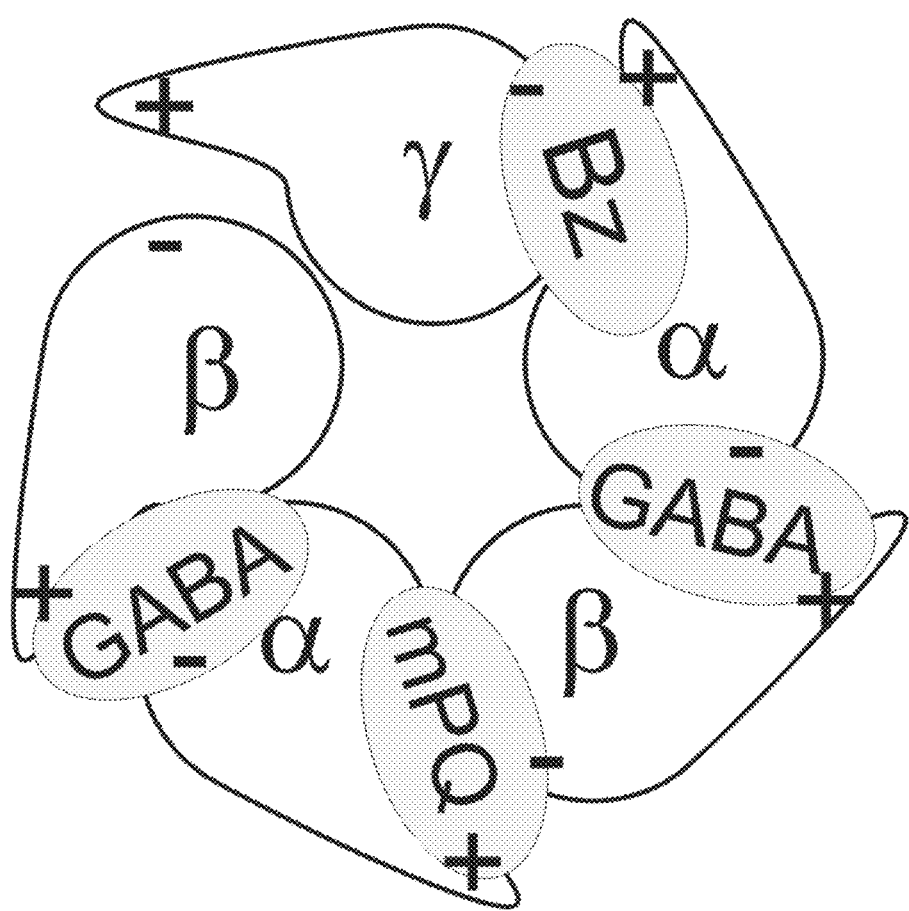
FIG. 1. The scheme represents an extracellular domain of a receptor with the most common two α, two β, and one γ composition and arrangement. Plus and minus signs indicate the subunits' principal, or plus- and complementary, or minus-sites. The two binding sites labelled with (GABA) are the GABA binding sites, (Bz) denotes the high affinity benzodiazepine binding site, and (mPQ) is the "modulatory prazoloquinolinone" binding site at the α+/β− interface.

In embodiments this disclosure provides novel pyrazoloquinolinone compounds. In embodiments this disclosure provides pyrazoloquinolinone compounds with selective modulatory activity at $GABA_A$ α6β3γ2 receptors. In embodiments, this invention provides pyrazoloquinolinone compounds with selective modulatory activity at $GABA_A$ α6β1γ2 receptors. In embodiment, this invention provides pyrazoloquinolinone compounds with selective modulatory activity at $GABA_A$ α6βδ receptors. In embodiments the invention provides pyrazoloquinolinone compounds with selective modulatory activity at more than one $GABA_A$ receptor selected from α6β3γ2, α6β1γ2, and α6βδ.

In embodiments this disclosure describes a method of treating a disorder with a pyrazoloquinolinone compound including, but not limited to, neuropsychiatric disorders with sensorimotor gating deficits, such as schizophrenia, tic disorders, attention deficit hyperactivity disorder, obsessive compulsive disorder, panic disorder, Huntington's disease and nocturnal enuresis; depression; temporomandibular myofascial pain; disorders of trigeminal nerve, such as trigeminal neuralgia and trigeminal neuropathy; migraine; and tinnitus.

In embodiments this disclosure describes a method of treating neuropsychiatric disorders with sensorimotor gating deficits, such as schizophrenia, tic disorders, attention deficit hyperactivity disorder, obsessive compulsive disorder, panic disorder, Huntington's disease and nocturnal enuresis; depression; temporomandibular myofascial pain; disorders of trigeminal nerve, such as trigeminal neuralgia and trigeminal neuropathy; migraine; and tinnitus with a compound with a selective positive allosteric modulation at α6 subunit-containing $GABA_A$ receptors.

In embodiments the present invention provides compounds with the following structure:

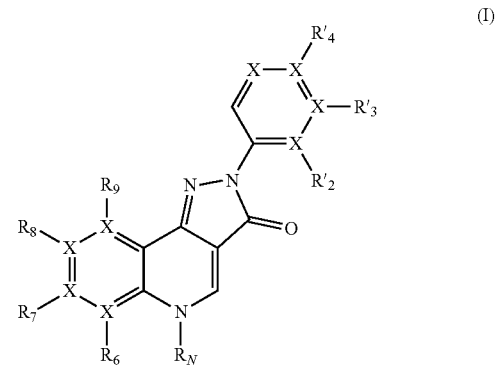

(I)

wherein
$R'_2$, $R'_3$ and $R'_4$ are independently selected from H, $C_{1-4}$ alkyl, $C_{1-4}$ alkoxy, halogen, $NR_{10}R_{11}$, $NO_2$, hydroxyl, cyano, $C_{1-4}$ alkylthio, —C(O)$C_{1-4}$ alkyl, or —C(O)$NR_{10}R_{11}$;

$R_6$, $R_7$, $R_8$ and $R_9$ are independently selected from H, $C_{1-4}$ alkyl, $C_{1-4}$ alkoxy, halogen, $NR_{10}R_{11}$, $NO_2$, hydroxyl, cyano, $C_{1-4}$ alkylthio, —C(O)$C_{1-4}$ alkyl, or —C(O)$NR_{10}R_{11}$, or $R_6$ and $R_7$ or $R_7$ and $R_8$ can form a 4-6 member ring;

$R_{10}$ and $R_{11}$ are independently selected from H and $C_{1-4}$ alkyl; and $R_N$ is H or $C_{1-4}$ alkyl.

In embodiments, the present invention also provides compounds of Formula (II):

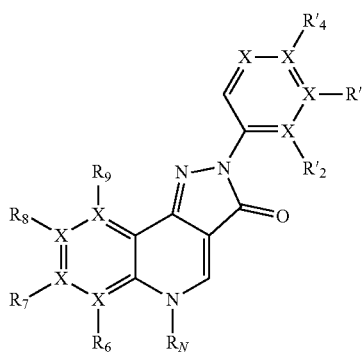

(II)

wherein
each X is independently C or N;
$R'_2$, $R'_3$ and $R'_4$ are independently selected from H, $C_{1-4}$ alkyl, $C_{1-4}$ alkoxy, halogen, $NR_{10}R_{11}$, $NO_2$, hydroxyl, cyano, $C_{1-4}$ alkylthio, —C(O)$C_{1-4}$ alkyl, or —C(O)$NR_{10}R_{11}$;
$R_6$, $R_7$, $R_8$ and $R_9$ are independently selected from H, $C_{1-4}$ alkyl, $C_{1-4}$ alkoxy, and halogen; $NR_{10}R_{11}$, $NO_2$, hydroxyl, cyano, $C_{1-4}$ alkylthio, —C(O)$C_{1-4}$ alkyl, or —C(O)$NR_{10}R_{11}$, or $R_6$ and $R_7$ or $R_7$ and $R_8$ can form a 4-6 member ring;
$R_{10}$ and $R_{11}$ are independently selected from H and $C_{1-4}$ alkyl; and
$R_N$ is H or $C_{1-4}$ alkyl;
wherein at least one of $R'_2$, $R'_3$, $R'_4$, $R_6$, $R_7$, $R_8$, $R_9$, $R_{10}$, $R_{11}$ and $R_N$ contains at least one deuterium.

In embodiments these compounds rescue METH-induced PPI impairment in mice, a mouse model mimicking sensorimotor gating deficit in several neuropsychiatric disorders, such as, but not limited to, neuropsychiatric disorders with sensorimotor gating deficits, such as schizophrenia, tic disorders, attention deficit hyperactivity disorder, obsessive compulsive disorder, panic disorder, Huntington's disease, and nocturnal enuresis.

In embodiments these compounds also reduce the number of activated neurons in trigeminal nucleus caudalis (TNC) induced by intra-cisternal capsaicin injection, an animal model mimicking migraine, and rats with reduced α6 $GABA_ARs$ in trigeminal ganglia were hypersensitive to TMJ inflammation), as well as in animal model of trigeminal neuropathic pain.

In embodiments these compounds modulate hearing disorders, such as but not limited to tinnitus, as α6-containing $GABA_A$ receptors are also expressed in the cochlear nucleus.

Definitions

Definitions of specific functional groups and chemical terms are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5th Edition, John Wiley & Sons, Inc., New York, 2001; Larock, Comprehensive Organic Transformations, VCH Publishers, Inc., New York, 1989; Carruthers, Some Modern Methods of Organic Synthesis, 3rd Edition, Cambridge University Press, Cambridge, 1987; the entire contents of each of which are incorporated herein by reference.

The term "acyl" refers to an alkylcarbonyl, cycloalkylcarbonyl, heterocyclylcarbonyl, arylcarbonyl, or heteroarylcarbonyl substituent, any of which may be further substituted (e.g., with one or more substituents).

The term "alkyl" refers to a straight or branched hydrocarbon chain, containing the indicated number of carbon atoms. For example, $C_1$-$C_{12}$ alkyl indicates that the alkyl group may have from 1 to 12 (inclusive) carbon atoms, and $C_1$-$C_4$ alkyl indicates that the alkyl group may have from 1 to 4 (inclusive) carbon atoms. An alkyl group may be optionally substituted. Examples of $C_1$-$C_4$ alkyl groups include methyl, ethyl, n-propyl, isopropyl, n-butyl, sec-butyl, and tert-butyl.

The term "alkenyl" refers to a straight or branched hydrocarbon chain having one or more double bonds. Examples of alkenyl groups include, but are not limited to, allyl, propenyl, 2-butenyl, 3-hexenyl, and 3-octenyl groups. One of the double bond carbons may optionally be the point of attachment of the alkenyl substituent. An alkenyl group may be optionally substituted.

The term "alkynyl" refers to a straight or branched hydrocarbon chain having one or more triple bonds. Examples of alkynyl groups include, but are not limited to, ethynyl, propargyl, and 3-hexynyl. One of the triple bond carbons may optionally be the point of attachment of the alkynyl substituent. An alkynyl group may be optionally substituted.

The term "aryl" refers to an aromatic monocyclic, bicyclic, or tricyclic hydrocarbon ring system, wherein any ring atom capable of substitution can be substituted (e.g., with one or more substituents). Examples of aryl moieties include, but are not limited to, phenyl, naphthyl, and anthracenyl.

The term "arylalkyl" refers to an alkyl moiety in which an alkyl hydrogen atom is replaced with an aryl group. Arylalkyl includes groups in which more than one hydrogen atom has been replaced with an aryl group. Examples of arylalkyl groups include benzyl, 2-phenylethyl, 3-phenylpropyl, 9-fluorenyl, benzhydryl, and trityl groups.

The term "cycloalkyl" as used herein refers to nonaromatic, saturated or partially unsaturated cyclic, bicyclic, tricyclic, or polycyclic hydrocarbon groups having 3 to 12 carbons (e.g., 3, 4, 5, 6 or 7 carbon atoms). Any ring atom can be substituted (e.g., with one or more substituents). Cycloalkyl groups can contain fused rings. Fused rings are rings that share one or more common carbon atoms. Examples of cycloalkyl groups include, but are not limited to, cyclopropyl, cyclobutyl, cyclopentyl, cyclohexyl, cyclohexenyl, cyclohexadienyl, methylcyclohexyl, adamantyl, norbornyl, and norbornenyl.

The term "halo" or "halogen" as used herein refers to any radical of fluorine, chlorine, bromine, or iodine.

The term "haloalkyl" as used herein refers to an alkyl in which one or more hydrogen atoms are replaced with a halogen, and includes alkyl moieties in which all hydrogens have been replaced with halogens (e.g., perfluoroalkyl such as $CF_3$).

The term "heteroaryl" as used herein refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms independently selected from O, N, S, P, and Si (e.g., carbon atoms and 1-3, 1-6, or 1-9 heteroatoms independently selected from O, N, S, P, and Si if monocyclic, bicyclic, or tricyclic, respectively). Any ring atom can be substituted (e.g., with one or more substituents). Heteroaryl groups can contain fused rings, which are rings that share one or more common atoms. Examples of heteroaryl groups include, but are not limited to, radicals of pyridine, pyrimidine, pyrazine, pyridazine, pyrrole, imidazole, pyrazole, oxazole, isoxazole, furan, thiazole, isothiazole, thiophene, quinoline, isoquinoline, quinoxaline, quinazoline, cinnoline, indole, isoindole, indolizine, indazole, benzimidazole, phthalazine, pteridine, carbazole, carboline, phenanthridine, acridine, phenanthroline, phenazine, naphthyridines, and purines.

The term "heterocyclyl" as used herein refers to a non-aromatic, saturated or partially unsaturated 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, S, Si, and P (e.g., carbon atoms and 1-3, 1-6, or 1-9 heteroatoms of O, N, S, Si, and P if monocyclic, bicyclic, or tricyclic, respectively). Any ring atom can be substituted (e.g., with one or more substituents). Heterocyclyl groups can contain fused rings, which are rings that share one or more common atoms. Examples of heterocyclyl groups include, but are not limited to, radicals of tetrahydrofuran, tetrahydrothiophene, tetrahydropyran, piperidine, piperazine, morpholine, pyrroline, pyrimidine, pyrrolidine, indoline, tetrahydropyridine, dihydropyran, thianthrene, pyran, benzopyran, xanthene, phenoxathiin, phenothiazine, furazan, lactones, lactams such as azetidinones and pyrrolidinones, sultams, sultones, and the like.

The term "hydroxy" refers to an —OH radical. The term "alkoxy" refers to an —O-alkyl radical. The term "aryloxy" refers to an —O-aryl radical. The term "haloalkoxy" refers to an —O-haloalkyl radical.

The term "substituent" refers to a group "substituted" on an alkyl, alkenyl, alkynyl, cycloalkyl, heterocyclyl, aryl, arylalkyl, or heteroaryl group at any atom of that group. Suitable substituents include, without limitation: acyl, acylamido, acyloxy, alkoxy, alkyl, alkenyl, alkynyl, amido, amino, carboxy, cyano, ester, halo, hydroxy, imino, nitro, oxo (e.g., C═O), phosphonate, sulfinyl, sulfonyl, sulfonate, sulfonamino, sulfonamido, thioamido, thiol, thioxo (e.g., C═S), and ureido. In embodiments, substituents on a group are independently any one single, or any combination of the aforementioned substituents. In embodiments, a substituent may itself be substituted with any one of the above substituents.

The above substituents may be abbreviated herein, for example, the abbreviations Me, Et and Ph represent methyl, ethyl, and phenyl, respectively. A more comprehensive list of the abbreviations used by organic chemists appears in the first issue of each volume of the Journal of Organic Chemistry; this list is typically presented in a table entitled Standard List of Abbreviations. The abbreviations contained in said list, and all abbreviations used by organic chemists of ordinary skill in the art, are hereby incorporated by reference.

For compounds, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

Where substituent groups are specified by their conventional chemical formulae, written from left to right, they optionally encompass substituents resulting from writing the structure from right to left, e.g., —CH₂O— optionally also recites —OCH₂—.

In accordance with a convention used in the art, the group:

is used in structural formulas herein to depict the bond that is the point of attachment of the moiety or substituent to the core or backbone structure.

In the context of treating a disorder, the term "effective amount" as used herein refers to an amount of the compound or a composition comprising the compound which is effective, upon single or multiple dose administrations to a subject, in treating a cell, or curing, alleviating, relieving, or improving a symptom of the disorder in a subject. An effective amount of the compound or composition may vary according to the application. In the context of treating a disorder, an effective amount may depend on factors such as the disease state, age, sex, and weight of the individual, and the ability of the compound to elicit a desired response in the individual. In an example, an effective amount of a compound is an amount that produces a statistically significant change in a given parameter as compared to a control, such as in cells (e.g., a culture of cells) or a subject not treated with the compound.

It is specifically understood that any numerical value recited herein (e.g., ranges) includes all values from the lower value to the upper value, i.e., all possible combinations of numerical values between the lowest value and the highest value enumerated are to be considered to be expressly stated in this application. For example, if a concentration range is stated as 1% to 50%, it is intended that values such as 2% to 40%, 10% to 30%, or 1% to 3%, etc., are expressly enumerated in in this specification. These are only examples of what is specifically intended.

Compounds

Some pyrazoloquinolinone compounds have selective activity at GABA$_A$ α6β3γ2 receptors. In addition, some also modulate α6βδ receptors. In an aspect, the present invention relates to compounds that are selective for such GABA$_A$ α6-containing receptors.

In embodiments, the present invention provides compounds of Formula (I):

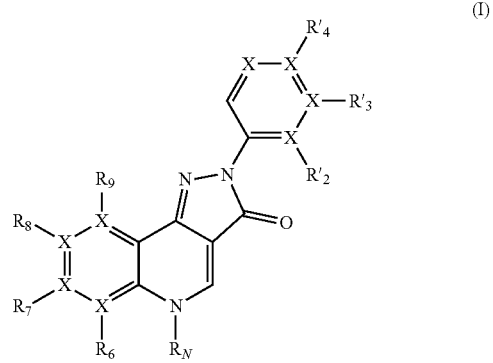

wherein
each X is independently C or N;
R'$_2$, R'$_3$ and R'$_4$ are independently selected from H, C$_{1-4}$ alkyl, C$_{1-4}$ alkoxy, halogen, NR$_{10}$R$_{11}$, NO$_2$, hydroxyl, cyano, C$_{1-4}$ alkylthio, —C(O)C$_{1-4}$ alkyl, or —C(O)NR$_{10}$R$_{11}$;
R$_6$, R$_7$, R$_8$ and R$_9$ are independently selected from H, C$_{1-4}$ alkyl, C$_{1-4}$ alkoxy, halogen, NR$_{10}$R$_{11}$, NO$_2$, hydroxyl, cyano, C$_{1-4}$ alkylthio, —C(O)C$_{1-4}$ alkyl, or —C(O)NR$_{10}$R$_{11}$, or R$_6$ and R$_7$ or R$_7$ and R$_8$ can form a 4-6 member ring;
R$_{10}$ and R$_{11}$ are independently selected from H and C$_{1-4}$ alkyl; and
R$_N$ is H or C$_{1-4}$ alkyl.

In embodiments, the compound of Formula (I) is not

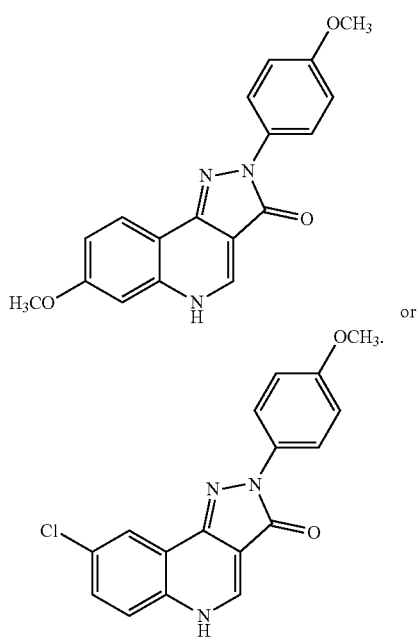

or

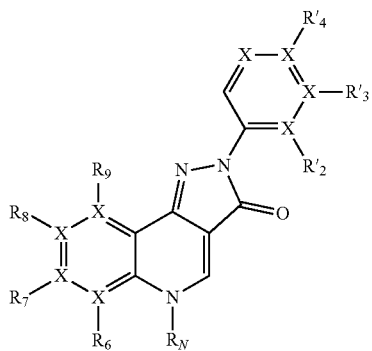

The present invention also provides compounds of Formula (II):

(II)

wherein
each X is independently C or N;
R'$_2$, R'$_3$ and R'$_4$ are independently selected from H, C$_{1-4}$ alkyl, C$_{1-4}$ alkoxy, halogen, NR$_{10}$R$_{11}$, NO$_2$, hydroxyl, cyano, C$_{1-4}$ alkylthio, —C(O)C$_{1-4}$ alkyl, or —C(O)NR$_{10}$R$_{11}$;
R$_6$, R$_7$, R$_8$ and R$_9$ are independently selected from H, C$_{1-4}$ alkyl, C$_{1-4}$ alkoxy, and halogen; NR$_{10}$R$_{11}$, NO$_2$, hydroxyl, cyano, C$_{1-4}$ alkylthio, —C(O)C$_{1-4}$ alkyl, or —C(O)NR$_{10}$R$_{11}$, or R$_6$ and R$_7$ or R$_7$ and R$_8$ can form a 4-6 member ring;
R$_{10}$ and R$_{11}$ are independently selected from H and C$_{1-4}$ alkyl; and
R$_N$ is H or C$_{1-4}$ alkyl;
wherein at least one of R'$_2$, R'$_3$, R'$_4$, R$_6$, R$_7$, R$_8$, R$_9$, R$_{10}$, R$_{11}$ and R$_N$ contains at least one deuterium.

In some embodiments, at least one of R'$_2$, R'$_3$, R'$_4$, R$_6$, R$_7$, R$_8$, R$_9$, R$_{10}$, R$_{11}$, and R$_N$ is a haloalkyl such as CF$_3$. In embodiments, at least one of R'$_2$, R'$_3$, R'$_4$, R$_6$, R$_7$, R$_8$, R$_9$, R$_{10}$, R$_{11}$, and R$_N$ is C14 alkoxy, such as methoxy or —OCD$_3$. In embodiments, at least one of R'$_2$, R'$_3$, R'$_4$, R$_6$, R$_7$, R$_8$, and R$_9$ is a halogen, such as chlorine or bromine. In embodiments, R$_N$ is H. In embodiments, each X is C. In embodiments, at least one X is N.

In an embodiment, the compound of Formula (I) may be:

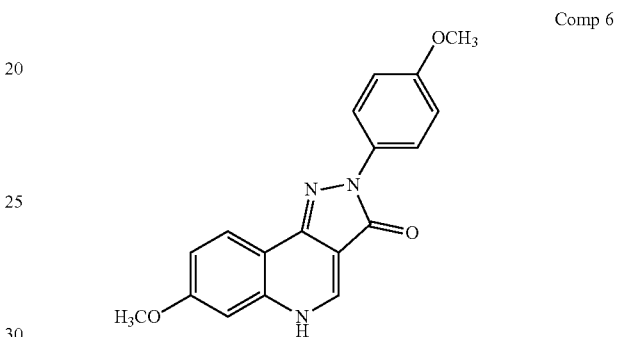

Comp 6

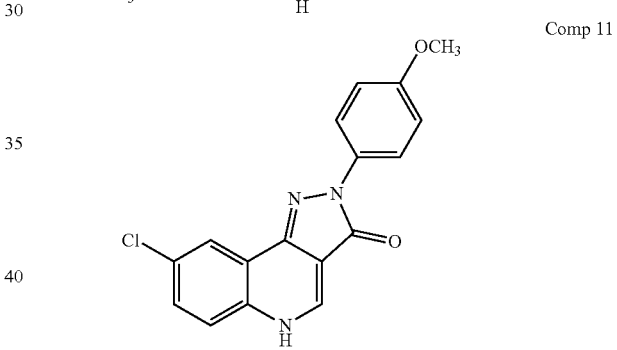

Comp 11

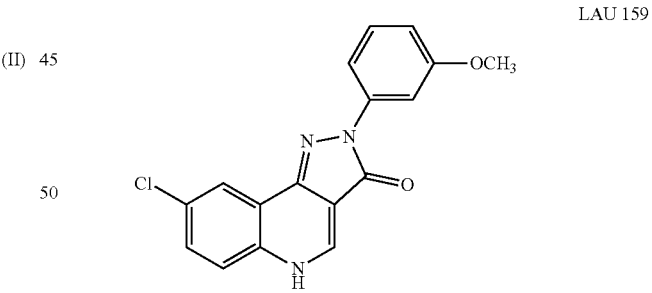

LAU 159

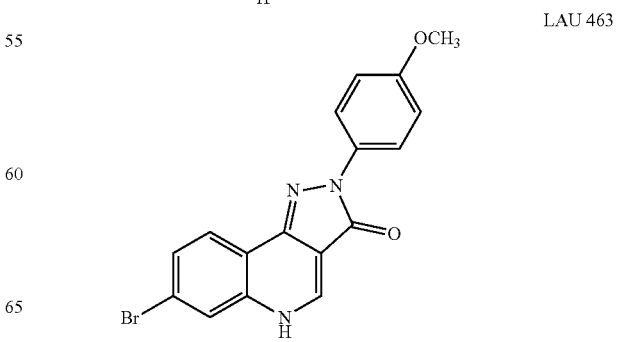

LAU 463

In an embodiment, the compound of Formula (II) may be:

In an embodiment, the compound of Formulae (I) or (II) may be:
DK-II-59-1
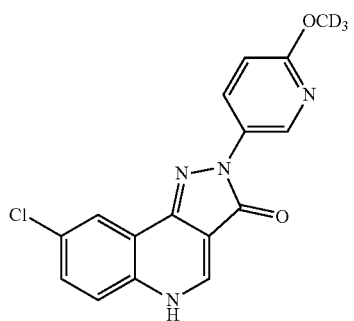
DK-I-88-1
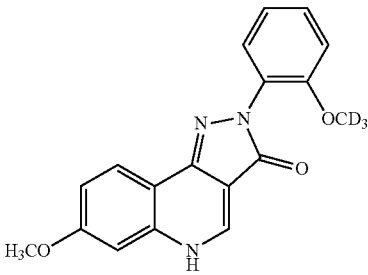
DK-II-58-1
DK-I-94-1
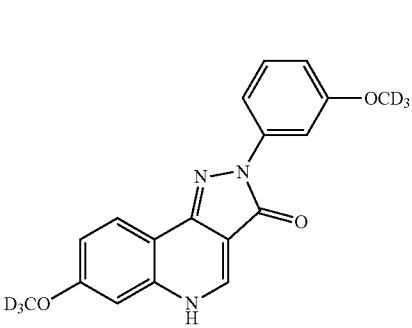
DK-I-60-3
DK-I-90-1
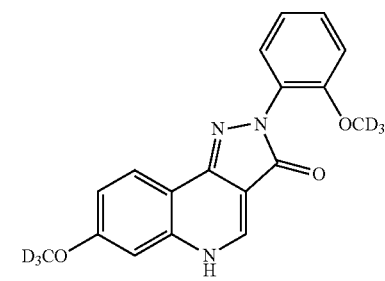
DK-II-60-1
DK-I-95-3
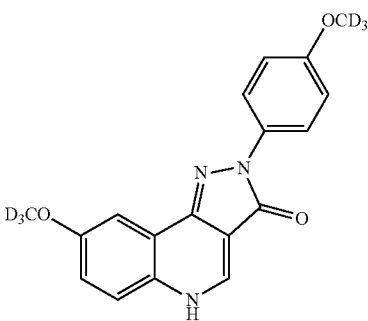
DK-I-87-1
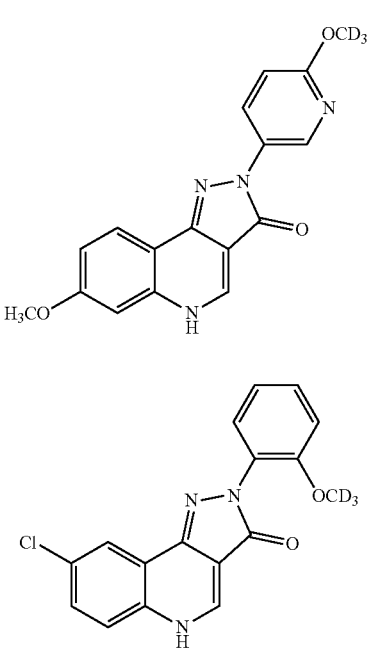
DK-I-97-1
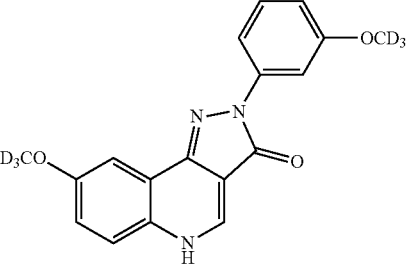

-continued
DK-I-98-1
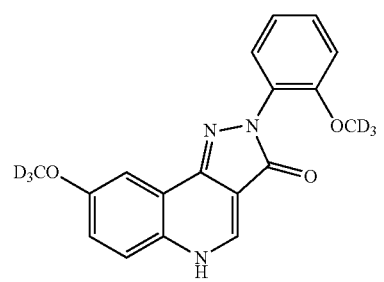
RV-I-037
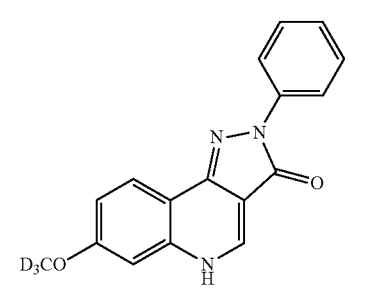
DK-I-92-1
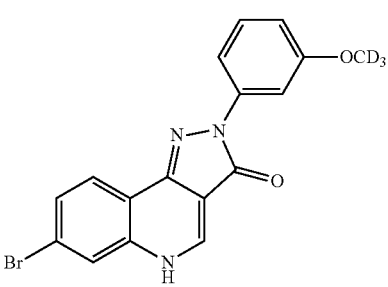
DK-I-89-1
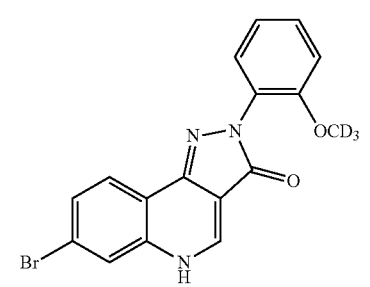
CW-02-073
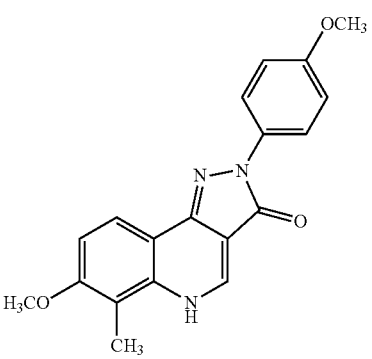
-continued
CW-02-078
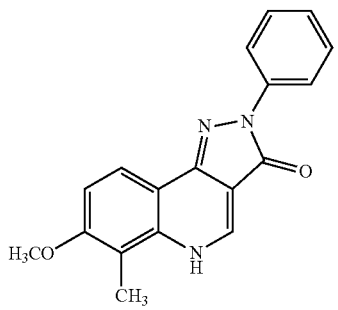
CW-02-078
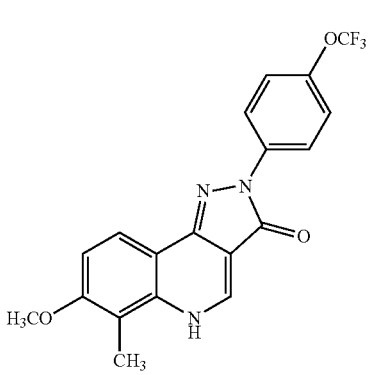
CW-02-082
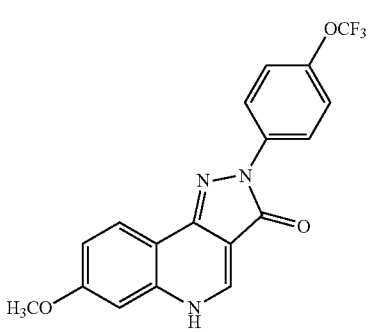
LAU 176
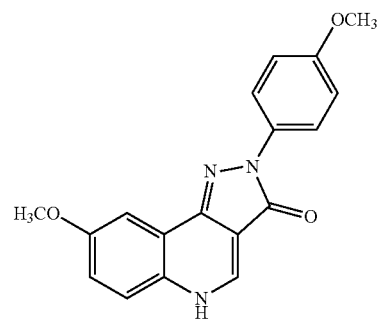
LAU 165
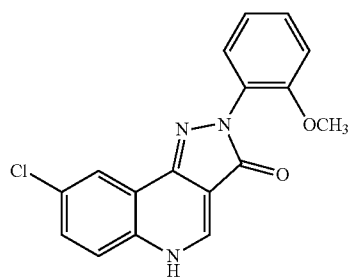

MM-I-03
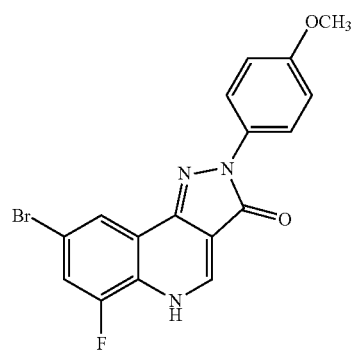
MM-I-13
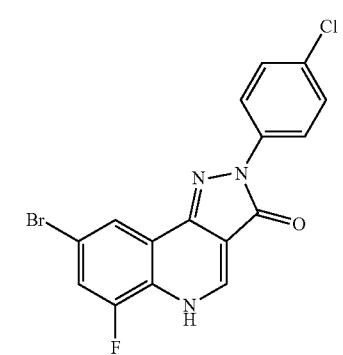
MM-I-08
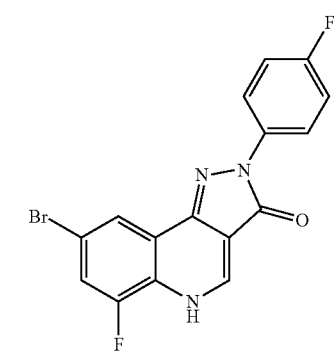
MM-I-06
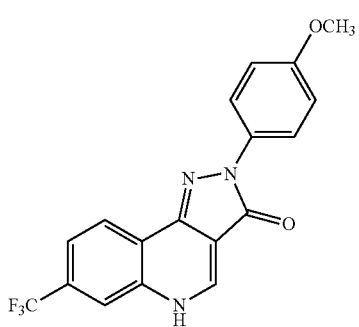
MM-I-08
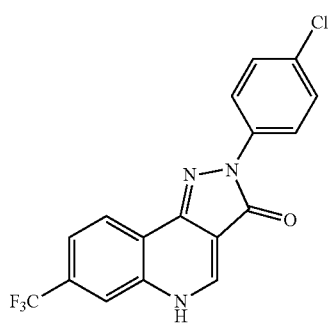
MM-I-09
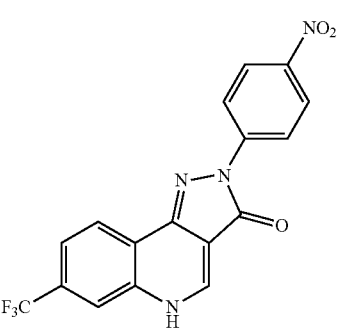
MM-I-10
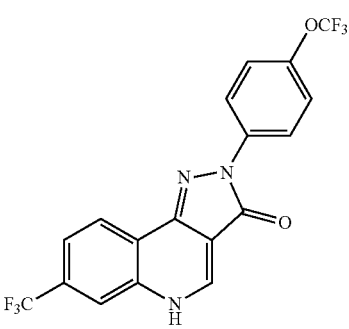
MM-I-11
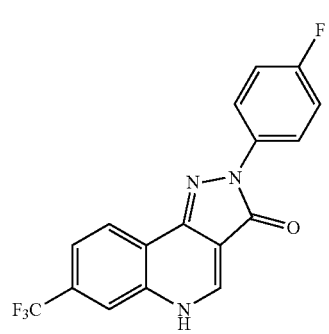
MM-I-12
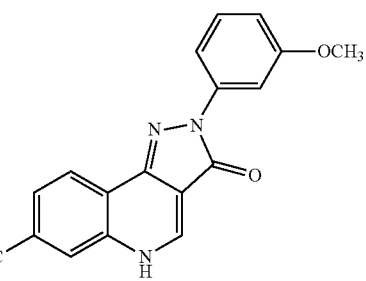

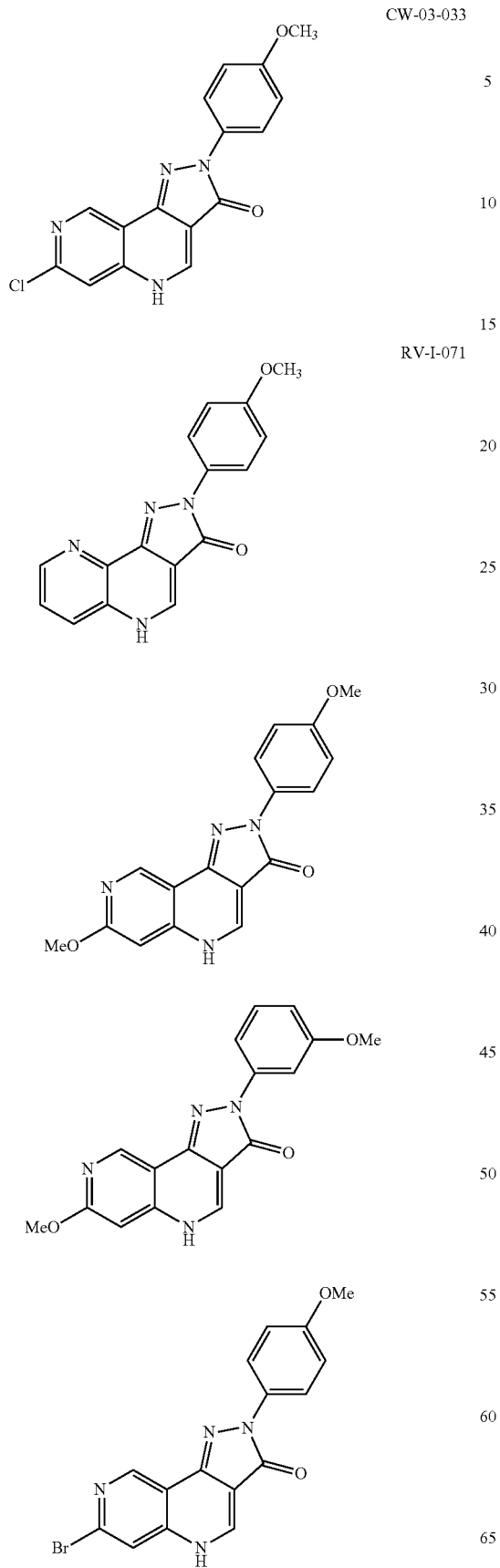
CW-03-033
RV-I-071
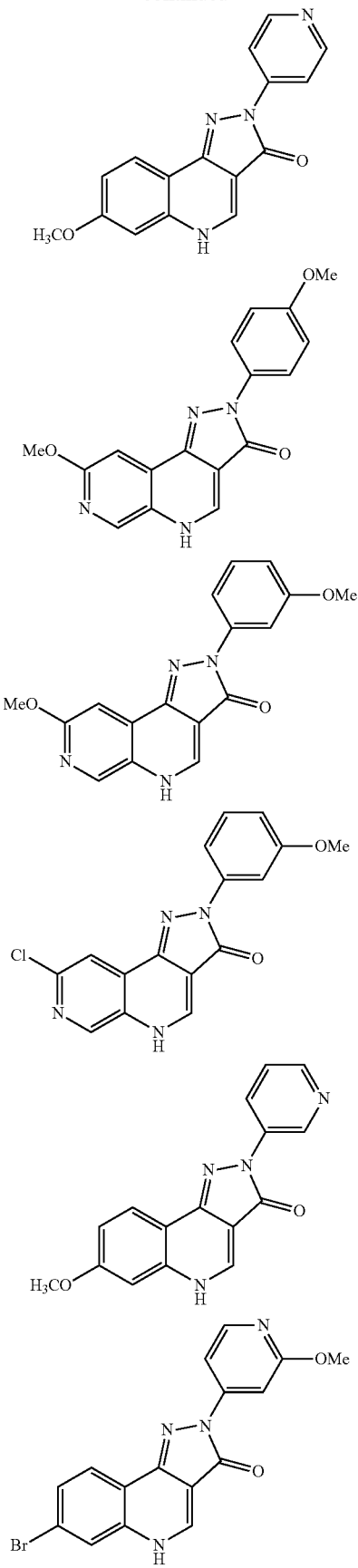

-continued
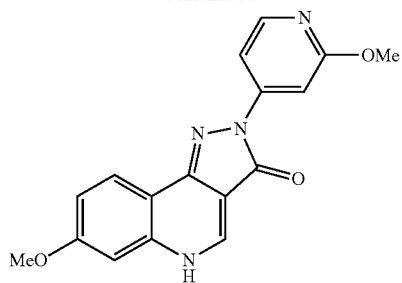
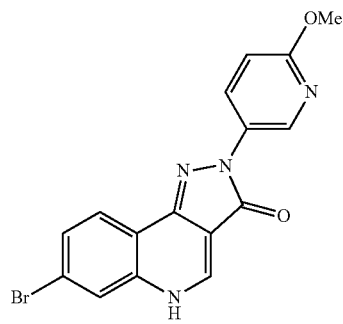
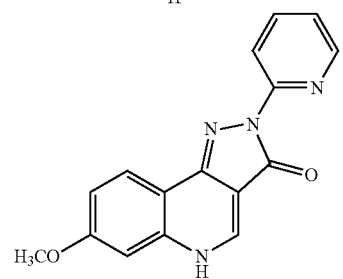
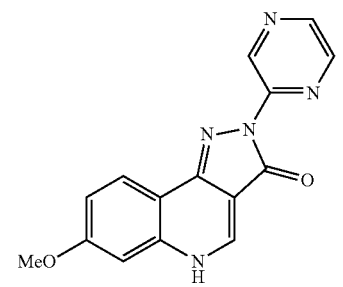
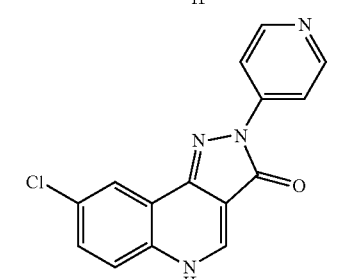
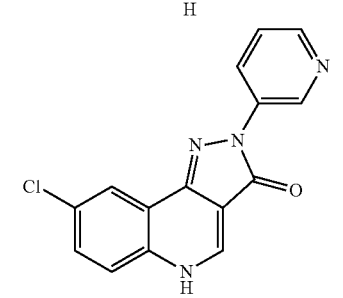
-continued
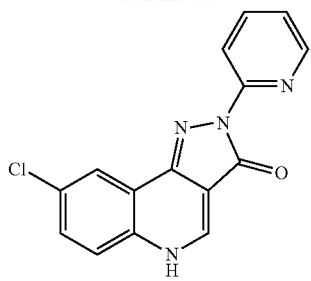
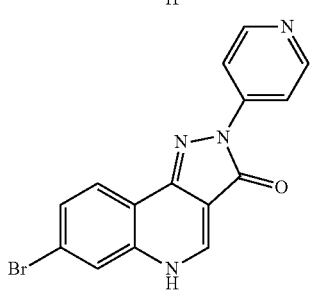
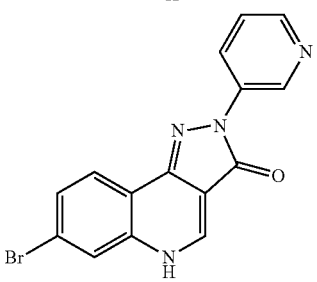
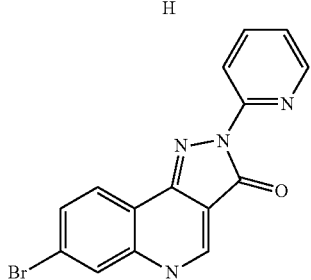
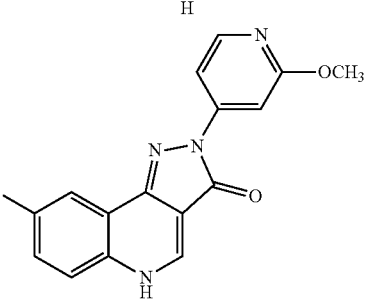
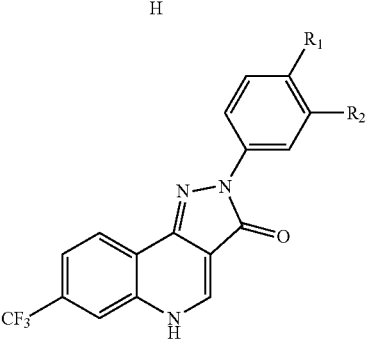

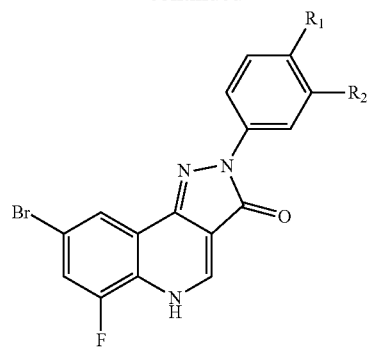
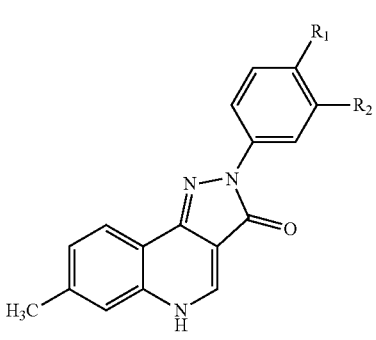
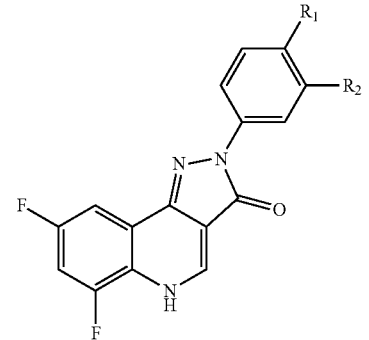
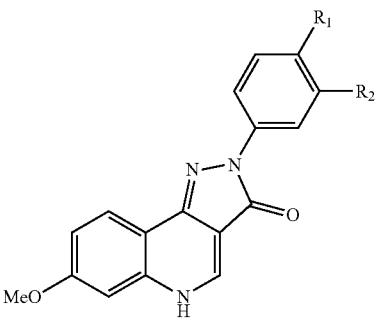
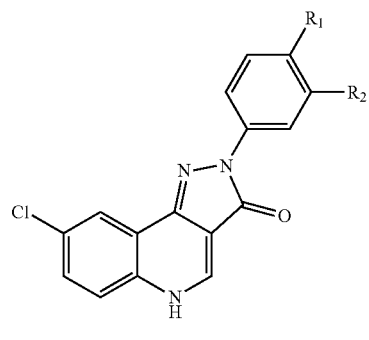
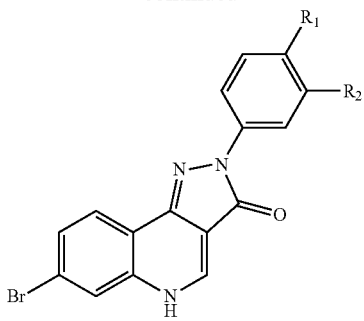
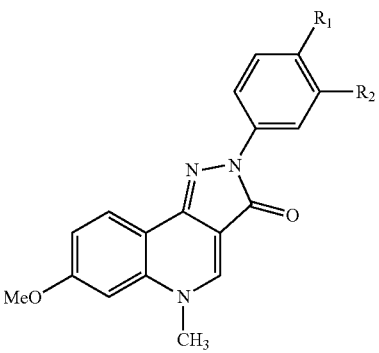
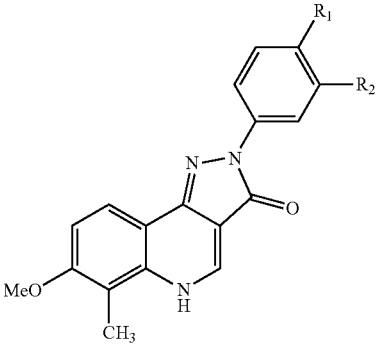
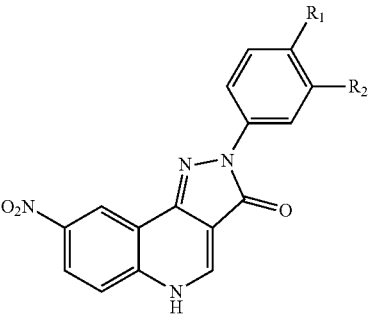
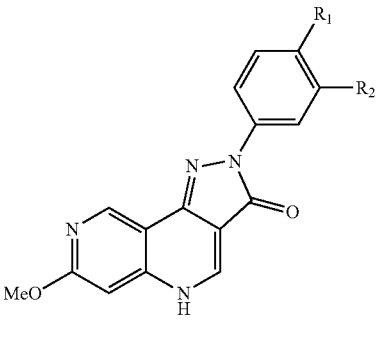

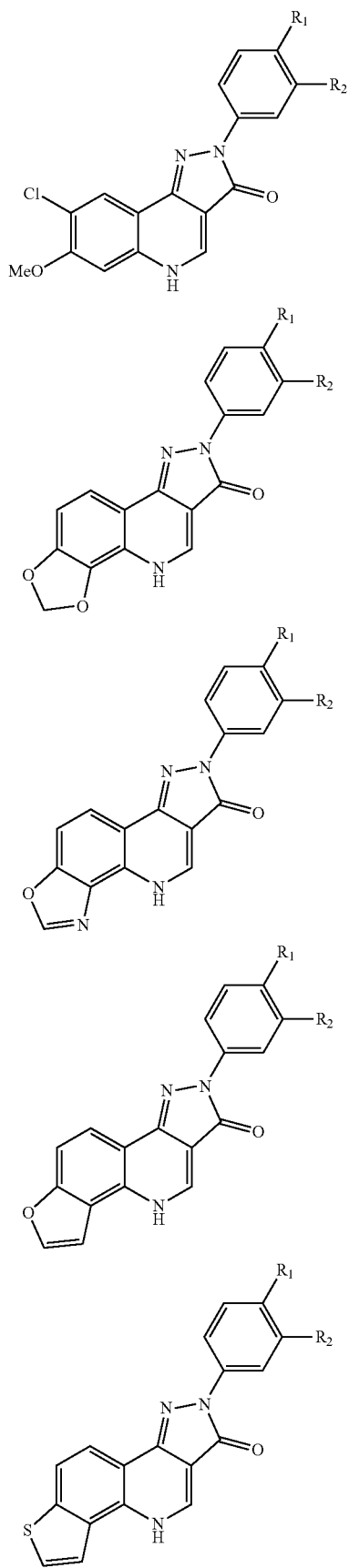
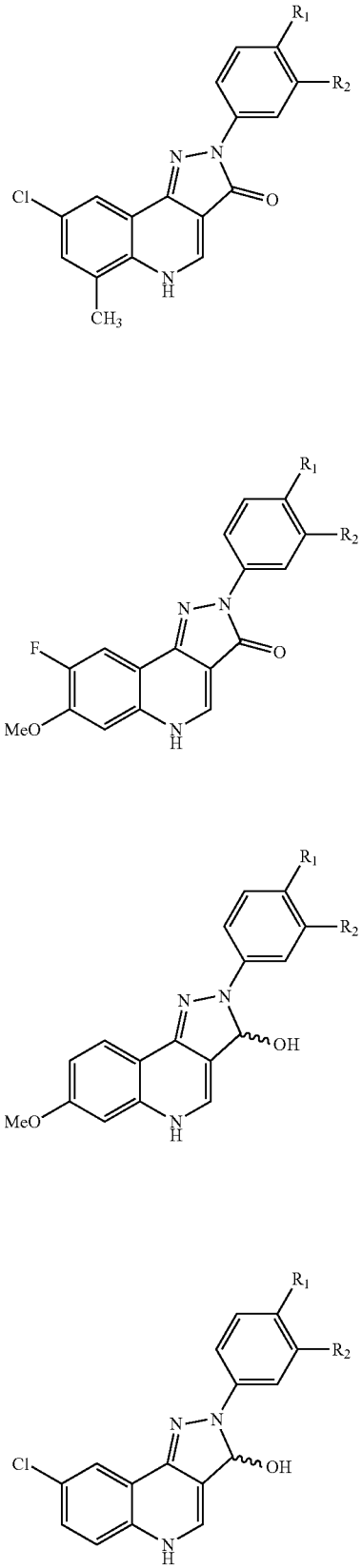
wherein $R_1$ and $R_2$ are independently H, $OCH_3$, $OCD_3$, OEt, $OCF_3$, F, Cl, Br, or $NO_2$.

In an embodiment, the compound of Formula (II) may be:
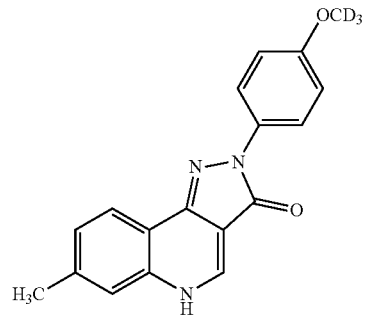
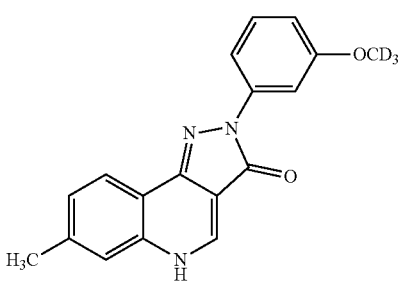
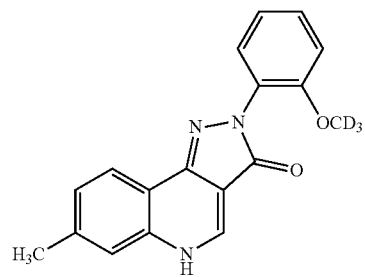
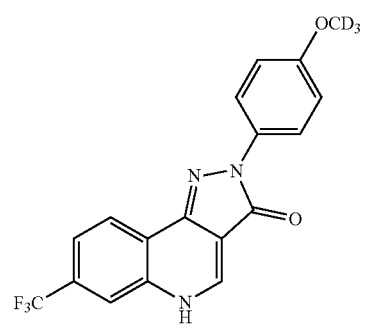
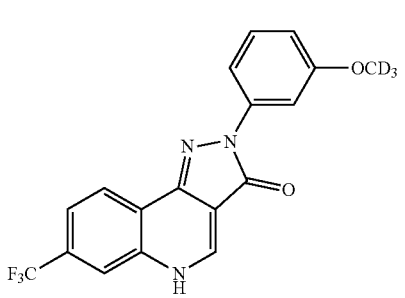
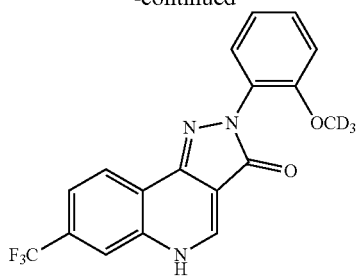
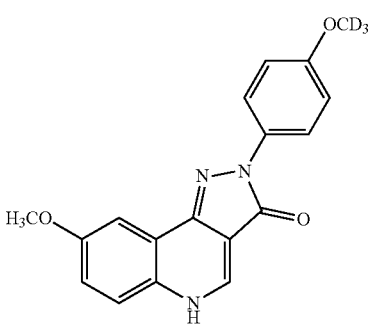
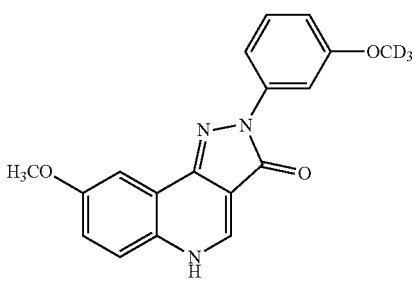
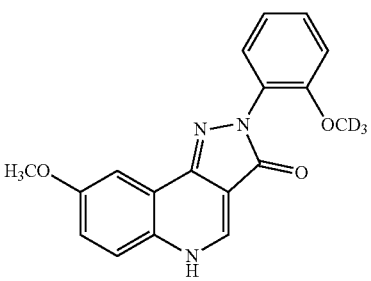
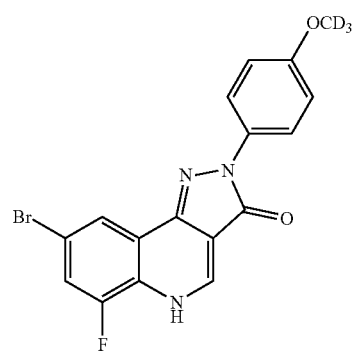

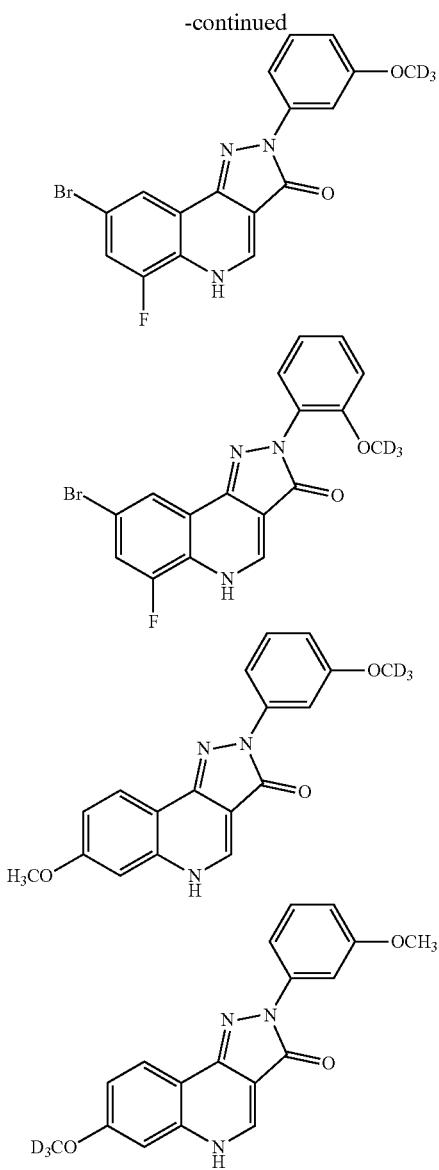

In some aspects the compounds of the present invention selectively target GABA$_A$ receptors of α6δγ2 composition. In some aspects, the compounds of the present invention are allosteric modulators of the GABA$_A$ receptors that are selective for the α6+/β− allosteric modulatory sites on GABA$_A$ receptors.

For compounds according to the present invention, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

Where substituent groups are specified by their conventional chemical formulae, written from left to right, they optionally encompass substituents resulting from writing the structure from right to left, e.g., —CH$_2$O— optionally also recites —OCH$_2$—.

Compounds according to the present invention include compounds that differ only in the presence of one or more isotopically enriched atoms. For example, compounds may have the present structures except for the replacement of hydrogen by deuterium or tritium, or the replacement of a carbon by a $^{13}$C- or $^{14}$C-enriched carbon.

A compound according to the present invention can be in the form of a salt, e.g., a pharmaceutically acceptable salt. The term "pharmaceutically acceptable salt" includes salts of the active compounds that are prepared with relatively nontoxic acids or bases, depending on the particular substituents found on the compounds. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulfuric acid, methanesulfonic acid, fumaric acid, maleic acid, succinic acid, acetic acid, benzoic acid, oxalic acid, citric acid, tartaric acid, carbonic acid, or phosphoric acid. Furthermore, where the compounds of the invention carry an acidic moiety, suitable pharmaceutically acceptable salts thereof may include alkali metal salts, e.g. sodium or potassium salts, alkaline earth metal salts, e.g. calcium or magnesium salts; and salts formed with suitable organic ligands, e.g. quaternary ammonium salts.

Neutral forms of the compounds may be regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of this disclosure.

In addition to salt forms, the present invention may also provide compounds according to the present invention in a prodrug form. Prodrugs of the compounds are those compounds that readily undergo chemical changes under physiological conditions to provide the active compounds. Prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Compounds according to the present invention can be, for example, an enantiomerically enriched isomer of a stereoisomer described herein. Enantiomer, as used herein, refers to either of a pair of chemical compounds whose molecular structures have a mirror-image relationship to each other. For example, a compound may have an enantiomeric excess of at least about 10%, 15%, 20%, 25%, 30%, 35%, 40%, 45%, 50%, 55%, 60%, 65%, 70%, 75%, 80%, 85%, 90%, 95%, 96%, 97%, 98%, or 99%.

A preparation of a compound according to the present invention may be enriched for an isomer of the compound having a selected stereochemistry, e.g., R or S, corresponding to a selected stereocenter. For example, the compound may have a purity corresponding to a compound having a selected stereochemistry of a selected stereocenter of at least about 60%, 65%, 70%, 75%, 80%, 85%, 90%, 95%, 96%, 97%, 98%, or 99%. A compound can, for example, include a preparation of a compound disclosed herein that is enriched for a structure or structures having a selected stereochemistry, e.g., R or S, at a selected stereocenter.

In some embodiments, a preparation of a compound according to the present invention may be enriched for isomers (subject isomers) which are diastereomers of the compound. Diastereomer, as used herein, refers to a stereoisomer of a compound having two or more chiral centers that is not a mirror image of another stereoisomer of the same compound. For example, the compound may have a purity corresponding to a compound having a selected diastereomer of at least about 60%, 65%, 70%, 75%, 80%, 85%, 90%, 95%, 96%, 97%, 98%, or 99%.

When no specific indication is made of the configuration at a given stereocenter in a compound, any one of the configurations or a mixture of configurations is intended.

A compound according to the present invention can also be modified by appending appropriate functionalities to enhance selective biological properties. Such modifications are known in the art and include those that increase biological penetration into a given biological system (e.g., blood, lymphatic system, central nervous system), increase oral availability, increase solubility to allow administration by injection, alter metabolism, and/or alter rate of excretion. Examples of these modifications include, but are not limited to, esterification with polyethylene glycols, derivatization with pivolates or fatty acid substituents, conversion to carbamates, hydroxylation of aromatic rings, and heteroatom substitution in aromatic rings.

Synthesis

Figure 25A:
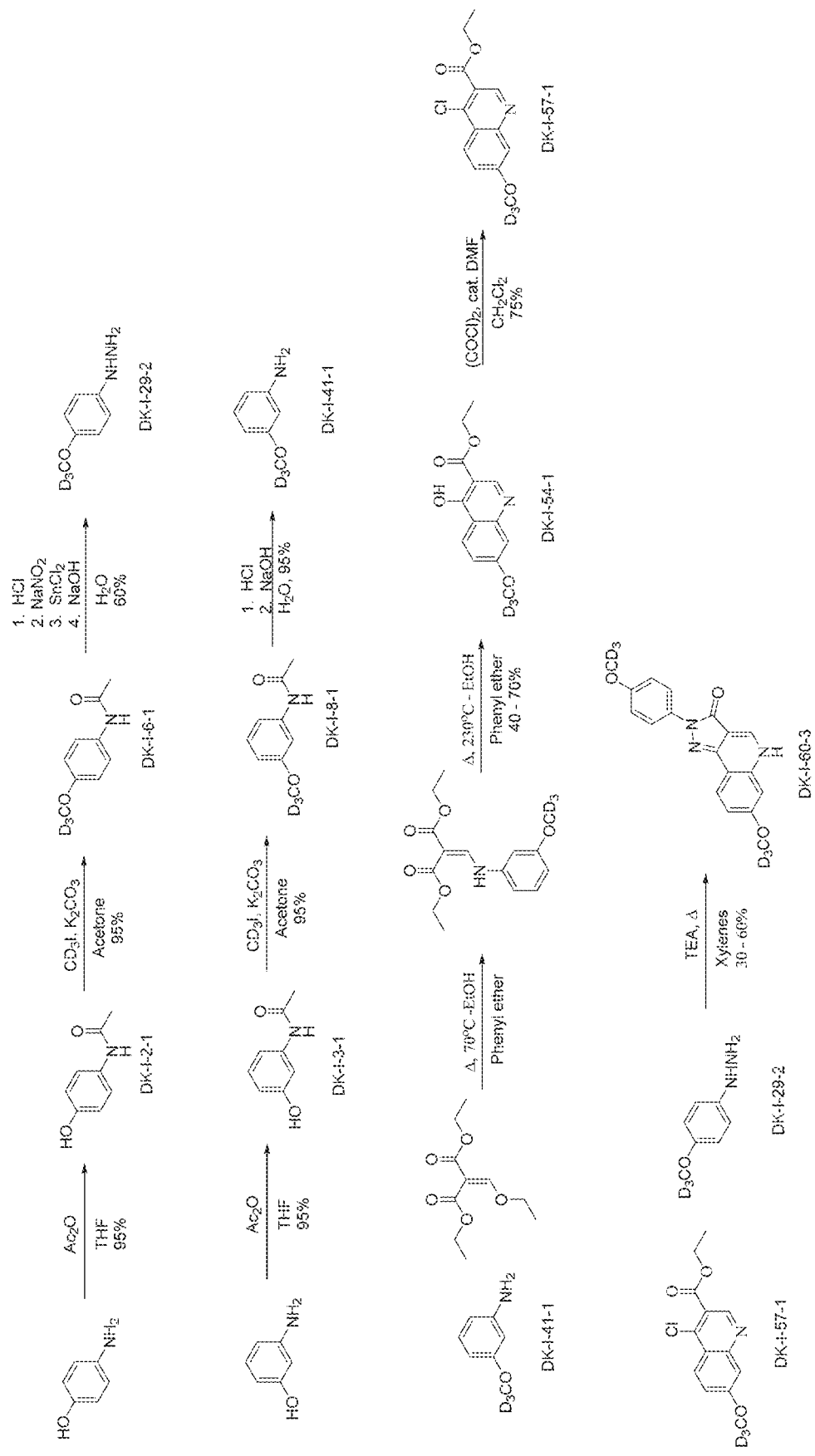
FIGS. 25A and 25B show synthetic schemes for the preparation of compounds.
Figure 25B:
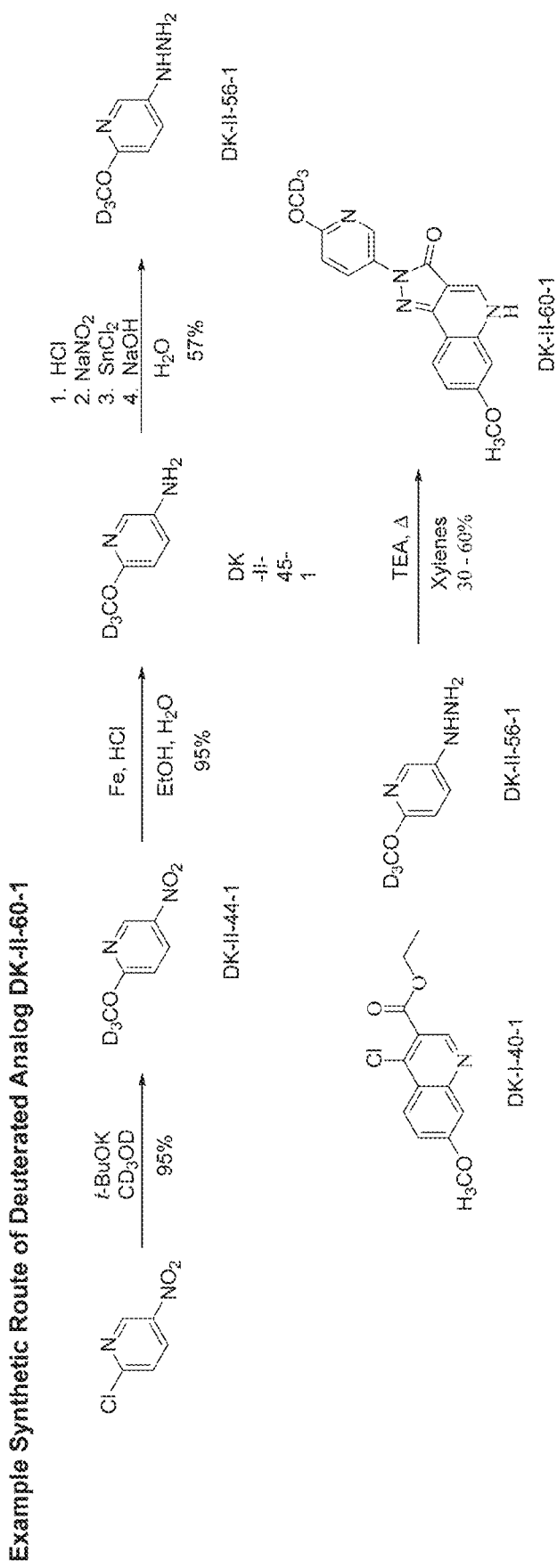

Compounds of formulae (I) and (II) may be synthesized using commercially available starting materials according to the methods described in the examples. Compounds according to Formula (II) may also be synthesized according to the methods shown in FIGS. 25A and 25B.

Other methods of synthesizing the compounds of the formulae herein will be evident to those of ordinary skill in the art. Synthetic chemistry transformations and protecting group methodologies (protection and deprotection) useful in synthesizing the compounds are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., Encyclopedia of Reagents for Organic Synthesis, John Wiley and Sons (1995), and subsequent editions thereof.

Evaluation of Compounds

Compounds may be analyzed using a number of methods, including receptor binding studies, electrophysiological assays to quantify functional effects, and in vivo methods.

For example, the $GABA_A$ subunit selectivity of compounds can be evaluated, for example, using competitive binding assays. Such assays have been described (Choudhary et al. Mol Pharmacol. 1992, 42, 627-33; Savić et al. *Progress in Neuro-Psychopharmacology & Biological Psychiatry*, 2010, 34, 376-386). The assays involve the use of a radiolabeled compound known to bind to $GABA_A$ receptors, such as [$^3$H]flunitrazepam. Membrane proteins can be harvested and incubated with the radiolabeled compound, and non-specific binding can be evaluated by comparing binding of the radiolabeled compound to another, non-labeled compound (e.g., diazepam). Bound radioactivity can be quantified by liquid scintillation counting. Membrane protein concentrations can be determined using commercially available assay kits (e.g., from Bio-Rad, Hercules, Calif.).

Compounds can also be evaluated in electrophysiological assays in *Xenopus* oocytes. Compounds can be preapplied to the oocytes before the addition of GABA, which can then be coapplied with the compounds until a peak response is observed. Between applications, oocytes can be washed to ensure full recovery from desensitization. For current measurements, the oocytes can be impaled with microelectrodes, and recordings performed using two electrode voltage clamp recordings.

The compounds may possess selective efficacy for $\alpha 6\beta\gamma 2$ or other $\alpha 6$-containing $GABA_A$ receptors such that they enhance GABA elicited currents to a high degree in these receptors, and to a much lesser degree in all receptors containing $\alpha 1$, $\alpha 2$, 3, $\alpha 4$ and $\alpha 5$ subunits, as indicated in FIG. 24. The compounds may possess in addition affinity for the benzodiazepine binding sites of all subtypes, at which they are silent binders, meaning that they do not change GABA elicited currents by interacting with this binding site (see FIG. 1).

Other methods for evaluating compounds are known to those skilled in the art. To assess a compound's undesirable side effects (toxicity), animals may be monitored for overt signs of impaired neurological or muscular function. In mice, the rotorod procedure (Dunham, M. S. et al. J. Amer. Pharm. Ass. Sci. Ed. 1957, 46, 208-209) is used to disclose minimal muscular or neurological impairment. When a mouse is placed on a rod that rotates at a speed of 6 rpm, the animal can maintain its equilibrium for long periods of time. The animal is considered intoxicated if it falls off this rotating rod three times during a 1-min period. In rats, minimal motor deficit is indicated by ataxia, which is manifested by an abnormal, uncoordinated gait. Rats used for evaluating toxicity are examined before the test drug is administered, since individual animals may have peculiarities in gait, equilibrium, placing response, etc., which might be attributed erroneously to the test substance. In addition to MMI, animals may exhibit a circular or zigzag gait, abnormal body posture and spread of the legs, tremors, hyperactivity, lack of exploratory behavior, somnolence, stupor, catalepsy, loss of placing response, and changes in muscle tone.

Compositions and Routes of Administration

In another aspect, the invention provides pharmaceutical compositions comprising one or more compounds of this invention in association with a pharmaceutically acceptable carrier. Such compositions may be in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual, or rectal administration, or for administration by inhalation or insufflation. It is also envisioned that compounds may be incorporated into transdermal patches designed to deliver the appropriate amount of the drug in a continuous fashion. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture for a compound of the present invention, or a pharmaceutically acceptable salt thereof. When referring to these preformulation compositions as homogeneous, it is meant that the active ingredient is dispersed evenly throughout the composition so that the composition may be easily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example, 1, 2, 5, 10, 25, 50, or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone, or gelatin.

Suitable dosage level is about 0.01 to 250 mg/kg per day, about 0.05 to 100 mg/kg per day, or about 0.05 to 5 mg/kg per day. The compounds may be administered on a regimen of 1 to 4 times per day, or on a continuous basis via, for example, the use of a transdermal patch.

Pharmaceutical compositions for enteral administration, such as nasal, buccal, rectal or, especially, oral administration, and for parenteral administration, such as intravenous, intramuscular, subcutaneous, peridural, epidural, or intrathecal administration, are suitable. The pharmaceutical compositions comprise from approximately 1% to approximately 95% active ingredient, or from approximately 20% to approximately 90% active ingredient.

For parenteral administration including intracoronary, intracerebrovascular, or peripheral vascular injection/infusion preference is given to the use of solutions of the subunit selective $GABA_A$ receptor agonist, and also suspensions or dispersions, especially isotonic aqueous solutions, dispersions or suspensions which, for example, can be made up shortly before use. The pharmaceutical compositions may be sterilized and/or may comprise excipients, for example preservatives, stabilizers, wetting agents and/or emulsifiers, solubilizers, viscosity-increasing agents, salts for regulating osmotic pressure and/or buffers and are prepared in a manner known per se, for example by means of conventional dissolving and lyophilizing processes.

For oral pharmaceutical preparations suitable carriers are especially fillers, such as sugars, for example lactose, saccharose, mannitol or sorbitol, cellulose preparations and/or calcium phosphates, and also binders, such as starches, cellulose derivatives and/or polyvinylpyrrolidone, and/or, if desired, disintegrators, flow conditioners and lubricants, for example stearic acid or salts thereof and/or polyethylene glycol. Tablet cores can be provided with suitable, optionally enteric, coatings. Dyes or pigments may be added to the tablets or tablet coatings, for example for identification purposes or to indicate different doses of active ingredient. Pharmaceutical compositions for oral administration also include hard capsules consisting of gelatin, and also soft, sealed capsules consisting of gelatin and a plasticizer, such as glycerol or sorbitol. The capsules may contain the active ingredient in the form of granules, or dissolved or suspended in suitable liquid excipients, such as in oils.

Transdermal application is also considered, for example using a transdermal patch, which allows administration over an extended period of time, e.g. from one to twenty days.

Methods of Treatment

The present invention also provides methods of treating diseases and/or conditions which are regulated by the $\alpha6GABA_ARs$ comprising administering to a subject in need thereof an effective amount of a compound or composition as described herein. In embodiments, the present invention provides a method of treating a disease comprising administering to a subject in need thereof an effective amount of compound or composition described herein; wherein the disease is selected from the group consisting of neuropsychiatric disorders with sensorimotor gating deficits, such as schizophrenia, tic disorders, attention deficit hyperactivity disorder, obsessive compulsive disorder, panic disorder, Huntington's disease and nocturnal enuresis; depression; orofacial pains including but not limited to myofascial pain, trigeminoneuragia, and trigeminal neuropathic pain; migraine; and tinnitus.

Without wishing to be bound by theory, it is thought that the compounds described herein are functionally selective for $\alpha6\beta2,3\gamma2$ $GABA_A$ receptors and are positive allosteric modulators at this subtype. (See FIG. 2)

Sensorimotor Gating Function

The $\alpha6$ subunits of $GABA_A$ receptors exhibit a quite restricted regional distribution in the brain. $\alpha_6GABA_ARs$ are mainly expressed in cerebellar granule cells. $\alpha_6GABA_ARs$ are located synaptically as well as extrasynaptically and mediate inhibition induced by synaptically as well as tonically released and spillover GABA in cerebellar cells.

They thus mediate inhibitory synaptic transmission initiated by phasically released GABA as well as providing a tonic inhibitory control of the information flow. The $\alpha_6GABA_ARs$ are unresponsive to the classical benzodiazepine, diazepam.

PPI is a neurophysiological phenomenon in which the startle response to a stimulus (pulse) is inhibited if a weaker stimulus (prepulse) from the same source is preapplied within a short interval. The stimulus could be a sound, an airpuff, or a light. PPI is believed to be a processing protection in a living organism, serving as a preconscious regulator of attention, termed sensorimotor gating, to reduce the startle response that is harmful to the information processing. PPI can be assessed by the motor response in either humans (measuring the eyeblink response by electromyograph) or animals (measuring the startle jumping response). PPI disruptions are not only observed in Tourette Syndrome (TS) patients, but also in patients with other neuropsychiatric disorders, such as schizophrenia, ADHD, OCD, panic disorder, Huntington's disease, and nocturnal enuresis. ADHD and OCD are two common comorbidities of TS, and TS in childhood, which is a risk etiology of schizophrenia. Especially in patients with schizophrenia, PPI disruption is believed to be a typical endophenotype of cognitive function deficit, leading to hallucination due to a flood of sensory inputs. Based on the hyperdopaminergic hypothesis, animal models with hyperdominergic activity have been established, such as to treat animals with dopamine mimetic agents, such as methamphetamine, which facilitates dopamine release.

Without wishing to be bound by theory, recent studies suggest that activation of the cerebellum might play a role in PPI generation since 1) PPI is enhanced in mice without cerebellar output neuron (Purkinje cell)-specific glutamate receptor subunit; and 2) PPI is associated with decreased activation in the cerebellum.

Figure 6:
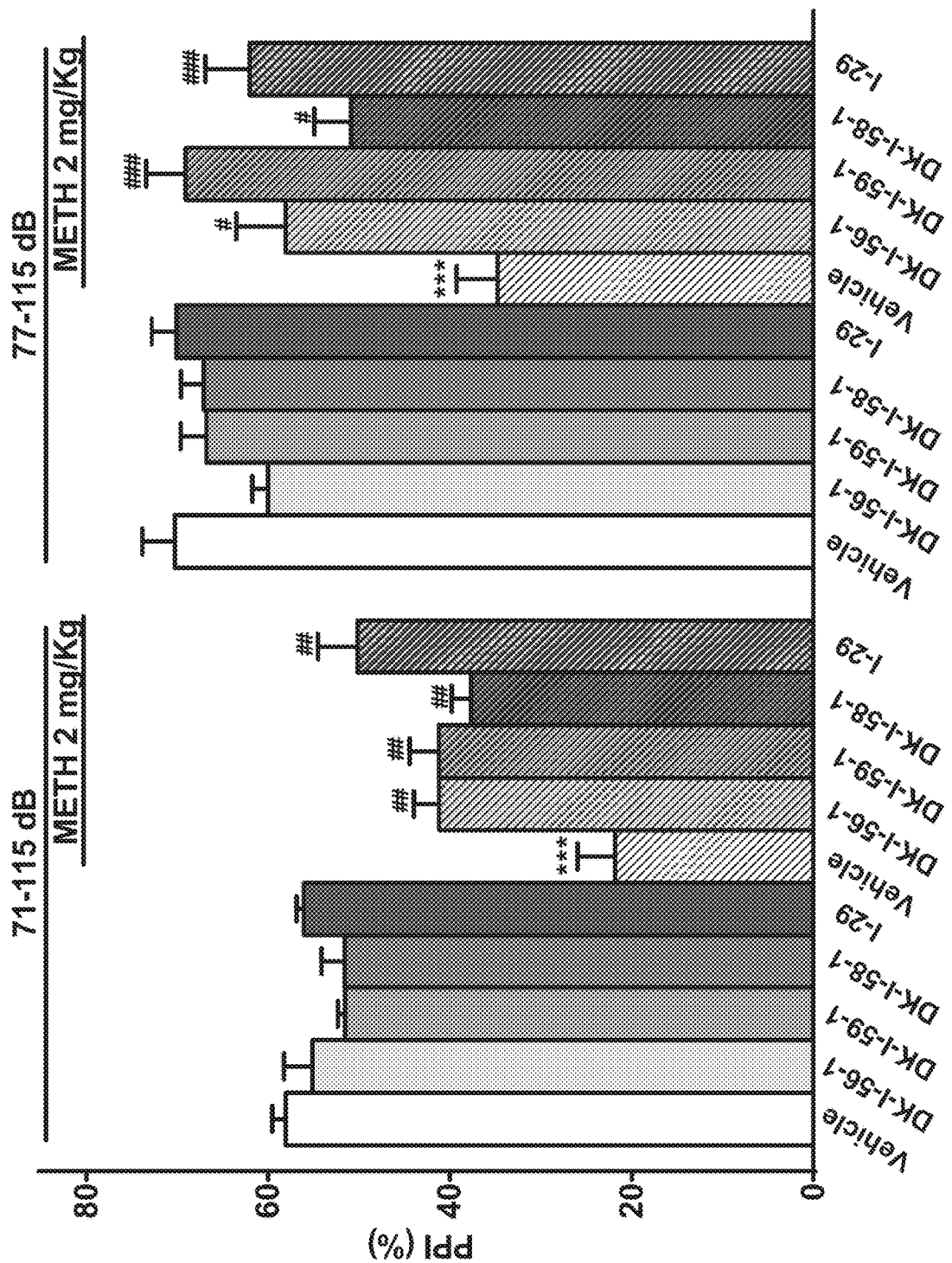
FIG. 6. Effects of I-29 and DK-I-56-1 (—OCD3 derivatives of Compound 6), DK-I-59-1 (a —OCD3 derivative of of LAU 159) and DK-I58-1 (a —OCD3 derivative of of LAU 159) on METH-impaired PPI. The measurement and analyses of PPI impairment are the same as in FIG. 4. ***$p<0.001$ vs. the Vehicle without METH group; #$p<0.05$; ##$p<0.01$, ###$p<0.001$, vs. the Vehicle with METH group.

Compounds according to the present invention, such as but not limited to compound 6 and compound 11, LAU 159 and LAU 463 (see below and data given in FIG. 4) as well as their deuterated derivatives, such as DK-I-56-1, DK-I-59-1 and 1-29 (see below and data given in FIG. 6) are effective in an animal model with sensorimotor gating deficit, reflecting METH-induced PPI impairment.

Temporomandibular Myofascial Pain and Disorders of Trigeminal Nerve

α6 subunits of $GABA_A$Rs are expressed in both neurons and satellite glia of the trigeminal ganglia. The α6 subunit positive neuronal cell bodies in the trigeminal ganglia project axons to the temporomandibular joint and likely to the trigeminal nucleus caudalis and upper cervical region (Vc-C1) and might modulate orofacial pain connected with inflammatory temporomandibular joint nociception, as well as trigeminal neuralgia and neuropathy. Without wishing to be bound by theory, chronic orofacial pain conditions are thought to arise in part (e.g. temporomandibular joint disorders) or completely (disorders of trigeminal nerve) from damage to or pressure on the trigeminal nerve.

Rats with 30% knock down of the α6 subunit of $GABA_A$ receptors in trigeminal ganglia were hypersensitive to TMJ inflammation, measured by a prolonged meal time. This suggests the α6-$GABA_A$ receptor in trigeminal ganglia is important for inhibiting primary sensory afferents in the trigeminal pathway during inflammatory orofacial nociception. The prevalence of TMJ disorders in the United States is estimated at 4,6% and these disorders are the leading cause of chronic orofacial pain.

Moreover, α6-$GABA_A$ receptors may also play an important role in other orofacial pain disorders related to trigeminal ganglia, such as trigeminal neuralgia and trigeminal neuropathic pain. Pain in trigeminal neuralgia is sharp and electric shock-like, with a rapid onset and termination and complete periods of remission lasting weeks to months. Trigeminal neuropathic pain is aching and throbbing, of moderate severity, connected with dental surgery or facial trauma, and continuous in nature. There are unmet needs in the management of trigeminal disorders. Currently, sodium channel blockers such as carbamazepine represent the recommended treatment for trigeminal neuralgia, while there are no accepted on-label pharmacotherapeutic measures for trigeminal neuropathy.

Migraine

Migraine is a complex, disabling disorder of the brain that is characterized by attacks of episodic, periodic paroxysmal attacks of throbbing pain, separated by pain-free intervals associated with nausea, vomiting, and sensory sensitivity to light, sound, and head movement. Migraine is among the most common disorders and remains one of the leading causes of disability. Although there are several anti-migraine drugs, many migraine patients are refractory to the current therapy or intolerable to their side effects. Therefore, a novel treatment for migraine remains an unmet medical need.

Without wishing to be bound by theory, trigemino-vascular activation via both peripheral and central sensitizations is considered by many to be an essential neuropathogenic mechanism of migraine, a severe headache characterized with concurrent nausea, vomiting, and autonomic instability. The trigemino-vascular system (TGVS), consisting of dural and superficial cortical blood vessels which are innervated by unmyelinated trigeminal afferent C fibers and myelinated Ab fibers, is strongly implicated in the initiation of the headache pain. The TGVS transduces peripheral sensory signals, via trigeminal ganglia (TG), to the trigeminal nucleus caudalis (TNC) in the brainstem, which subsequently projects to higher-order pain centers. In addition to TNC, the brain stem trigemino-cervical complex (TCC) also includes superficial laminar neurons of C1/2 spinal dorsal horn neurons which receive nociceptive inputs via dorsal root ganglia (DRG) from C1/2 dorsal roots. Besides, the TNC receives several modulatory inputs from other brain stem nuclei, including the periaqueductal gray (PAG), locus ceruleus (LC), and raphe nucleus (RN).

Central sensitization of the TVGS by TNC activation, which is involved in both nociceptive processing and cerebrovascular regulation, is thought to play a role in migraine pathophysiology. Positron emission tomography showed early brainstem activation in a patient during spontaneous migraine attack but not in the headache-free interval.

Importantly, trigeminal ganglia also send projections to the trigeminal nucleus caudalis (TNC) and upper cervical region (Vc-C1), the trigeminal cervical complex. Activation of the TNC plays an important role in the neuropathogenesis of migraine.

In animal models, TGVS activation can be induced by intra-cisteral (i.c.) instillation of nociceptive substances like capsaicin or autologous blood, resulting in both central and peripheral responses. The central response in the TNC, activated by glutamate released from TG central terminals, can be measured by expressing c-Fos protein, a neuronal activation marker. Peripheral responses, including dural vasodilation and protein extravasation, are neurogenic inflammation phenomena mediated by neuropeptides, such as substance P or calcitonin gene-related peptide (CGRP), released from TG peripheral terminals, i.e. perivascular nerve endings.

Tinnitus

Tinnitus is the perception of sound in the absence of acoustic stimuli. Around 15% of the population develops the condition of chronic tinnitus that requires medical intervention. For about 3% of those suffering from chronic tinnitus, the distressing symptom strongly affects their quality of life. Various drugs have developed for clinical use in treating tinnitus, including lidocaine (antiarrythmics), clonazepam (anxiolytics), gabapentine (anticonculsant), memantine (glutamate rantagonist), and amitriptyline (antidepressant), but they have only limited success.

Without wishing to be bound by theory, it is thought that cochlear damage is linked with a hypothesized neural homeostasis; that is, it argues that neural activity is constantly under homeostatic regulation in order to maintain coding efficiency (or brain functions in general) despite changes in the input environment. In sensory systems, neural pathways are hierarchically organized. Neurons in each level are driven by the activities originated in the preceding lower centers. After cochlear damages, peripheral input is suppressed. Subsequently central regulating mechanisms are activated to maintain neural homeostasis. This manifests itself in the form of elevated central gain, simply to compensate for the weakened input signals. According to this model, the increased central gain accounts well for the physiological tinnitus experienced by nearly 70% of normal population upon sudden entrance into a quiet room. The central gain theoretically can be achieved by adjusting the excitation-inhibition balance in the central circuitry, likely involving the descending auditory pathways. Such deranged excitation-inhibition balance is reflected partly in altered spontaneous neural activities, sound evoked activities and tonotopic reorganization and findings in Fos-immuno-histochemical staining and electrophysiology have also been reported in experimental tinnitus on animals.

Among many central auditory relays which have been implicated in tinnitus, it is thought that the dorsal cochlear nucleus (DCN) plays a role in triggering the tinnitus because it is the first obligatory relay of auditory pathways. Evidence also demonstrated that the decreases of GABA inhibition are related to the elevation in spontaneous and evoked activities at the DCN of loud-noise induced animals. The α6-subunit of the gamma-aminobutyric acid A ($GABA_A$) receptor has been found in the granule cells of dorsal cochlear nucleus. The spontaneous activities of granule cells indicated by Fos immunoreactivities also increased at the DCN in tinnitus animals. Therefore, it is thought that the application of specific agonists of α6-subunit of $GABA_A$ receptor can reduce the enhancement of neural activities indicated by the decrement of spontaneous and sound evoked responses recorded from the dorsal cochlear nucleus and auditory cortex, Fos-immunoreactivities at the DCN, and the tinnitus related behavioral index of pre-pulse inhibition.

Depression

In addition, α6-$GABA_A$ receptors are widely distributed throughout the brain, although with a much lower concentration than that found in the granule cells of cerebellum (Allen brain atlas). It is thought that low abundance receptors exhibit quite specific and important functions in the brain by modulating only those neurons on which they are located.

Since linkage studies indicate that the gene for α6-subunits is associated with female patients with mood disorders, α6-containing receptors might also have some beneficial effects in mood disorders such as depression. Experiments are underway investigating whether compounds in this patent application are able to ameliorate symptoms of depression in several animal models of depression. The planned experiments include the forced swim test and tail suspension tests in C57BL/6N mice, in the design of acute and also repeated (2 weeks) treatment; as well as sucrose preference test and social interaction test in C57BL/6N mice subjected to the model of chronic social defeat stress-induced decrease in these forms of behavior. The elicited changes in behavior mimic depression-like symptoms and could be tried to be prevented by a repeated (2 weeks) treatment with the examined compounds or citalopram used as a positive control.

The following examples further describe the present invention without limitation.

EXAMPLES

Example 1

Synthesis of Compounds

General Procedure A:
Exemplary compounds are shown in FIG. 23.
A substituted aniline (1 mmol) is mixed thoroughly with DEEMM (1 mmol) and heated under argon to 120° C., at which point ethanol is distilled and removed from the reaction vessel. After heating for 2-3 hours and TLC (30% EtOAc in hexanes) shows complete consumption of the starting aniline, diphenyl ether is added and the reaction vessel is heated to 250° C. for 2-3 hours. After complete cyclization to the desired quinoline the reaction vessel is cooled to RT, hexanes are added, and the material is filtered. No further purification is performed on this material.
To the quinoline (1 mmol) is added POCl3 (10 Eq.) and the mixture is stirred at an appropriate temperature to give the chlorinated quinoline. The chlorinated quinoline is further purified by flash column chromatography (20% EtOAc in hexanes) generally giving a white/off-white solid.

The chlorinated quinoline (1 mmol) is mixed with xylene, triethylamine (2.5 mmol), and an appropriate hydrazine hydrochloride salt (1.5 mmol) and heated to reflux for 3-24 hours. When the reaction is complete by TLC (10% MeOH in EtOAc) the mixture is cooled to 0° C., filtered, and washed with copious amounts of water. The solid is then washed with hexanes and allowed to dry. The solid is then recrystallized, generally from a 5:1 mixture of EtOH:water, giving fluffy yellow/orange/red microcrystals of suitable purity for biological testing. Further purification can be accomplished by dissolving the solid in DMSO and slowly adding water and/or dissolving in a basic solution (pH>10) and slowly acidifying to pH<6.

Ethyl-4-hydroxy-7-methoxy (d3) quinolone-3-carboxylate (2). A mixture of (1) (1.26 g, 0.01 m) and diethyl ethoxy methylenemalonate (DEMM) (4.32 g, 0.02 m) in 50 mL diphenyl ether were heated to 120° C. for 1 hr. ethanol formed was distilled off. The solution was then heated to 245-250° C. Heating was continued for 4 hrs. The contents were cooled to room temperature. Hexane 50 mL was added and solids collected by filtration. The compound was washed with ethyl acetate:hexane (2:1) 50 mL and dried. Yield 2.37 g, 95%. Compound is off white and has very poor solubility. The compound was used as such for the further reaction. 1H NMR (300 MHz, DMSO) 12.123 (s, 1H), 8.489 (s, 1H), 8.072-8.040 (d, 1H, J=9.6), 7.018-6.996 (s, 2H), 4.239-4.170 (q, 2H, J=6.9), 1.301-1.254 (t, 3H, J=6.9), 3.876 (s, 3H). 13C (75 MHz, DMSO) 165.29, 162.74, 145.27, 141.24, 127.99, 121.78, 114.63, 100.58, 59.95 and 14.80. HRMS m/z calculated for C13H11D3NO4 251.1111 found 251.1110.

4-chloro-7-methoxy (d3)quinolin-3-carboxylate (3). (2) (2.5 grams, 0.01 m) was heated in neat POCl3 at 80° C. for 2 hours. The excess POCl3 was distilled off under reduced pressure. The residue was dissolved in 25 mL dry dichloromethane and solvent distilled off under reduced pressure. The cycle was repeated for 3 times to drive off all the HCl and POCl3. Due to unstable nature of this compound it was used as such without further purification (2.55 g, 95%). 1H NMR (500 MHz, CDCl3) 9.19 (s, 1H), 8.32-8.30 (d, 1H, J=10.0), 7.48 (s, 1H), 7.36-7.34 (t, 1H), 4.52-4.48 (q, 2H, J=10), 1.301-1.49-1.46 (t, 3H, J=10). 13C (75 MHz, CDCl3) 164.46, 162.87, 151.28, 150.63, 143.94, 126.86, 121.73, 121.36, 120.69, 107.27, 61.95, 55.14 and 14.29. HRMS m/z calculated for C13H10D3ClNO3 269.0772 found 269.0770.

A general procedure for the syntheses of 4. A mixture of 4-chloro-7-methoxy(d3)quinolin-3-carboxylate (3) (0.01 mol, 0.324 g), substituted Phenylhydrazine hydrochloride (0.012 mol) and TEA (0.012 m, 0.12 g) in 40 mL xylene was refluxed for 4 hr. The reaction mixture was cooled to room temperature. The precipitated compound was collected by filtration and purified by crystallization.

Synthesis of LAU159, LAU165, and LAU463

8-Chloro-2-(3-methoxyphenyl)-2H-pyrazolo[4,3-c]quinolin-3(5H)-one (LAU159). In a 8 mL-vial with magnetic stirrer and screw cap, ethyl 4,8-dichloroquinoline-3-carboxylate (135 mg, 0.5 mmol, 1 equiv.), 3-(methoxy)phenyl hydrazine (83 mg, 0.6 mmol, 1.2 equiv.) and triethylamine (61 mg, 0.6 mmol, 1.2 equiv.) were dissolved in dry N,N-dimethylacetamide (3 mL). The reaction mixture was heated to 140° C. for 16 hours. After completion of the reaction evaporation of volatiles and washing of the solid residue with acetone and water afforded the pure product. Yield: 66% (0.33 mmol, 108 mg), Appearance: yellow solid, M.p.: ~340° C., with partial decomposition above 300° C., 1H NMR (200 MHz, DMSO-d6): 12.95 (bs, 1H), 8.72 (d, J=5.2 Hz, 1H), 8.15 (s, 1H), 7.84-7.70 (m, 4H), 7.33 (t, J=8.1 Hz, 1H), 6.75 (d, J=8.1 Hz, 1H), 3.80 (s, 3H). 13C NMR (50 MHz, DMSO-d6): δ=161.5 (s), 159.5 (s), 141.9 (s), 141.0 (s), 139.5 (d), 134.2 (s), 130.6 (s), 130.2 (d), 129.5 (d), 121.6 (d), 121.1 (d), 119.9 (s), 110.9 (d), 109.5 (d), 106.3 (s), 104.4 (d), 55.1 (q). HR-MS: [M+H]+ m/z (predicted)= 326.0691, m/z (measured)=326.0688, difference=−0.92 ppm.

8-Chloro-2-(2-methoxyphenyl)-2H-pyrazolo[4,3-c]quinolin-3(5H)-one (LAU165). In an 8 mL-vial with magnetic stirrer and screw cap, ethyl 4,6-dichloroquinoline-3-carboxylate (135 mg, 0.5 mmol, 1 equiv), 2-methoxyphenylhydrazine (83 mg, 0.6 mmol, 1.2 equiv) and triethylamine (63 mg, 0.6 mmol, 1.2 equiv) were dissolved in dry N,N-dimethylacetamide (3 mL). The reaction mixture was heated to 140° C. for 16 hours. After completion of the reaction the reaction mixture was evaporated to dryness. The crude product was purified by flash-column chromatography (45 g silica 60, eluent EtOAc/MeOH 5%) Co-eluting triethylamine hydrochloride was subsequently removed by washing with water. Yield: 28% (0.14 mmol, 46 mg) (28%). Appearance: yellow solid. TLC: 0.07 (EtOAc/MeOH 10%). M.p. 310-313° C. with partial decomposition. 1H-NMR (200 MHz, DMSO-d$_6$) δ=3.73 (s, 3H), 7.03 (t, J=7.5 Hz, 1H), 7.16 (d, J=8.2 Hz, 1H), 7.29-7.45 (m, 2H), 7.62-7.73 (m, 2H), 8.01 (d, J=1.6 Hz, 1H), 8.65 (s, 1H), 12.78 (s, 1H). 13C-NMR (50 MHz, DMSO-d$_6$) δ=55.6 (q), 105.3 (s), 112.5 (d), 120.2 (d), 120.3 (s), 120.9 (d), 121.4 (d), 127.7 (s), 129.3 (d), 129.4 (d), 129.7 (d), 130.3 (s), 134.0 (s), 139.1 (d), 141.4 (s), 155.1 (s), 161.6 (s). HR-ESI-MS: m/z 326.0678 [M+H]+(calcd 326.0691, diff +3.99 ppm)

7-Bromo-2-(4-methoxyphenyl)-2H-pyrazolo[4,3-c]quinolin-3(5H)-one (LAU463). Ethyl 7-bromo-4-chloroquinoline-3-carboxylate (200 mg, 0.64 mmol, 1 equiv.) and (4-methoxyphenyl)hydrazine (110 mg, 0.80 mmol, 1.2 equiv.) were dissolved in 5 mL dimethylacetamide. The reaction was carefully purged with argon several times, triethylamine (1 equiv.) was added and the reaction was heated to 140° C. for 24 hours. The solvent was removed via Kugelrohr distillation of the crude mixture. Washing of the residue with acetone gave the product as an orange-yellow solid. Yield: 51% (0.33 mmol, 121 mg), Appearance: orange-yellow solid, TLC: 0.45 (EtOAc/MeOH 20%), M.p.: >330° C., 1H NMR (400 MHz, DMSO-d6) δ 12.78 (s, 1H), 8.74 (d, J=5.8 Hz, 1H), 8.13 (d, J=8.5 Hz, 1H), 8.06 (d, J=8.6 Hz, 2H), 7.89 (d, J=2.0 Hz, 1H), 7.69 (dd, J=8.5, 2.0 Hz, 1H), 7.02 (d, J=8.6 Hz, 2H), 3.79 (s, 3H). 13C NMR (101 MHz, DMSO) δ 161.3 (s), 156.5 (s), 142.4 (s), 140.1 (d), 136.9 (s), 133.8 (s), 129.7 (d), 124.5 (d), 123.0 (s), 122.2 (d), 120.9 (d), 118.2 (s), 114.3 (d), 107.2 (s), 55.7 (q)

7-Methoxy-2-(pyrazin-2-yl)-2,5-dihydro-3H-pyrazolo[4,3-c]quinolin-3-one (DCBS126). In a 8 mL vial with magnetic stirrer and screw cap, ethyl 4-chloro-7-methoxyquinoline-3-carboxylate (70 mg, 0.26 mmol, 1 equiv.) and 2-hydrazinopyrazine (32 mg, 0.29 mmol, 1.1 equiv.) were dispersed in 1.5 mL ethanol, triethylamine (40 µL, 0.29 mmol, 1.1 eq.) was added and the reaction mixture was heated to reflux under argon atmosphere. After 20 h the reaction mixture was rinsed with 4 mL water, filtered and the precipitate was washed with 15 mL EtOAc/PE (1/1). The yellow solid was dried under reduced pressure to give the desired product. Yield: 58% (0.15 mmol, 45 mg), Appearance: yellow solid, TLC: 0.38 (10% MeOH in CH2Cl2), M.p.: >300° C., 1H NMR (400 MHz, DMSO-d6) δ 3.88 (s, 3H), 7.16-7.23 (m, 2H), 8.13 (dd, J=8.5, 0.8 Hz, 1H), 8.44 (d, J=2.5 Hz, 1H), 8.56 (dd, J=2.5, 1.5 Hz, 1H), 8.75 (s, 1H), 9.51 (d, J=1.4 Hz, 1H), 12.74 (br s, 1H). 13C NMR (101 MHz, DMSO-d6) δ 55.6 (q), 102.1 (d), 105.0 (s), 112.2 (s), 115.5 (d), 123.9 (d), 136.6 (d), 137.3 (s), 140.0 (d), 140.1 (d), 142.8 (d), 144.9 (s), 148.0 (s), 160.8 (s), 162.4 (s). HR-MS: Calc. [M+H]+ m/z (predicted)=294.0992, m/z (measured)=294.0992, difference=0.00 ppm.

N-(4-Hydroxyphenyl)acetamide [DK-I-2-1]. To a mixture of 4-aminophenol (50.0 g, 458.2 mmol) and tetrahydrofuran (200 mL) acetic anhydride (49.1 g, 481.1 mmol) was added dropwise over 30 min while keeping the temperature below 50° C. The reaction mixture was then stirred for 30 min at 50° C. and then cooled to rt. The reaction mixture was then diluted with hexanes (200 mL) to precipitate the product. After stirring for 1 h, the solid product was filtered and washed twice with hexanes (50 mL×2). The solid was dried to afford the product as a white crystalline solid DK-I-2-1 (62.7 g, 90.0%): mp 170-171° C.; $^1$H NMR (300 MHz, DMSO) δ 9.64 (s, 1H), 9.13 (s, 1H), 7.34 (d, J=8.8 Hz, 2H), 6.67 (d, J=8.8 Hz, 2H), 1.98 (s, 3H); $^{13}$C NMR (75 MHz, DMSO) δ 167.95, 153.57, 131.49, 121.26, 115.44, 24.19; HRMS m/z calculated for C8H10NO2 (M+H)+152.0711 found 152.15.

N-(3-Hydroxyphenyl)acetamide [DK-I-3-1]. To a mixture of 3-aminophenol (25.0 g, 229.1 mmol) and tetrahydrofuran (100 mL) acetic anhydride (24.5 g, 240.5 mmol) was added dropwise over 30 min while keeping the temperature below 50° C. The reaction mixture was then stirred for 30 min at 50° C. and then cooled to room temperature. The reaction mixture was then diluted with hexanes (100 mL) to precipitate the product. After stirring for 1 h, the solid product was filtered and washed twice with hexanes (25 mL×2). The solid was dried to afford the product as a white crystalline solid DK-I-3-1 (33.2 g, 96.0%): mp 145-148° C.; $^1$H NMR (300 MHz, DMSO) δ 9.77 (s, 1H), 9.32 (s, 1H), 7.18 (s, 1H), 7.04 (t, J=8.0 Hz, 1H), 6.92 (d, J=8.1 Hz, 1H), 6.42 (dd, J=7.9, 2.1 Hz, 1H), 2.01 (s, 3H); $^{13}$C NMR (75 MHz, DMSO) δ 168.60, 158.01, 140.81, 129.72, 110.55, 110.18, 106.60, 24.50; HRMS m/z calculated for C8H10NO2 (M+H)$^+$ 152.0711 found 152.15.

N-(2-Hydroxyphenyl)acetamide [DK-I-30-1]. To a mixture of 2-aminophenol (25.0 g, 229.1 mmol) and tetrahydrofuran (100 mL) acetic anhydride (24.5 g, 240.5, mmol) was added dropwise over 30 min while keeping the temperature below 50° C. The reaction mixture was then stirred for 30 min at 50° C. and then cooled to rt. The reaction mixture was then diluted with hexanes (100 mL) to precipitate the product. After stirring for 1 h, the solid product was filtered and washed twice with hexanes (25 mL×2). The solid was dried to afford the product as a light brown solid DK-I-30-1 (33.1 g, 95.7%): mp 211-213° C.; $^1$H NMR (300 MHz, DMSO) δ 9.75 (s, 1H), 9.31 (s, 1H), 7.67 (d, J=7.7 Hz, 1H), 6.85 (ddd, J=33.6, 14.6, 7.2 Hz, 3H), 2.10 (s, 3H); $^{13}$C NMR (75 MHz, DMSO) δ 169.44, 148.34, 126.88, 125.08, 122.80, 119.40, 116.38, 24.05; HRMS m/z calculated for C8H10NO2 (M+H)+152.0711 found 152.15.

N-(4-Methoxy-d3-phenyl)acetamide [DK-I-6-1]. To a mixture of N-(4-hydroxyphenyl)acetamide DK-I-2-1 (62.0 g, 410.1 mmol), potassium carbonate (113.4 g, 615.2 mmol) and acetone (230 mL) methyl iodide (D3) (100 g, 689.8 mmol) was added dropwise over 30 min. The reaction mixture was then stirred for 24 h at 20-25° C. The reaction mixture was then diluted with ethyl acetate (300 mL) and water (300 mL). The resulting biphasic mixture was allowed to stand for 15 min and the layers were separated. The aqueous layer was extracted with ethyl acetate (200 mL) and then the combined organic layers were washed with 10% potassium carbonate solution (200 mL). The organic layer was then dried over magnesium sulfate. The solvents were then removed by evaporation on a rotovap and the product residue was slurried with hexanes (200 mL). The solid product was then filtered and washed twice with hexanes (50 mL×2). The solid was dried to afford the product as an off-white solid DK-I-6-1 (71.7 g, 99%): mp 125-126° C.; $^1$H NMR (300 MHz, DMSO) δ 9.77 (s, 1H), 7.48 (d, J=9.0 Hz, 2H), 6.85 (d, J=9.0 Hz, 2H), 3.38 (s, 3H), 2.00 (s, 3H); $^{13}$C NMR (75 MHz, DMSO) δ 168.20, 155.48, 132.94, 121.01, 114.21, 24.23; HRMS m/z calculated for C9H9D3NO2 (M+H)$^+$ 169.1054 found 169.20.

N-(3-Methoxy-d3-phenyl)acetamide [DK-I-8-1]. To a mixture of N-(3-hydroxyphenyl)acetamide DK-I-3-1 (35.0 g, 231.5 mmol), potassium carbonate (64.0 g, 463.1 mmol) and acetone (140 mL) methyl iodide (D3) (50.3 g, 347.3 mmol) was added dropwise over 30 min. The reaction mixture was then stirred for 24 h at 20-25° C. The reaction mixture was then diluted with ethyl acetate (150 mL) and water (150 mL). The resulting biphasic mixture was allowed to stand for 15 min and the layers were separated. The aqueous layer was extracted with ethyl acetate (100 mL) and then the combined organic layers were washed with 10% potassium carbonate solution (100 mL). The organic layer was then dried over magnesium sulfate. The solvents were then removed by evaporation on a rotovap and the product residue was slurried with hexanes (100 mL). The solid product was then filtered and washed twice with hexanes (50 mL×2). The solid was dried to afford the product as an off-white solid DK-I-8-1 (38.9 g, 99%): mp 89-91° C.; $^1$H NMR (300 MHz, DMSO) δ 9.89 (s, 1H), 7.27 (s, 1H), 7.18 (t, J=8.1 Hz, 1H), 7.10 (d, J=8.2 Hz, 1H), 6.60 (dd, J=7.8, 2.0 Hz, 1H), 2.03 (s, 3H); $^{13}$C NMR (75 MHz, DMSO) δ 168.76, 159.93, 140.96, 129.89, 111.71, 108.76, 105.30, 24.53; HRMS m/z calculated for C9H9D3NO2 (M+H)+ 169.1054 found 169.15.

N-(2-Methoxy-d3-phenyl)acetamide [DK-I-31-1]. To a mixture of N-(2-hydroxyphenyl)acetamide DK-I-30-1 (30.0 g, 198.5 mmol), potassium carbonate (54.9 g, 396.9 mmol) and acetone (140 mL) methyl iodide (D3) (50.3 g, 347.3 mmol) was added dropwise over 30 min. The reaction mixture was then stirred for 24 h at 20-25° C. The reaction mixture was then diluted with ethyl acetate (150 mL) and water (150 mL). The resulting biphasic mixture was allowed to stand for 15 min and the layers were separated. The aqueous layer was extracted with ethyl acetate (100 mL) and then the combined organic layers were washed with 10% potassium carbonate solution (100 mL). The organic layer was then dried over magnesium sulfate. The solvents were then removed by evaporation on a rotovap and the product residue was slurried with hexanes (100 mL). The solid product was then filtered and washed twice with hexanes (50 mL×2). The solid was dried to afford the product as an off-white solid DK-I-31-1 (31.9 g, 99%): mp 82-83° C.; $^1$H NMR (300 MHz, DMSO) δ 9.10 (s, 1H), 7.93 (d, J=7.8 Hz, 1H), 7.22-6.97 (m, 2H), 6.97-6.79 (m, 1H), 2.08 (s, 3H); $^{13}$C NMR (75 MHz, DMSO) δ 168.87, 149.98, 127.87, 124.63, 122.45, 120.57, 111.50, 24.30; HRMS m/z calculated for C9H9D3NO2 (M+H)$^+$ 169.1054 found 169.15.

4-Methoxy-d3-aniline [DK-I-67-1]. A mixture of N-(4-methoxy-d3-phenyl)acetamide DK-I-6-1 (20.0 g, 118.9 mmol), 12 M hydrochloric acid (20 mL, 240 mmol), and water (60 mL) was heated at 90-95° C. for 2 h. The reaction mixture was then cooled to 20-25° C. and the pH was adjusted to 14 with a solution of sodium hydroxide (20 g, 500 mmol) and water (20 mL). The product was then extracted from the aqueous layer four times with dichloromethane (50 mL×4). The combined organic layers were then dried over magnesium sulfate. Evaporation of the solvents on a rotovap afforded the product as a dark orange oil DK-I-67-1 (14.4 g, 96%): $^1$H NMR (300 MHz, DMSO) δ 5.75-5.62 (m, 2H), 5.62-5.47 (m, 2H), 3.50 (s, 2H); $^{13}$C NMR (75 MHz, DMSO) δ 150.34, 141.51, 114.62, 113.89; HRMS m/z calculated for C7H7D3NO (M+H)+127.0948 found 127.25.

3-Methoxy-d3-aniline [DK-I-41-1]. A mixture of N-(3-methoxy-d3-phenyl)acetamide DK-I-8-1 (20.0 g, 118.9 mmol), 12 M hydrochloric acid (20 mL, 240 mmol), and water (60 mL) was heated at 90-95° C. for 2 h. The reaction mixture was then cooled to 20-25° C. and the pH was adjusted to 14 with a solution of sodium hydroxide (20 g, 500 mmol) and water (20 mL). The product was then extracted from the aqueous layer four times with dichloromethane (50 mL×4). The combined organic layers were then dried over magnesium sulfate. Evaporation of the solvents on a rotovap afforded the product as a golden yellow oil DK-I-41-1 (13.5 g, 90%): $^1$H NMR (300 MHz, CDCl$_3$) δ 7.10 (t, J=8.0 Hz, 1H), 6.35 (dddd, J=11.9, 11.2, 3.4, 2.0 Hz, 3H), 4.00 (s, 2H); $^{13}$C NMR (75 MHz, CDCl$_3$) δ 160.78, 147.54, 130.16, 108.14, 104.22, 101.28; HRMS m/z calculated for C7H6D3NO (M+H)+127.0948 found 127.25.

Ethyl-6-chloro-4-hydroxyquinoline-3-carboxylate [DK-I-34-1]. A mixture of 4-chloroaniline (45.5 g, 356.7 mmol), diethyl ethoxymethylenemalonate (80.9 g, 374.1 mmol) and diphenyl ether (200 mL) was slowly heated to 230° C. The evolved ethanol was collected in a Dean-Stark trap. Once the ethanol formation ceased, the reaction mixture was heated for an additional 30 min at 230° C. The reaction mixture was then cooled to 80° C. and diluted with ethanol (200 mL). Upon cooling to 20-25° C. the solid product was collected by filtration and washed twice with ethanol (50 mL×2) and twice with hexanes (50 mL×2). The solid was dried to afford the product as an off-white crystalline solid DK-I-34-1 (85.1 g, 95%): $^1$H NMR (300 MHz, TFA) δ 11.66 (s, 1H), 9.32 (d, J=4.5 Hz, 1H), 8.62 (d, J=2.5 Hz, 1H), 8.12 (d, J=13.0 Hz, 2H), 4.82-4.55 (m, 2H), 1.53 (dd, J=11.8, 7.0 Hz, 3H); $^{13}$C NMR (75 MHz, TFA) δ 172.51, 167.19, 144.95, 138.35, 137.62, 137.58, 123.58, 121.35, 120.82, 105.30, 64.70, 11.96; HRMS m/z calculated for C12H11ClNO3 (M+H)+ 252.0427 found 252.10.

Ethyl-4-hydroxy-7-methoxyquinoline-3-carboxylate [DK-I-39-1]. A mixture of 3-methoxyaniline (50.0 g, 406.0 mmol), diethyl ethoxymethylenemalonate (87.8 g, 406.0 mmol) and diphenyl ether (200 mL) was slowly heated to 230° C. The evolved ethanol was collected in a Dean-Stark trap. Once the ethanol formation ceased, the reaction mixture was heated for an additional 30 min at 230° C. The reaction mixture was then cooled to 80° C. and diluted with ethanol (200 mL). Upon cooling to 20-25° C. the solid product was collected by filtration and washed twice with ethanol (50 mL×2) and twice with hexanes (50 mL×2). The solid was dried to afford the product as a light brown solid DK-I-39-1 (37.1 g, 37%): $^1$H NMR (300 MHz, TFA) δ 11.63 (s, 1H), 9.22 (d, J=6.3 Hz, 1H), 8.56 (dd, J=9.1, 6.7 Hz, 1H), 7.66-7.54 (m, 1H), 7.47 (d, J=4.2 Hz, 1H), 4.69 (dd, J=13.8, 6.9 Hz, 2H), 4.13 (d, J=6.4 Hz, 3H), 1.57 (q, J=6.8 Hz, 3H); $^{13}$C NMR (75 MHz, TFA) δ 171.88, 167.91, 167.62, 144.49, 142.43, 126.28, 121.92, 114.05, 103.81, 99.24, 64.28, 55.45, 12.00; HRMS m/z calculated for C13H14NO4 (M+H)+ 248.0923 found 248.15.

Ethyl-7-bromo-4-hydroxyquinoline-3-carboxylate [DK-I-49-1]. A mixture of 3-bromoaniline (8.7 g, 58.1 mmol), diethyl ethoxymethylenemalonate (10.9 g, 58.1 mmol) and diphenyl ether (40 mL) was slowly heated to 230° C. The evolved ethanol was collected in a Dean-Stark trap. Once the ethanol formation ceased, the reaction mixture was heated for an additional 30 min at 230° C. The reaction mixture was then cooled to 80° C. and diluted with ethanol (40 mL). Upon cooling to 20-25° C. the solid product was collected by filtration and washed twice with ethanol (10 mL×2) and twice with hexanes (10 mL×2). The solid was dried to afford the product as a light brown solid DK-I-49-1 (11.5 g, 77%): $^1$H NMR (300 MHz, TFA) δ 11.64 (s, 1H), 9.38 (s, 1H), 8.57 (d, J=8.9 Hz, 1H), 8.43 (s, 1H), 8.15 (d, J=8.9 Hz, 1H), 4.75 (q, J=7.1 Hz, 2H), 1.60 (t, J=7.2 Hz, 3H); $^{13}$C NMR (75 MHz, TFA) δ 173.48, 167.33, 145.75, 139.71, 134.19, 134.06, 125.60, 122.70, 118.57, 105.08, 64.74, 12.01; HRMS m/z calculated for C12H10BrNO3 (M+H)+ 295.9922 found 296.05.

Ethyl-4-hydroxy-7-methoxy-d3-quinoline-3-carboxylate [DK-I-54-1]. A mixture of 3-methoxy-d3-aniline DK-I-41-1 (10 g, 81.2 mmol), diethyl ethoxymethylenemalonate (21.1 g, 97.4 mmol) and diphenyl ether (100 mL) was slowly heated to 230° C. The evolved ethanol was collected in a Dean-Stark trap. Once the ethanol formation ceased, the reaction mixture was heated for an additional 30 min at 230° C. The reaction mixture was then cooled to 80° C. and diluted with hexanes (100 mL). Upon cooling to 20-25° C. the solid product was collected by filtration and washed twice with hexanes (50 mL×2). The solid was dried to afford the product as a brown solid DK-I-54-1 (13.0 g, 64%): $^1$H NMR (300 MHz, TFA) δ 11.64 (s, 1H), 9.23 (s, 1H), 8.57 (d, J=9.3 Hz, 1H), 7.59 (dd, J=9.4, 2.3 Hz, 1H), 7.48 (d, J=2.2 Hz, 1H), 4.71 (q, J=7.2 Hz, 2H), 1.58 (t, J=7.2 Hz, 3H); $^{13}$C NMR (75 MHz, TFA) δ 171.89, 167.92, 167.64, 144.50, 142.44, 126.28, 121.93, 114.05, 103.81, 99.25, 64.29, 12.01; HRMS m/z calculated for C13H11D3NO4 (M+H)$^+$ 251.1109 found 251.20.

Ethyl-4-hydroxy-6-methoxy-d3-quinoline-3-carboxylate [DK-I-70-1]. A mixture of 4-methoxy-d3-aniline DK-I-67-1 (10 g, 81.2 mmol), diethyl ethoxymethylenemalonate (21.1 g, 97.4 mmol) and diphenyl ether (100 mL) was slowly heated to 230° C. The evolved ethanol was collected in a Dean-Stark trap. Once the ethanol formation ceased, the reaction mixture was heated for an additional 30 min at 230° C. The reaction mixture was then cooled to 80° C. and diluted with hexanes (100 mL). Upon cooling to 20-25° C. the solid product was collected by filtration and washed twice with hexanes (50 mL×2). The solid was dried to afford the product as a light brown solid DK-I-70-1 (9.9 g, 49%). $^1$H NMR (300 MHz, TFA) δ 11.66 (s, 1H), 9.15 (s, 1H), 8.05 (d, J=9.2 Hz, 1H), 7.97-7.74 (m, 2H), 4.67 (q, J=7.1 Hz, 2H), 1.67-1.39 (m, 3H); $^{13}$C NMR (75 MHz, TFA) δ 171.68, 167.54, 160.89, 141.86, 134.62, 129.91, 121.73, 121.28, 104.58, 102.17, 64.41, 11.97; HRMS m/z calculated for C13H11D3NO4 (M+H)+251.1109 found 251.20.

Ethyl 6-bromo-8-fluoro-4-hydroxyquinoline-3-carboxylate [MM-I-01]. 3-Bromo-5-fluoroaniline (10 g, 52.6 mmol) was heated with diethyl ethoxymethylene malonate (11.2 mL, 55.3 mmol) at 125° C. After heating for 2 h, downtherm A (50 mL) was added and the mixture was heated up to 255° C. for more 2 h. The reaction was brought to room temperature and diluted with hexane (50 mL). The mixture was stirred for 5 min. The precipitate was filtered and washed with hexane to yield the product as a brown colored solid MM-I-01 (13.60 g, 82%): mp 285-286° C.; 1H NMR (300 MHz, DMSO) δ 12.65 (s, 1H; H-11), 8.40 (s, 1H; H-8), 8.04 (s, 1H; H-6), 8.00 (dd, J=10.1, 2.0 Hz, 1H; H-2), 4.23 (q, J=7.1 Hz, 2H; H-18), 1.28 (t, J=7.1 Hz, 3H; H-17); HRMS m/z calculated for C12H9NO3FBr 313.9823 found 313.9833.

Ethyl 4-hydroxy-7-(trifluoromethyl)quinoline-3-carboxylate [MM-I-04]. 3-(Trifluoromethyl)aniline (10 g, 62.1 mmol) was heated with diethyl ethoxymethylene malonate (12.6 mL, 62 mmol) at 125° C. for 1 h. Then, downtherm A (50 mL) was added and the mixture was heated up to 255° C. for 2.5 h. After heating, the reaction was brought to room temperature and diluted with hexane (50 mL). The mixture was stirred for 5 min. The precipitated was filtered and washed with hexane to provide the product as a white colored solid MM-I-04 (16.51 g, 93%): mp 340-341° C.; 1H NMR (300 MHz, DMSO) δ 12.51 (s, 1H; H-11), 8.70 (s, 1H; H-8), 8.35 (d, J=8.3 Hz, 1H; H-6), 8.00 (s, 1H; H-3), 7.72 (d, J=8.1 Hz, 1H; H-1), 4.24 (q, J=14.3, 7.1 Hz, 2H; H-20), 1.29 (t, J=7.0 Hz, 3H; H-19); HRMS m/z calculated for C13H10NO3F3 286.0686 found 286.0691.

Ethyl-4,6-dichloroquinoline-3-carboxylate [DK-I-35-1]. A mixture of ethyl-6-chloro-4-hydroxyquinoline-3-carboxylate DK-I-34-1 (85.1 g, 338.1 mmol), N,N-dimethylformamide (1.0 mL, 12.9 mmol), and dichloromethane (640 mL) was heated to 35-40° C. Oxalyl chloride (47.2 g, 371.9 mmol) was added dropwise to the reaction mixture over 30 min. The reaction mixture was then heated for 6 h at reflux (38-40° C.). The resulting pale yellow solution was then cooled to 20-25° C. The reaction mixture was then neutralized by slowly adding a 25% solution of potassium carbonate (75 g) in water (300 mL). The layers were then separated and the aqueous layers extracted with dichloromethane (200 mL). The combined organic layers were then washed with a 25% solution of potassium carbonate (50 g) in water (200 mL). The combined organic layers were then dried over magnesium sulfate. The solvents were then removed by evaporation on a rotovap and the product residue was slurried with hexanes (200 mL). The solid product was then filtered and washed twice with hexanes (50 mL×2). The solid was dried to afford the product as an off-white solid DK-I-35-1 (81.9 g, 90%): $^1$H NMR (300 MHz, DMSO) δ 9.13 (s, 1H), 8.30 (d, J=2.2 Hz, 1H), 8.14 (d, J=9.0 Hz, 1H), 7.97 (dd, J=9.0, 2.3 Hz, 1H), 4.44 (q, J=7.1 Hz, 2H), 1.39 (t, J=7.1 Hz, 3H); $^{13}$C NMR (75 MHz, DMSO) δ 164.01, 150.53, 147.73, 141.04, 134.30, 133.34, 132.20, 126.53, 124.37, 124.08, 62.59; HRMS m/z calculated for C12H10C12NO2 (M+H)+270.0088 found 270.10.

Ethyl-4-chloro-7-methoxyquinoline-3-carboxylate [DK-I-40-1]. A mixture of ethyl-4-hydroxy-7-methoxyquinoline-3-carboxylate DK-I-39-1 (37.1 g, 150.0 mmol), N,N-dimethylformamide (0.5 mL, 6.5 mmol), and dichloromethane (150 mL) was heated to 35-40° C. Oxalyl chloride (20.9 g, 165.0 mmol) was added dropwise to the reaction mixture over 30 min. The reaction mixture was then heated for 2 h at reflux (38-40° C.). The resulting brown solution was then cooled to 20-25° C. The reaction mixture was diluted with dichloromethane (150 mL) and then neutralized by slowly adding a 25% solution of potassium carbonate (75 g) in water (300 mL). The layers were then separated and the aqueous layers extracted with dichloromethane (100 mL). The combined organic layers were then washed with a 25% solution of potassium carbonate (75 g) in water (300 mL). The combined organic layers were then dried over magnesium sulfate. The solvents were then removed by evaporation on a rotovap and the product residue was slurried with hexanes (200 mL). The solid product was then filtered and washed twice with hexanes (50 mL×2). The solid was dried to afford the product as an off-white solid DK-I-40-1 (36.3 g, 91%): $^1$H NMR (300 MHz, DMSO) δ 9.08 (s, 1H), 8.25 (d, J=9.2 Hz, 1H), 7.57-7.37 (m, 2H), 4.41 (q, J=7.1 Hz, 2H), 3.98 (s, 3H), 1.38 (t, J=7.1 Hz, 3H); $^{13}$C NMR (75 MHz, DMSO) δ 164.32, 162.83, 151.62, 150.81, 142.02, 126.85, 122.12, 121.11, 120.56, 108.36, 62.15, 56.45, 14.49; HRMS m/z calculated for C13H13ClNO3 (M+H)+266.0584 found 266.15.

Ethyl-7-bromo-4-chloroquinoline-3-carboxylate [DK-I-54-1]. A mixture of ethyl-7-bromo-4-hydroxyquinoline-3-carboxylate DK-I-49-1 (11.0 g, 37.1 mmol), N,N-dimethylformamide (0.1 mL, 1.3 mmol), and dichloromethane (50 mL) was heated to 35-40° C. Oxalyl chloride (5.2 g, 40.9 mmol) was added dropwise to the reaction mixture over 30 min. The reaction mixture was then heated for 1 h at reflux (38-40° C.). The resulting brown solution was then cooled to 20-25° C. The reaction mixture was diluted with dichloromethane (150 mL) and then neutralized by slowly adding a 25% solution of potassium carbonate (12.5 g) in water (50 mL). The layers were then separated and the aqueous layers extracted with dichloromethane (50 mL). The combined organic layers were then washed with a 25% solution of potassium carbonate (12.5 g) in water (50 mL). The combined organic layers were then dried over magnesium sulfate. The solvents were then removed by evaporation on a rotovap and the product residue was slurried with hexanes (50 mL). The solid product was then filtered and washed twice with hexanes (25 mL×2). The solid was dried to afford the product as an off-white solid DK-I-54-1 (7.2 g, 61%): $^1$H NMR (300 MHz, DMSO) δ 9.15 (s, 1H), 8.36 (d, J=1.9 Hz, 1H), 8.28 (d, J=9.0 Hz, 1H), 7.98 (dd, J=9.0, 1.9 Hz, 1H), 4.44 (q, J=7.1 Hz, 2H), 1.39 (t, J=7.1 Hz, 3H); $^{13}$C NMR (75 MHz, DMSO) δ 164.04, 151.40, 149.74, 142.34, 132.67, 131.88, 127.50, 126.64, 124.70, 123.96, 62.55, 14.46; HRMS m/z calculated for C12H10BrClNO2 (M+H)+ 313.9583 found 314.05.

Ethyl-4-chloro-7-methoxy-d3-quinoline-3-carboxylate [DK-I-57-1]. A mixture of ethyl-4-hydroxy-7-methoxy-d3-quinoline-3-carboxylate DK-I-54-1 (13.0 g, 51.9 mmol), phosphorus oxychloride (8.8 g, 57.1 mmol) and toluene (52 mL) was heated to 80-90° C. The reaction mixture was then held for 1 h at 80-90° C.). The resulting brown solution was then cooled to 20-25° C. The reaction mixture was then diluted with hexanes (50 mL). The solids were collected by filtration and washed twice with hexanes (50 mL each). The solids were then dissolved in dichloromethane (100 mL) and then neutralized by slowly adding a 25% solution of potassium carbonate (12.5 g) in water (50 mL). The layers were then separated and the aqueous layers extracted with dichloromethane (50 mL). The combined organic layers were then washed with a 25% solution of potassium carbonate (12.5 g) in water (50 mL). The combined organic layers were then dried over magnesium sulfate. The solvents were then removed by evaporation on a rotovap and the product residue was slurried with hexanes (50 mL). The solid product was then filtered and washed twice with hexanes (25 mL×2). The solid was dried to afford the product as an off-white solid DK-I-57-1 (11.5 g, 82%): $^1$H NMR (300 MHz, DMSO) δ 9.07 (s, 1H), 8.23 (d, J=9.2 Hz, 1H), 7.54-7.38 (m, 2H), 4.40 (q, J=7.1 Hz, 2H), 1.37 (t, J=7.1 Hz, 3H); $^{13}$C NMR (75 MHz, DMSO) δ 164.29, 162.85, 151.53, 150.75, 142.41, 126.84, 122.11, 121.07, 120.56, 108.27, 62.15, 14.49; HRMS m/z calculated for C13H10D3ClNO3 (M+H)+269.0770 found 269.15.

Ethyl-4-chloro-6-methoxy-d3-quinoline-3-carboxylate [DK-I-73-2]. A mixture of ethyl-4-hydroxy-6-methoxy-d3-quinoline-3-carboxylate DK-I-70-1 (10.0 g, 40.0 mmol), phosphorus oxychloride (6.7 g, 44.0 mmol) and toluene (40 mL) was heated to 80-90° C. The reaction mixture was then held for 1 h at 80-90° C.). The resulting brown solution was then cooled to 20-25° C. The reaction mixture was then diluted with hexanes (40 mL). The solids were collected by filtration and washed twice with hexanes (20 mL each). The solids were then dissolved in dichloromethane (100 mL) and then neutralized by slowly adding a 25% solution of potassium carbonate (10 g) in water (40 mL). The layers were then separated and the aqueous layers extracted with dichloromethane (50 mL). The combined organic layers were then washed with a 25% solution of potassium carbonate (10 g) in water (40 mL). The combined organic layers were then dried over magnesium sulfate. The solvents were then removed by evaporation on a rotovap and the product residue was slurried with hexanes (50 mL). The solid product was then filtered and washed twice with hexanes (25 mL×2). The solid was dried to afford the product as an off-white solid DK-I-73-2 (8.5 g, 79%): $^1$H NMR (300 MHz, DMSO) δ 8.95 (s, 1H), 8.03 (d, J=9.1 Hz, 1H), 7.67-7.45 (m, 2H), 4.42 (q, J=7.1 Hz, 2H), 1.38 (t, J=7.1 Hz, 3H); $^{13}$C NMR (75 MHz, DMSO) δ 164.49, 159.57, 147.25, 145.36, 139.99, 131.67, 126.91, 125.20, 123.87, 102.96, 62.36, 14.47; HRMS m/z calculated for C13H10D3ClNO3 (M+H)+269.0770 found 269.15.

Ethyl 6-bromo-4-chloro-8-fluoroquinoline-3-carboxylate [MM-I-02]. The Ethyl 6-bromo-8-fluoro-4-hydroxyquinoline-3-carboxylate MM-I-01 (1 g, 3.2 mmol) was placed in a flask with POCl3 (4 mL). The mixture was heated at 70° C. for 3 h. The excess of POCl3 was evaporated by reduced pressure and the remaining oil was quenched with saturated solution of NaHCO$_3$. Then, the aqueous solution was extracted with CH2Cl2 (3×50 mL) and the combined organic layers were dried (Na2SO4). The solvent was removed under reduce pressure and the residue was purified by silica gel chromatography to give the compound as a white solid MM-I-02 (0.79 g, 75%): 1H NMR (300 MHz, CDCl3) δ 9.23 (s, 1H; H-8), 8.40 (s, 1H; H-6), 7.70 (dd, J=9.1, 1.9 Hz, 1H; H-2), 4.54 (q, J=7.1 Hz, 2H; H-18), 1.49 (t, J=7.1 Hz, 3H; H-17). HRMS m/z calculated for C12H8NO2FClBr 331.9484 found 331.9487.

Ethyl 4-chloro-7-(trifluoromethyl)quinoline-3-carboxylate [MM-I-05]. The reaction was performed following the same procedure as for MM-I-02 except the reaction was performed in bigger scale. Ethyl 4-hydroxy-7-(trifluoromethyl)quinoline-3-carboxylate MM-I-04 (5 g, 18 mmol) was heated with POCl3 (10 mL) at 70° C. for 3 h. MM-I-05 was obtained as a white solid (5.1 g, 93%): mp 71-73° C.; 1H NMR (300 MHz, CDCl3) b 9.30 (s, 1H; H-8), 8.56 (d, J=8.9 Hz, 1H; H-6), 8.46 (s, 1H; H-3), 7.89 (dd, J=8.9, 1.5 Hz, 1H; H-1), 4.54 (q, J=7.1 Hz, 2H; H-20), 1.50 (t, J=7.1 Hz, 3H; H-19); 13C NMR (75 MHz, CDCl3) δ 163.96 (s), 151.35 (s), 148.54 (s), 143.47 (s), 133.53 (q), 127.84 (s), 127.60 (q), 126.92 (s), 124.69 (s), 124.01 (q), 118.86 (s), 62.45 (s), 14.21 (s); HRMS m/z calculated for C13H9NO2F3Cl, 304.0347 found 304.0353.

2-Methoxy-d3-5-nitropyridine [DK-II-44-1]. To a mixture of potassium t-butoxide (13.3 g, 11.8 mmol) and methanol-d4 (50 mL) was slowly added 2-chloro-5-nitropyridine (15.0 g, 94.6 mmol). The exothermic reaction warmed to 50° C. and then was refluxed at 65° C. for 2 h to complete the reaction. The reaction mixture was then cooled to 20-25° C. and poured into water (750 mL). After stirring the mixture for 1 h the solid product was filtered and washed twice with water (25 mL×2). The solid was dried to afford the product as a light yellow powder DK-II-44-1 (13.0 g, 87%). $^1$H NMR (300 MHz, DMSO) b 9.08 (s, 1H), 8.47 (d, J=9.1 Hz, 1H), 7.03 (d, J=9.1 Hz, 1H); $^{13}$C NMR (75 MHz, DMSO) δ 167.45, 145.02, 139.99, 135.01, 111.67; HRMS m/z calculated for C6H4D3N2O3 (M+H)+158.0642 found 158.20.

5-Amino-2-methoxy-d3-pyridine [DK-II-45-1]. A mixture of 2-methoxy-d3-5-nitropyridine DK-II-44-1 (13.0 g, 82.7 mmol), iron powder (15.9 g, 284.7 mmol), water (5 mL) and ethanol (50 mL) was heated to reflux (78° C.). Once at reflux, concentrated hydrochloric acid (1 mL, 83.3 mmol) was added dropwise. The reaction mixture was then refluxed for 4 h to complete the reaction. Upon cooling to 20-25° C., the mixture was filtered to remove the iron and the solids were washed 3 times with ethanol (25 mL×3). Sodium bicarbonate (5.0 g) was added to the filtrate and the ethanol was removed by evaporation on a rotovap. Water (50 mL) and dichloromethane (50 mL) were added to dissolve the residue. The layers were separated and the aqueous layer was extract twice with dichloromethane (50 mL×2). The combined organic layers were dried over magnesium sulfate. The solvents were then removed by evaporation on a rotovap and the product was obtained as a clear orange-red oil DK-II-45-1 (10.0 g, 95.1%): $^1$H NMR (300 MHz, DMSO) δ 7.57 (d, J=2.7 Hz, 1H), 7.05 (dd, J=8.6, 2.9 Hz, 1H), 6.56 (d, J=8.7 Hz, 1H), 4.74 (s, 2H); $^{13}$C NMR (75 MHz, DMSO) δ 156.29, 139.77, 131.63, 126.85, 110.42; HRMS m/z calculated for C6H6D3N2O (M+H)+128.0901 found 128.15.

4-Methoxy-d3-phenylhydrazine [DK-I-29-2]. A mixture of N-(4-methoxy-d3-phenyl)acetamide DK-I-6-1 (30 g, 178.4 mmol), concentrated hydrochloric acid (72 mL), and water (72 mL) was heated to and held at 90° C. for 2 h to hydrolyze the amide functionality. The reaction mixture was then cooled to 0 to 5° C. and a solution of sodium nitrite (12.9 g, 187.7 mmol) and water (25 mL) was slowly added drop-wise to the reaction mixture. Upon completion of the addition, the reaction mixture was stirred for an additional 15 min at 0 to 5° C. The reaction mixture was then cooled to −25 to −20° C. and a solution of tin (II) chloride (74.4 g, 392.4 mmol) and concentrated hydrochloric acid (150 mL) was added drop-wise to the reaction mixture over 30 min. Upon completion of the addition, the reaction mixture was stirred for an additional 4 h at −25 to −20° C. The reaction mixture was then diluted with diethyl ether (300 mL) and the solids were filtered and washed three times with diethyl ether (100 mL×3). The tin adduct of the product was then dissolved in a mixture of sodium hydroxide (60 g), water (250 mL) and dichloromethane (250 mL). After stirring for 2 h at 0 to 5° C., the solids completely dissolved. The layers were separated and the aqueous layer was extracted three times with dichloromethane (100 mL×3). The combined organic layers were then dried over magnesium sulfate. The solvents were then removed by evaporation on a rotovap and the product residue was slurried with hexanes (50 mL). The solid product was then filtered and washed twice with hexanes (50 mL×2). The solid was dried to afford the product as a pale orange crystalline solid DK-I-29-2 (16.6 g, 66%): $^1$H NMR (300 MHz, MeOD) δ 6.91-6.85 (m, 2H), 6.85-6.78 (m, 2H), 4.88 (s, 3H); $^{13}$C NMR (75 MHz, DMSO) δ 152.05, 147.27, 114.60, 113.38; HRMS m/z calculated for C7H8D3N2O (M+H)+142.1057 found 142.25.

3-Methoxy-d3-phenylhydrazine [DK-I-26-3]. A mixture of N-(3-methoxy-d3-phenyl)acetamide DK-I-8-1 (25 g, 148.6 mmol), concentrated hydrochloric acid (60 mL), and water (60 mL) was heated to and held at 90° C. for 2 h to hydrolyze the amide functionality. The reaction mixture was then cooled to 0 to 5° C. and a solution of sodium nitrite (10.8 g, 156.1 mmol) and water (21 mL) was slowly added drop-wise to the reaction mixture. Upon completion of the addition, the reaction mixture was stirred for an additional 15 min at 0 to 5° C. The reaction mixture was then cooled to −25 to −20° C. and a solution of tin (II) chloride (62.0 g, 327.0 mmol) and concentrated hydrochloric acid (125 mL) was added drop-wise to the reaction mixture over 30 min. Upon completion of the addition, the reaction mixture was stirred for an additional 2 h at −25 to −20° C. The reaction mixture was then diluted with diethyl ether (250 mL) and the solids were filtered and washed three times with diethyl ether (100 mL×3). The tin adduct of the product was then dissolved in a mixture of sodium hydroxide (20 g), water (100 mL) and dichloromethane (100 mL). After stirring for 1 h at 0 to 5° C., the solids completely dissolved. The layers were separated and the aqueous layer was extracted three times with dichloromethane (50 mL×3). The combined organic layers were then dried over magnesium sulfate. The solvents were then removed by evaporation on a rotovap to afford the product as an orange-red oil DK-I-26-3 (5.4 g, 26%): $^1$H NMR (300 MHz, DMSO) δ 6.98 (t, J=8.0 Hz, 1H), 6.65 (s, 1H), 6.51-6.27 (m, 2H), 6.16 (d, J=7.9 Hz, 1H), 3.91 (s, 2H); $^{13}$C NMR (75 MHz, DMSO) δ 160.68, 154.54, 129.69, 104.96, 102.72, 97.52; HRMS m/z calculated for C7H8D3N2O (M+H)+ 142.1057 found 142.15.

2-Methoxy-d3-phenylhydrazine [DK-I-43-3]. A mixture of N-(2-methoxy-d3-phenyl)acetamide DK-I-31-1 (25 g, 148.6 mmol), concentrated hydrochloric acid (60 mL), and water (60 mL) was heated to and held at 90° C. for 2 h to hydrolyze the amide functionality. The reaction mixture was then cooled to 0 to 5° C. and a solution of sodium nitrite (10.7 g, 156.1 mmol) and water (21 mL) was slowly added drop-wise to the reaction mixture. Upon completion of the addition, the reaction mixture was stirred for an additional 15 min at 0 to 5° C. The reaction mixture was then cooled to −25 to −20° C. and a solution of tin (II) chloride (62.0 g, 327.0 mmol) and concentrated hydrochloric acid (125 mL) was added drop-wise to the reaction mixture over 30 min. Upon completion of the addition, the reaction mixture was stirred for an additional 2 h at −25 to −20° C. The reaction mixture was then diluted with diethyl ether (300 mL) and the solids were filtered and washed three times with diethyl ether (100 mL×3). The tin adduct of the product was then dissolved in a mixture of sodium hydroxide (20 g), water (100 mL) and dichloromethane (100 mL). After stirring for 1 h at 0 to 5° C., the solids completely dissolved. The layers were separated and the aqueous layer was extracted three times with dichloromethane (100 mL×3). The combined organic layers were then dried over magnesium sulfate. The solvents were then removed by evaporation on a rotovap and the product residue was slurried with hexanes (50 mL). The solid product was then filtered and washed twice with hexanes (25 mL×2). The solid was dried to afford the product as a pale pink solid DK-I-43-3 (12.5 g, 60%): $^1$H NMR (300 MHz, DMSO) δ 7.01 (dd, J=7.8, 1.3 Hz, 1H), 6.92-6.71 (m, 2H), 6.61 (td, J=7.7, 1.4 Hz, 1H), 5.92 (s, 1H), 3.92 (s, 2H); $^{13}$C NMR (75 MHz, DMSO) δ 146.33, 141.94, 121.26, 117.23, 111.20, 110.07; HRMS m/z calculated for C7H8D3N2O (M+H)+ 142.1057 found 142.30.

5-Hydrazinyl-2-methoxypyridine [DK-I-82-3]. A mixture of 5-amino-2-methoxypyridine (10 g, 80.6 mmol), concentrated hydrochloric acid (24 mL), and water (24 mL) was cooled to 0 to 5° C. and a solution of sodium nitrite (5.8 g, 84.6 mmol) and water (12 mL) was slowly added drop-wise to the reaction mixture. Upon completion of the addition, the reaction mixture was stirred for an additional 15 min at 0 to 5° C. The reaction mixture was then cooled to −25 to −20° C. and a solution of tin (II) chloride (33.6 g, 177.2 mmol) and concentrated hydrochloric acid (70 mL) was added drop-wise to the reaction mixture over 30 min. Upon completion of the addition, the reaction mixture was stirred for an additional 2 h at −25 to −20° C. The reaction mixture was then diluted with dichloromethane (100 mL). A solution of potassium hydroxide (100 g), water (200 mL) was added dropwise to the reaction mixture at 0 to 5° C. over 30 min. After stirring for 1 h at 0 to 5° C., the solids completely dissolved. The layers were separated and the aqueous layer was extracted four times with dichloromethane (50 mL×4). The combined organic layers were then dried over magnesium sulfate. The solvents were then removed by evaporation on a rotovap and the product residue was slurried with hexanes (20 mL). The slurry was placed in a freezer at −20° C. for 24 h to fully precipitate the product. The solid product was then filtered and washed twice with hexanes (10 mL×2). The solid was dried to afford the product as a pale yellow-brown solid DK-I-82-3 (7.8 g, 70%): $^1$H NMR (300 MHz, DMSO) δ 7.70 (s, 1H), 7.20 (d, J=8.7 Hz, 1H), 6.61 (d, J=8.8 Hz, 1H), 6.41 (s, 1H), 3.97 (s, 2H), 3.73 (s, 3H); $^{13}$C NMR (75 MHz, DMSO) δ 156.98, 144.09, 129.85, 125.25, 110.22, 53.19; HRMS m/z calculated for C6H10N3O (M+H)+ 140.0824 found 140.25.

5-Hydrazinyl-2-methoxy-d3-pyridine [DK-II-56-1]. A mixture of 5-amino-2-methoxy-d3-pyridine DK-II-45-1 (10 g, 78.6 mmol), concentrated hydrochloric acid (24 mL), and water (24 mL) was cooled to 0 to 5° C. and a solution of sodium nitrite (5.7 g, 82.5 mmol) and water (12 mL) was slowly added drop-wise to the reaction mixture. Upon completion of the addition, the reaction mixture was stirred for an additional 15 min at 0 to 5° C. The reaction mixture was then cooled to −25 to −20° C. and a solution of tin (II) chloride (32.8 g, 173.0 mmol) and concentrated hydrochloric acid (70 mL) was added drop-wise to the reaction mixture over 30 min. Upon completion of the addition, the reaction mixture was stirred for an additional 2 h at −25 to −20° C. The reaction mixture was then diluted with dichloromethane (100 mL). A solution of potassium hydroxide (100 g), water (200 mL) was added dropwise to the reaction mixture at 0 to 5° C. over 30 min. After stirring for 1 h at 0 to 5° C., the solids completely dissolved. The layers were separated and the aqueous layer was extracted four times with dichloromethane (50 mL×4). The combined organic layers were then dried over magnesium sulfate. The solvents were then removed by evaporation on a rotovap and the product residue was slurried with hexanes (20 mL). The slurry was placed in a freezer at −20° C. for 24 h to fully precipitate the product. The solid product was then filtered and washed twice with hexanes (10 mL×2). The solid was dried to afford the product as a pale yellow-brown solid DK-II-56-1 (6.4 g, 57%): $^1$H NMR (300 MHz, DMSO) δ 7.70 (d, J=2.8 Hz, 1H), 7.31-7.19 (m, 1H), 6.61 (d, J=8.8 Hz, 1H), 6.42 (s, 1H), 4.00 (s, 2H); $^{13}$C NMR (75 MHz, DMSO) δ 157.01, 144.07, 129.87, 125.27, 110.22; HRMS m/z calculated for C6H7D3O (M+H)$^+$ 143.1010 found 143.25.

7-Methoxy-2-(4-methoxyphenyl)-2,5-dihydro-3H-pyrazolo[4,3-c]quinolin-3-one [Comp 6]. A mixture of ethyl-4-chloro-7-methoxyquinoline-3-carboxylate DK-I-40-1 (4 g, 15.1 mmol), 4-methoxyphenylhydrazine hydrochloride (3.15 g, 18.1 mmol), triethylamine (3.66 g, 36.1 mmol) and xylenes (32 mL) was heated to reflux (138° C.) and held at reflux for 2 h. The resulting yellow-orange slurry was cooled to 100° C. and diluted with ethanol (32 mL). The reaction mixture was then refluxed at 80° C. for 30 min and then cooled to 20-25° C. The solids were collected by filtration and washed twice with a 1:1 mixture of ethanol (2.5 mL×2) and hexanes (2.5 mL×2) and then washed twice with hexanes (5 mL×2). The solid was dried to afford the product as a yellow powder Comp 6 (2.0 g, 41%): $^1$H NMR (300 MHz, DMSO) δ 12.59 (s, 1H), 8.65 (s, 1H), 8.10 (t, J=8.7 Hz, 3H), 7.34-7.12 (m, 2H), 7.01 (d, J=9.1 Hz, 2H), 3.87 (s, 3H), 3.78 (s, 3H); $^{13}$C NMR (75 MHz, DMSO) δ 161.45, 160.85, 156.22, 143.11, 139.33, 137.42, 134.10, 124.05, 120.68, 115.77, 114.25, 112.68, 106.87, 102.26, 55.98, 55.68; HRMS m/z calculated for C18H16N3O3 (M+H)+ 322.1191 found 322.25.

7-Methoxy-d3-2-(4-methoxyphenyl)-2,5-dihydro-3H-pyrazolo[4,3-c]quinolin-3-one [RV-I-029]. A mixture of ethyl-4-chloro-7-methoxy-d3-quinoline-3-carboxylate DK-I-57-1 (2 g, 7.4 mmol), 4-methoxyphenylhydrazine hydrochloride (1.56 g, 8.9 mmol), triethylamine (1.81 g, 17.6 mmol) and xylenes (16 mL) was heated to reflux (138° C.) and held at reflux for 2 h. The resulting yellow-orange slurry was cooled to 100° C. and diluted with ethanol (16 mL). The reaction mixture was then refluxed at 80° C. for 30 min and then cooled to 20-25° C. The solids were collected by filtration and washed twice with a 1:1 mixture of ethanol (2.5 mL×2) and hexanes (2.5 mL×2) and then washed twice with hexanes (5 mL×2). The solid was dried to afford the product as a yellow powder RV-I-029 (1.0 g, 41%): $^1$H NMR (300 MHz, DMSO) δ 12.59 (s, 1H), 8.65 (s, 1H), 8.10 (t, J=8.7 Hz, 3H), 7.17 (d, J=2.0 Hz, 2H), 7.01 (d, J=8.9 Hz, 2H), 3.78 (s, 3H); $^{13}$C NMR (75 MHz, DMSO) δ 161.45, 160.86, 156.22, 143.11, 139.32, 137.42, 134.11, 124.05, 120.68, 115.76, 114.25, 112.66, 106.87, 102.25, 55.68; HRMS m/z calculated for C18H13D3N3O3 (M+H)+ 325.1377 found 325.30.

7-Methoxy-2-(4-methoxy-d3-phenyl)-2,5-dihydro-3H-pyrazolo[4,3-c]quinolin-3-one [DK-I-56-1]. A mixture of ethyl-4-chloro-7-methoxyquinoline-3-carboxylate DK-I-40-1 (2 g, 7.4 mmol), 4-methoxy-d3-phenylhydrazine DK-I-29-2 (1.25 g, 8.9 mmol), triethylamine (0.90 g, 8.9 mmol) and xylenes (16 mL) was heated to reflux (138° C.) and held at reflux for 2 h. The resulting yellow-orange slurry was cooled to 100° C. and diluted with ethanol (16 mL). The reaction mixture was then refluxed at 80° C. for 30 min and then cooled to 20-25° C. The solids were collected by filtration and washed twice with a 1:1 mixture of ethanol (2.5 mL×2) and hexanes (2.5 mL×2) and then washed twice with hexanes (5 mL×2). The solid was dried to afford the product as a yellow powder DK-I-56-1 (1.5 g, 62.5%): $^1$H NMR (300 MHz, DMSO) δ 12.60 (s, 1H), 8.66 (s, 1H), 8.10 (t, J=9.7 Hz, 3H), 7.18 (s, 2H), 7.01 (d, J=8.4 Hz, 2H), 3.88 (s, 3H); $^{13}$C NMR (75 MHz, DMSO) δ 160.73, 160.43, 156.39, 143.09, 139.34, 137.43, 134.08, 124.08, 120.68, 115.80, 114.24, 112.69, 106.87, 102.28, 56.00; HRMS m/z calculated for C18H13D3N3O3 (M+H)+325.1377 found 325.30.

7-Methoxy-d3-2-(4-methoxy-d3-phenyl)-2,5-dihydro-3H-pyrazolo[4,3-c]quinolin-3-one [DK-I-60-3]. A mixture of ethyl-4-chloro-7-methoxy-d3-quinoline-3-carboxylate DK-I-57-1 (2 g, 7.4 mmol), 4-methoxy-d3-phenylhydrazine DK-I-29-2 (1.26 g, 8.9 mmol), triethylamine (0.90 g, 8.9 mmol) and xylenes (16 mL) was heated to reflux (138° C.) and held at reflux for 2 h. The resulting yellow-orange slurry was cooled to 100° C. and diluted with ethanol (16 mL). The reaction mixture was then refluxed at 80° C. for 30 min and then cooled to 20-25° C. The solids were collected by filtration and washed twice with a 1:1 mixture of ethanol (2.5 mL×2) and hexanes (2.5 mL×2) and then washed twice with hexanes (5 mL×2). The solid was dried to afford the product as a yellow powder DK-I-60-3 (1.2 g, 50.0%): $^1$H NMR (300 MHz, DMSO) δ 12.57 (s, 1H), 8.65 (s, 1H), 8.10 (t, J=9.0 Hz, 3H), 7.17 (d, J=5.7 Hz, 2H), 7.01 (d, J=9.0 Hz, 2H); $^{13}$C NMR (75 MHz, DMSO) δ 161.46, 160.85, 156.21, 143.12, 139.37, 137.48, 134.10, 124.05, 120.69, 115.76, 114.24, 112.68, 106.86, 102.30; HRMS m/z calculated for C18H10D6N3O3 (M+H)+328.1569 found 328.15.

7-Methoxy-d3-2-(3-methoxy-d3-phenyl)-2,5-dihydro-3H-pyrazolo[4,3-c]quinolin-3-one [DK-I-94-1]. A mixture of ethyl-4-chloro-7-methoxy-d3-quinoline-3-carboxylate DK-I-57-1 (2 g, 7.4 mmol), 3-methoxy-d3-phenylhydrazine DK-I-26-3 (1.26 g, 8.9 mmol), triethylamine (0.90 g, 8.9 mmol) and xylenes (16 mL) was heated to reflux (138° C.) and held at reflux for 2 h. The resulting yellow-orange slurry was cooled to 100° C. and diluted with ethanol (16 mL). The reaction mixture was then refluxed at 80° C. for 30 min and then cooled to 20-25° C. The solids were collected by filtration and washed twice with a 1:1 mixture of ethanol (2.5 mL×2) and hexanes (2.5 mL×2) and then washed twice with hexanes (5 mL×2). The solid was dried to afford the product as a yellow powder DK-I-94-1 (1.5 g, 62.0%): $^1$H NMR (300 MHz, DMSO) δ 12.62 (s, 1H), 8.66 (s, 1H), 8.13 (d, J=9.4 Hz, 1H), 7.93-7.73 (m, 2H), 7.34 (t, J=8.2 Hz, 1H), 7.18 (d, J=6.7 Hz, 2H), 6.74 (d, J=8.2 Hz, 1H); $^{13}$C NMR (75 MHz, DMSO) δ 162.13, 161.02, 159.97, 143.50, 141.73, 139.59, 137.58, 129.94, 124.18, 115.84, 112.56, 111.30, 109.60, 106.83, 104.81, 102.32; HRMS m/z calculated for C18H10D6N3O3 (M+H)+328.1569 found 328.25.

7-Methoxy-d3-2-(2-methoxy-d3-phenyl)-2,5-dihydro-3H-pyrazolo[4,3-c]quinolin-3-one [DK-I-90-1]. A mixture of ethyl-4-chloro-7-methoxy-d3-quinoline-3-carboxylate DK-I-57-1 (2 g, 7.4 mmol), 2-methoxy-d3-phenylhydrazine DK-I-43-3 (1.26 g, 8.9 mmol), triethylamine (0.90 g, 8.9 mmol) and xylenes (16 mL) was heated to reflux (138° C.) and held at reflux for 2 h. The resulting yellow-orange slurry was cooled to 100° C. and diluted with ethanol (16 mL). The reaction mixture was then refluxed at 80° C. for 30 min and then cooled to 20-25° C. The solids were collected by filtration and washed twice with a 1:1 mixture of ethanol (2.5 mL×2) and hexanes (2.5 mL×2) and then washed twice with hexanes (5 mL×2). The solid was dried to afford the product as a yellow powder DK-I-90-1 (1.8 g, 75.0%): $^1$H NMR (300 MHz, DMSO) δ 12.47 (s, 1H), 8.57 (s, 1H), 7.99 (d, J=8.7 Hz, 1H), 7.51-7.24 (m, 2H), 7.22-6.93 (m, 4H); $^{13}$C NMR (75 MHz, DMSO) δ 162.19, 160.63, 155.66, 142.97, 139.04, 137.26, 129.88, 129.67, 128.51, 123.87, 120.65, 115.49, 112.96, 112.91, 105.83, 102.15; HRMS m/z calculated for C18H10D6N3O3 (M+H)+328.1569 found 328.30.

7-Methoxy-2-(2-methoxy-d3-phenyl)-2,5-dihydro-3H-pyrazolo[4,3-c]quinolin-3-one [DK-I-88-1]. A mixture of ethyl-4-chloro-7-methoxy-quinoline-3-carboxylate DK-I-40-1 (2 g, 7.5 mmol), 2-methoxy-d3-phenylhydrazine DK-I-43-3 (1.28 g, 9.0 mmol), triethylamine (0.91 g, 9.0 mmol) and xylenes (16 mL) was heated to reflux (138° C.) and held at reflux for 2 h. The resulting yellow-orange slurry was cooled to 100° C. and diluted with ethanol (16 mL). The reaction mixture was then refluxed at 80° C. for 30 min and then cooled to 20-25° C. The solids were collected by filtration and washed twice with a 1:1 mixture of ethanol (2.5 mL×2) and hexanes (2.5 mL×2) and then washed twice with hexanes (5 mL×2). The solid was dried to afford the product as a yellow powder DK-I-88-1 (1.6 g, 65.6%): $^1$H NMR (300 MHz, DMSO) δ 12.46 (d, J=4.9 Hz, 1H), 8.57 (d, J=5.8 Hz, 1H), 7.99 (d, J=8.7 Hz, 1H), 7.40 (t, J=7.8 Hz, 1H), 7.31 (d, J=7.6 Hz, 1H), 7.15 (dd, J=9.7, 6.0 Hz, 3H), 7.03 (t, J=7.5 Hz, 1H), 3.87 (s, 3H); $^{13}$C NMR (75 MHz, DMSO) δ 184.22, 162.19, 160.62, 155.66, 142.95, 139.04, 137.26, 129.88, 129.66, 128.51, 123.88, 120.65, 115.49, 112.97, 112.94, 105.83, 102.15, 55.94; HRMS m/z calculated for C18H13D3N3O3 (M+H)+325.1377 found 325.25.

8-Chloro-2-(4-methoxyphenyl)-2,5-dihydro-3H-pyrazolo[4,3-c]quinolin-3-one [Comp 11]. A mixture of ethyl-4,6-dichloro-quinoline-3-carboxylate DK-I-35-1 (2 g, 7.4 mmol), 4-methoxyphenylhydrazine hydrochloride (1.55 g, 8.9 mmol), triethylamine (1.80 g, 17.8 mmol) and xylenes (16 mL) was heated to reflux (138° C.) and held at reflux for 2 h. The resulting yellow-orange slurry was cooled to 100° C. and diluted with ethanol (16 mL). The reaction mixture was then refluxed at 80° C. for 30 min and then cooled to 20-25° C. The solids were collected by filtration and washed twice with a 1:1 mixture of ethanol (2.5 mL×2) and hexanes (2.5 mL×2) and then washed twice with hexanes (5 mL×2). The solid was dried to afford the product as a yellow powder Comp 11 (1.7 g, 71.0%): $^1$H NMR (300 MHz, DMSO) δ 12.95 (d, J=5.6 Hz, 1H), 8.72 (d, J=6.2 Hz, 1H), 8.14 (d, J=2.1 Hz, 1H), 8.08 (d, J=9.0 Hz, 2H), 7.70 (dt, J=8.9, 5.5 Hz, 2H), 7.02 (d, J=9.1 Hz, 2H), 3.79 (s, 3H); $^{13}$C NMR (75 MHz, DMSO) δ 161.37, 156.48, 141.97, 139.79, 134.59, 133.87, 131.04, 130.46, 122.08, 121.50, 120.89, 120.48, 114.29, 106.86, 55.71; HRMS m/z calculated for C17H13ClN3O2 (M+H)+326.0696 found 326.25.

8-Chloro-2-(4-methoxy-d3-phenyl)-2,5-dihydro-3H-pyrazolo[4,3-c]quinolin-3-one [DK-I-93-1]. A mixture of ethyl-4,6-dichloro-quinoline-3-carboxylate DK-I-35-1 (2 g, 7.4 mmol), 4-methoxy-d3-phenylhydrazine DK-I-29-2 (1.25 g, 8.9 mmol), triethylamine (0.90 g, 8.9 mmol) and xylenes (16 mL) was heated to reflux (138° C.) and held at reflux for 2 h. The resulting yellow-orange slurry was cooled to 100° C. and diluted with ethanol (16 mL). The reaction mixture was then refluxed at 80° C. for 30 min and then cooled to 20-25° C. The solids were collected by filtration and washed twice with a 1:1 mixture of ethanol (2.5 mL×2) and hexanes (2.5 mL×2) and then washed twice with hexanes (5 mL×2). The solids was dried to afford the product as a yellow powder DK-I-93-1 (1.3 g, 53.6%): $^1$H NMR (300 MHz, DMSO) δ 12.89 (s, 1H), 8.74 (s, 1H), 8.24-7.89 (m, 3H), 7.86-7.56 (m, 2H), 7.02 (d, J=8.9 Hz, 2H); $^{13}$C NMR (75 MHz, DMSO) δ 161.38, 156.49, 141.98, 139.86, 134.59, 133.84, 131.05, 130.49, 122.09, 121.52, 120.91, 120.49, 114.29, 106.88; HRMS m/z calculated for C17H10D3ClN3O2 (M+H)+329.0882 found 329.15.

8-Chloro-2-(3-methoxyphenyl)-2,5-dihydro-3H-pyrazolo[4,3-c]quinolin-3-one [LAU 159]. A mixture of ethyl-4,6-dichloro-quinoline-3-carboxylate DK-I-35-1 (2 g, 7.4 mmol), 3-methoxyphenylhydrazine hydrochloride (1.55 g, 8.9 mmol), triethylamine (1.80 g, 17.8 mmol) and xylenes (16 mL) was heated to reflux (138° C.) and held at reflux for 2 h. The resulting yellow-orange slurry was cooled to 100° C. and diluted with ethanol (16 mL). The reaction mixture was then refluxed at 80° C. for 30 min and then cooled to 20-25° C. The solids were collected by filtration and washed twice with a 1:1 mixture of ethanol (2.5 mL×2) and hexanes (2.5 mL×2) and then washed twice with hexanes (5 mL×2). The solid was dried to afford the product as a yellow powder LAU 159 (0.7 g, 30.0%): $^1$H NMR (300 MHz, DMSO) δ 12.85 (s, 1H), 8.69 (s, 1H), 8.15 (d, J=1.9 Hz, 1H), 7.83 (d, J=8.7 Hz, 2H), 7.70 (dt, J=9.0, 5.4 Hz, 2H), 7.34 (t, J=8.1 Hz, 1H), 6.83-6.65 (m, 1H), 3.81 (s, 3H); $^{13}$C NMR (75 MHz, DMSO) δ 161.99, 159.98, 142.44, 141.52, 140.02, 134.81, 131.11, 130.62, 129.97, 122.17, 121.62, 120.42, 111.47, 110.04, 106.80, 104.96, 55.59; HRMS m/z calculated for C17H13ClN3O2 (M+H)+326.0696 found 326.20.

8-Chloro-2-(3-methoxy-d3-phenyl)-2,5-dihydro-3H-pyrazolo[4,3-c]quinolin-3-one [DK-I-59-1]. A mixture of ethyl-4,6-dichloro-quinoline-3-carboxylate DK-I-35-1 (2 g, 7.4 mmol), 3-methoxy-d3-phenylhydrazine hydrochloride DK-I-26-2 (1.45 g, 8.1 mmol), triethylamine (1.87 g, 18.5 mmol) and xylenes (16 mL) was heated to reflux (138° C.) and held at reflux for 2 h. The resulting yellow-orange slurry was cooled to 100° C. and diluted with ethanol (16 mL). The reaction mixture was then refluxed at 80° C. for 30 min and then cooled to 20-25° C. The solids were collected by filtration and washed twice with a 1:1 mixture of ethanol (2.5 mL×2) and hexanes (2.5 mL×2) and then washed twice with hexanes (5 mL×2). The solid was dried to afford the product as a yellow powder DK-I-59-1 (2.0 g, 87.0%): $^1$H NMR (300 MHz, DMSO) δ 12.85 (s, 1H), 8.71 (s, 1H), 8.17 (s, 1H), 8.00-7.49 (m, 4H), 7.35 (t, J=7.7 Hz, 1H), 6.77 (d, J=7.4 Hz, 1H); $^{13}$C NMR (75 MHz, DMSO) δ 162.01, 160.01, 142.48, 141.54, 140.10, 134.76, 131.15, 130.72, 130.01, 122.14, 121.68, 120.45, 111.42, 110.04, 106.87, 104.95; HRMS m/z calculated for C17H10D3ClN3O2 (M+H)+329.0882 found 329.10.

8-Chloro-2-(2-methoxy-d3-phenyl)-2,5-dihydro-3H-pyrazolo[4,3-c]quinolin-3-one [DK-I-87-1]. A mixture of ethyl-4,6-dichloro-quinoline-3-carboxylate DK-I-35-1 (2 g, 7.4 mmol), 2-methoxy-d3-phenylhydrazine DK-I-43-3 (1.25 g, 8.9 mmol), triethylamine (0.9 g, 8.9 mmol) and xylenes (16 mL) was heated to reflux (138° C.) and held at reflux for 2 h. The resulting yellow-orange slurry was cooled to 100° C. and diluted with ethanol (16 mL). The reaction mixture was then refluxed at 80° C. for 30 min and then cooled to 20-25° C. The solids were collected by filtration and washed twice with a 1:1 mixture of ethanol (2.5 mL×2) and hexanes (2.5 mL×2) and then washed twice with hexanes (5 mL×2). The solid was dried to afford the product as a yellow powder DK-I-87-1 (1.0 g, 41.0%): $^1$H NMR (300 MHz, DMSO) δ 12.74 (s, 1H), 8.66 (s, 1H), 8.03 (s, 1H), 7.69 (p, J=9.0 Hz, 2H), 7.42 (t, J=7.8 Hz, 1H), 7.32 (d, J=7.6 Hz, 1H), 7.17 (d, J=8.3 Hz, 1H), 7.05 (t, J=7.5 Hz, 1H); $^{13}$C NMR (75 MHz, DMSO) δ 162.15, 155.64, 141.87, 139.59, 134.48, 130.83, 130.23, 129.91, 129.85, 128.22, 121.91, 121.40, 120.76, 120.68, 113.00, 105.81; HRMS m/z calculated for C17H10D3ClN3O2 (M+H)+329.0882 found 329.20.

7-Bromo-2-(4-methoxyphenyl)-2,5-dihydro-3H-pyrazolo[4,3-c]quinolin-3-one [LAU 463]. A mixture of ethyl-7-bromo-4-chloro-quinoline-3-carboxylate DK-I-52-1 (2 g, 6.3 mmol), 4-methoxyphenylhydrazine hydrochloride (1.33 g, 7.6 mmol), triethylamine (1.54 g, 15.3 mmol) and xylenes (16 mL) was heated to reflux (138° C.) and held at reflux for 2 h. The resulting yellow-orange slurry was cooled to 100° C. and diluted with ethanol (16 mL). The reaction mixture was then refluxed at 80° C. for 30 min and then cooled to 20-25° C. The solids were collected by filtration and washed twice with a 1:1 mixture of ethanol (2.5 mL×2) and hexanes (2.5 mL×2) and then washed twice with hexanes (5 mL×2). The solid was dried to afford the product as a yellow powder LAU 463 (1.4 g, 60.0%): $^1$H NMR (300 MHz, DMSO) δ 12.75 (s, 1H), 8.74 (s, 1H), 8.09 (dd, J=17.7, 8.8 Hz, 3H), 7.89 (d, J=1.6 Hz, 1H), 7.68 (dd, J=8.6, 1.6 Hz, 1H), 7.02 (d, J=9.1 Hz, 2H), 3.79 (s, 3H); $^{13}$C NMR (75 MHz, DMSO) δ 161.37, 156.47, 142.38, 140.08, 136.98, 133.85, 129.65, 124.51, 122.95, 122.22, 120.87, 118.22, 114.31, 107.21, 55.71; HRMS m/z calculated for C17H13BrN3O2 (M+H)+ 370.0191 found 370.15.

7-Bromo-2-(4-methoxy-d3-phenyl)-2,5-dihydro-3H-pyrazolo[4,3-c]quinolin-3-one [DK-I-58-1]. A mixture of ethyl-7-bromo-4-chloro-quinoline-3-carboxylate DK-I-52-1 (2 g, 6.3 mmol), 4-methoxy-d3-phenylhydrazine DK-I-29-2 (1.08 g, 7.6 mmol), triethylamine (0.77 g, 7.6 mmol) and xylenes (16 mL) was heated to reflux (138° C.) and held at reflux for 2 h. The resulting yellow-orange slurry was cooled to 100° C. and diluted with ethanol (16 mL). The reaction mixture was then refluxed at 80° C. for 30 min and then cooled to 20-25° C. The solids were collected by filtration and washed twice with a 1:1 mixture of ethanol (2.5 mL×2) and hexanes (2.5 mL×2) and then washed twice with hexanes (5 mL×2). The solid was dried to afford the product as a yellow powder DK-I-58-1 (1.0 g, 42.0%): $^1$H NMR (300 MHz, DMSO) δ 12.75 (s, 1H), 8.74 (d, J=4.9 Hz, 1H), 8.09 (dd, J=17.8, 8.7 Hz, 3H), 7.88 (s, 1H), 7.69 (d, J=8.4 Hz, 1H), 7.01 (d, J=8.8 Hz, 2H); $^{13}$C NMR (75 MHz, DMSO) δ 161.35, 156.49, 141.88, 140.06, 136.95, 133.83, 129.65, 124.51, 122.93, 122.18, 120.86, 118.22, 114.24, 107.22; HRMS m/z calculated for C17H10D3BrN3O2 (M+H)+373.0377 found 373.05.

7-Bromo-2-(3-methoxy-d3-phenyl)-2,5-dihydro-3H-pyrazolo[4,3-c]quinolin-3-one [DK-I-92-1]. A mixture of ethyl-7-bromo-4-chloro-quinoline-3-carboxylate DK-I-52-1 (1.5 g, 4.8 mmol), 3-methoxy-d3-phenylhydrazine DK-I-26-3 (0.81 g, 5.7 mmol), triethylamine (0.58 g, 5.7 mmol) and xylenes (12 mL) was heated to reflux (138° C.) and held at reflux for 2 h. The resulting yellow-orange slurry was cooled to 100° C. and diluted with ethanol (12 mL). The reaction mixture was then refluxed at 80° C. for 30 min and then cooled to 20-25° C. The solids were collected by filtration and washed twice with a 1:1 mixture of ethanol (2.5 mL×2) and hexanes (2.5 mL×2) and then washed twice with hexanes (5 mL×2). The solid was dried to afford the product as a yellow powder DK-I-92-1 (0.7 g, 40.0%): $^1$H NMR (300 MHz, DMSO) δ 12.78 (s, 1H), 8.76 (s, 1H), 8.15 (d, J=8.5 Hz, 1H), 7.95-7.76 (m, 3H), 7.71 (d, J=8.6 Hz, 1H), 7.35 (t, J=8.2 Hz, 1H), 6.76 (d, J=8.3 Hz, 1H); $^{13}$C NMR (75 MHz, DMSO) δ 162.00, 160.00, 142.81, 141.51, 140.33, 137.11, 130.03, 129.75, 124.65, 123.22, 122.26, 118.16, 111.39, 109.98, 107.20, 104.92; HRMS m/z calculated for C17H10D3BrN3O2 (M+H)+373.0377 found 373.10.

7-Bromo-2-(2-methoxy-d3-phenyl)-2,5-dihydro-3H-pyrazolo[4,3-c]quinolin-3-one [DK-I-89-1]. A mixture of ethyl-7-bromo-4-chloro-quinoline-3-carboxylate DK-I-52-1 (2 g, 6.3 mmol), 2-methoxy-d3-phenylhydrazine DK-I-43-3 (1.08 g, 7.6 mmol), triethylamine (0.77 g, 7.6 mmol) and xylenes (16 mL) was heated to reflux (138° C.) and held at reflux for 2 h. The resulting yellow-orange slurry was cooled to 100° C. and diluted with ethanol (16 mL). The reaction mixture was then refluxed at 80° C. for 30 min and then cooled to 20-25° C. The solids were collected by filtration and washed twice with a 1:1 mixture of ethanol (2.5 mL×2) and hexanes (2.5 mL×2) and then washed twice with hexanes (5 mL×2). The solid was dried to afford the product as a yellow powder DK-I-89-1 (1.2 g, 50.6%): $^1$H NMR (300 MHz, DMSO) δ 12.60 (s, 1H), 8.64 (d, J=16.3 Hz, 1H), 8.00 (d, J=8.5 Hz, 1H), 7.86 (s, 1H), 7.64 (d, J=8.5 Hz, 1H), 7.41 (t, J=7.8 Hz, 1H), 7.32 (d, J=7.7 Hz, 1H), 7.17 (d, J=8.3 Hz, 1H), 7.04 (t, J=7.5 Hz, 1H); $^{13}$C NMR (75 MHz, DMSO) δ 162.14, 158.75, 155.64, 142.23, 139.79, 136.89, 129.84, 129.45, 128.23, 124.36, 122.64, 122.04, 120.69, 118.50, 112.99, 106.18; HRMS m/z calculated for C17H10D3BrN3O2 (M+H)$^+$ 373.0377 found 373.10.

8-Methoxy-d3-2-(4-methoxy-d3-phenyl)-2,5-dihydro-3H-pyrazolo[4,3-c]quinolin-3-one [DK-I-95-3]. A mixture of ethyl-4-chloro-6-methoxy-d3-quinoline-3-carboxylate DK-I-73-2 (2 g, 7.4 mmol), 4-methoxy-d3-phenylhydrazine DK-I-29-2 (1.26 g, 8.9 mmol), triethylamine (0.90 g, 8.9 mmol) and xylenes (16 mL) was heated to reflux (138° C.) and held at reflux for 2 h. The resulting yellow-orange slurry was cooled to 100° C. and diluted with ethanol (16 mL). The reaction mixture was then refluxed at 80° C. for 30 min and then cooled to 20-25° C. The solids were collected by filtration and washed twice with a 1:1 mixture of ethanol (2.5 mL×2) and hexanes (2.5 mL×2) and then washed twice with hexanes (5 mL×2). The solid was dried to afford the product as a yellow powder DK-I-95-3 (0.9 g, 37.0%): $^1$H NMR (300 MHz, DMSO) δ 12.77 (s, 1H), 8.64 (s, 1H), 8.11 (d, J=8.8 Hz, 2H), 7.68 (d, J=9.1 Hz, 1H), 7.57 (s, 1H), 7.28

(d, J=9.1 Hz, 1H), 7.02 (d, J=8.8 Hz, 2H); $^{13}$C NMR (75 MHz, DMSO) δ 161.59, 157.98, 156.34, 143.00, 138.11, 134.10, 130.13, 121.70, 120.92, 120.50, 119.95, 114.23, 105.70, 102.96; HRMS m/z calculated for C18H10D6N3O3 (M+H)+328.1569 found 328.25.

8-Methoxy-d3-2-(3-methoxy-d3-phenyl)-2,5-dihydro-3H-pyrazolo[4,3-c]quinolin-3-one [DK-I-97-1]. A mixture of ethyl-4-chloro-6-methoxy-d3-quinoline-3-carboxylate DK-I-73-2 (2 g, 7.4 mmol), 3-methoxy-d3-phenylhydrazine DK-I-26-3 (1.26 g, 8.9 mmol), triethylamine (0.90 g, 8.9 mmol) and xylenes (16 mL) was heated to reflux (138° C.) and held at reflux for 2 h. The resulting yellow-orange slurry was cooled to 100° C. and diluted with ethanol (16 mL). The reaction mixture was then refluxed at 80° C. for 30 min and then cooled to 20-25° C. The solids were collected by filtration and washed twice with a 1:1 mixture of ethanol (2.5 mL×2) and hexanes (2.5 mL×2) and then washed twice with hexanes (5 mL×2). The solid was dried to afford the product as a yellow powder DK-I-97-1 (1.8 g, 74.0%): $^1$H NMR (300 MHz, DMSO) δ 12.80 (s, 1H), 8.65 (s, 1H), 7.99-7.80 (m, 2H), 7.67 (d, J=9.1 Hz, 1H), 7.59 (s, 1H), 7.41-7.21 (m, 2H), 6.76 (d, J=8.2 Hz, 1H); $^{13}$C NMR (75 MHz, DMSO) δ 162.25, 159.98, 158.04, 143.42, 141.76, 138.36, 130.26, 129.94, 121.73, 120.45, 120.10, 111.53, 109.64, 105.70, 105.11, 103.16; HRMS m/z calculated for C18H10D6N3O3 (M+H)+328.1569 found 328.30.

8-Methoxy-d3-2-(2-methoxy-d3-phenyl)-2,5-dihydro-3H-pyrazolo[4,3-c]quinolin-3-one [DK-I-98-1]. A mixture of ethyl-4-chloro-6-methoxy-d3-quinoline-3-carboxylate DK-I-73-2 (2 g, 7.4 mmol), 2-methoxy-d3-phenylhydrazine DK-I-43-3 (1.26 g, 8.9 mmol), triethylamine (0.90 g, 8.9 mmol) and xylenes (16 mL) was heated to reflux (138° C.) and held at reflux for 2 h. The resulting yellow-orange slurry was cooled to 100° C. and diluted with ethanol (16 mL). The reaction mixture was then refluxed at 80° C. for 30 min and then cooled to 20-25° C. The solids were collected by filtration and washed twice with a 1:1 mixture of ethanol (2.5 mL×2) and hexanes (2.5 mL×2) and then washed twice with hexanes (5 mL×2). The solid was dried to afford the product as a yellow powder DK-I-98-1 (0.5 g, 20.0%): $^1$H NMR (300 MHz, DMSO) δ 12.65 (s, 1H), 8.57 (s, 1H), 7.65 (d, J=9.1 Hz, 1H), 7.54-7.28 (m, 3H), 7.28-7.21 (m, 1H), 7.16 (d, J=8.3 Hz, 1H), 7.05 (t, J=7.5 Hz, 1H); $^{13}$C NMR (75 MHz, DMSO) δ 162.38, 157.83, 155.76, 142.92, 137.98, 130.05, 129.94, 129.83, 128.54, 121.50, 120.75, 120.65, 119.64, 112.91, 104.61, 102.88; HRMS m/z calculated for C18H10D6N3O3 (M+H)+328.1569 found 328.30.

7-Methoxy-2-(6-methoxypyridin-3-yl)-2,5-dihydro-3H-pyrazolo[4,3-c]quinolin-3-one [DK-II-13-1]. A mixture of ethyl-4-chloro-7-methoxy-quinoline-3-carboxylate DK-I-40-1 (2 g, 7.5 mmol), 5-hydrazinyl-2-methoxypyridine DK-I-82-3 (1.26 g, 9.0 mmol), triethylamine (0.91 g, 9.0 mmol) and xylenes (16 mL) was heated to reflux (138° C.) and held at reflux for 2 h. The resulting yellow-orange slurry was cooled to 100° C. and diluted with ethanol (16 mL). The reaction mixture was then refluxed at 80° C. for 30 min and then cooled to 20-25° C. The solids were collected by filtration and washed twice with a 1:1 mixture of ethanol (2.5 mL×2) and hexanes (2.5 mL×2) and then washed twice with hexanes (5 mL×2). The solid was dried to afford the product as a yellow powder DK-II-13-1 (1.2 g, 49.0%): $^1$H NMR (300 MHz, DMSO) δ 12.65 (s, 1H), 8.92 (d, J=2.4 Hz, 1H), 8.68 (s, 1H), 8.43 (dd, J=9.0, 1.8 Hz, 1H), 8.24-7.91 (m, 1H), 7.29-7.02 (m, 2H), 6.92 (d, J=9.0 Hz, 1H), 3.88 (s, 6H); $^{13}$C NMR (75 MHz, DMSO) δ 161.74, 160.98, 160.43, 143.86, 139.71, 137.45, 137.37, 131.88, 130.77, 124.13, 115.94, 112.59, 110.56, 106.22, 102.30, 56.00, 53.71; HRMS m/z calculated for C17H15N4O3 (M+H)+323.1144 found 323.25.

7-Methoxy-d3-2-(6-methoxypyridin-3-yl)-2,5-dihydro-3H-pyrazolo[4,3-c]quinolin-3-one [DK-I-86-1]. A mixture of ethyl-4-chloro-7-methoxy-d3-quinoline-3-carboxylate DK-I-57-1 (2 g, 7.4 mmol), 5-hydrazinyl-2-methoxypyridine DK-I-82-3 (1.24 g, 8.9 mmol), triethylamine (0.90 g, 8.9 mmol) and xylenes (16 mL) was heated to reflux (138° C.) and held at reflux for 2 h. The resulting yellow-orange slurry was cooled to 100° C. and diluted with ethanol (16 mL). The reaction mixture was then refluxed at 80° C. for 30 min and then cooled to 20-25° C. The solids were collected by filtration and washed twice with a 1:1 mixture of ethanol (2.5 mL×2) and hexanes (2.5 mL×2) and then washed twice with hexanes (5 mL×2). The solid was dried to afford the product as a yellow powder DK-I-86-1 (1.0 g, 41.0%): $^1$H NMR (300 MHz, DMSO) δ 12.69 (s, 1H), 8.92 (s, 1H), 8.69 (s, 1H), 8.43 (d, J=9.0 Hz, 1H), 8.12 (d, J=9.4 Hz, 1H), 7.18 (s, 2H), 6.92 (d, J=9.0 Hz, 1H), 3.88 (s, 3H); $^{13}$C NMR (75 MHz, DMSO) δ 161.75, 161.01, 160.44, 143.88, 139.73, 137.46, 137.39, 131.88, 130.79, 124.15, 115.96, 112.57, 110.58, 106.22, 102.31, 53.72; HRMS m/z calculated for C17H12D3N4O3 (M+H)+326.1330 found 326.20.

7-Methoxy-2-(6-methoxy-d3-pyridin-3-yl)-2,5-dihydro-3H-pyrazolo[4,3-c]quinolin-3-one [DK-II-60-1]. A mixture of ethyl-4-chloro-7-methoxy-quinoline-3-carboxylate DK-I-40-1 (2 g, 7.5 mmol), 5-hydrazinyl-2-methoxy-d3-pyridine DK-II-56-1 (1.28 g, 9.0 mmol), triethylamine (0.91 g, 9.0 mmol) and xylenes (16 mL) was heated to reflux (138° C.) and held at reflux for 2 h. The resulting yellow-orange slurry was cooled to 100° C. and diluted with ethanol (16 mL). The reaction mixture was then refluxed at 80° C. for 30 min and then cooled to 20-25° C. The solids were collected by filtration and washed twice with a 1:1 mixture of ethanol (2.5 mL×2) and hexanes (2.5 mL×2) and then washed twice with hexanes (5 mL×2). The solid was dried to afford the product as a yellow powder DK-II-60-1 (1.2 g, 49.0%): $^1$H NMR (300 MHz, DMSO) δ 12.68 (s, 1H), 8.91 (d, J=2.1 Hz, 1H), 8.68 (s, 1H), 8.42 (dd, J=9.0, 2.4 Hz, 1H), 8.16-8.03 (m, 1H), 7.18 (d, J=5.9 Hz, 2H), 6.92 (d, J=9.0 Hz, 1H), 3.87 (s, 3H); $^{13}$C NMR (75 MHz, DMSO) δ 161.74, 160.98, 160.44, 143.85, 139.69, 137.44, 137.39, 131.86, 130.77, 124.13, 115.94, 112.58, 110.54, 106.22, 102.29, 56.00; HRMS m/z calculated for C17H12D3N4O3 (M+H)+326.1330 found 326.30.

8-Chloro-2-(6-methoxypyridin-3-yl)-2,5-dihydro-3H-pyrazolo[4,3-c]quinolin-3-one [DK-II-18-1]. A mixture of ethyl-4,6-dichloro-7-methoxy-3-carboxylate DK-1-35-1 (2 g, 7.4 mmol), 5-hydrazinyl-2-methoxypyridine DK-I-82-3 (1.24 g, 8.9 mmol), triethylamine (0.90 g, 8.9 mmol) and xylenes (16 mL) was heated to reflux (138° C.) and held at reflux for 2 h. The resulting yellow-orange slurry was cooled to 100° C. and diluted with ethanol (16 mL). The reaction mixture was then refluxed at 80° C. for 30 min and then cooled to 20-25° C. The solids were collected by filtration and washed twice with a 1:1 mixture of ethanol (2.5 mL×2) and hexanes (2.5 mL×2) and then washed twice with hexanes (5 mL×2). The solid was dried to afford the product as a yellow powder DK-II-18-1 (1.0 g, 41.0%): $^1$H NMR (300 MHz, DMSO) δ 12.96 (s, 1H), 8.92 (d, J=2.6 Hz, 1H), 8.77 (s, 1H), 8.42 (dd, J=8.9, 2.6 Hz, 1H), 8.14 (s, 1H), 7.89-7.60 (m, 2H), 6.93 (d, J=9.0 Hz, 1H), 3.89 (s, 3H); $^{13}$C NMR (75 MHz, DMSO) δ 161.62, 160.64, 142.70, 140.12, 137.57, 134.58, 131.66, 131.15, 130.92, 130.64, 122.11, 121.58, 120.38, 110.59, 106.25, 53.74; HRMS m/z calculated for C16H12ClN4O2 (M+H)+327.0649 found 327.25.

8-Chloro-2-(6-methoxy-d3-pyridin-3-yl)-2,5-dihydro-3H-pyrazolo[4,3-c]quinolin-3-one [DK-II-59-1]. A mixture of ethyl-4,6-dichloro-quinoline-3-carboxylate DK-I-35-1 (2 g, 7.4 mmol), 5-hydrazinyl-2-methoxy-d3-pyridine DK-II-56-1 (1.26 g, 8.9 mmol), triethylamine (0.90 g, 8.9 mmol) and xylenes (16 mL) was heated to reflux (138° C.) and held at reflux for 2 h. The resulting yellow-orange slurry was cooled to 100° C. and diluted with ethanol (16 mL). The reaction mixture was then refluxed at 80° C. for 30 min and then cooled to 20-25° C. The solids were collected by filtration and washed twice with a 1:1 mixture of ethanol (2.5 mL×2) and hexanes (2.5 mL×2) and then washed twice with hexanes (5 mL×2). The solid was dried to afford the product as a yellow powder DK-II-59-1 (1.4 g, 57.0%): $^1$H NMR (300 MHz, DMSO) δ 12.92 (s, 1H), 8.90 (d, J=1.7 Hz, 1H), 8.74 (d, J=9.1 Hz, 1H), 8.40 (dd, J=8.9, 2.4 Hz, 1H), 8.09 (s, 1H), 7.78-7.61 (m, 2H), 6.90 (d, J=8.9 Hz, 1H); $^{13}$C NMR (75 MHz, DMSO) δ 161.60, 160.63, 142.67, 140.06, 137.55, 134.55, 131.64, 131.13, 130.87, 130.60, 122.07, 121.56, 120.37, 110.55, 106.26; HRMS m/z calculated for C16H9D3ClN4O2 (M+H)+330.0835 found 330.25.

7-Bromo-2-(6-methoxypyridin-3-yl)-2,5-dihydro-3H-pyrazolo[4,3-c]quinolin-3-one [DK-II-48-1]. A mixture of ethyl-7-bromo-4-chloroquinoline-3-carboxylate DK-I-52-1 (2 g, 6.3 mmol), 5-hydrazinyl-2-methoxypyridine DK-I-82-3 (1.06 g, 7.6 mmol), triethylamine (0.77 g, 7.6 mmol) and xylenes (16 mL) was heated to reflux (138° C.) and held at reflux for 2 h. The resulting yellow-orange slurry was cooled to 100° C. and diluted with ethanol (16 mL). The reaction mixture was then refluxed at 80° C. for 30 min and then cooled to 20-25° C. The solids were collected by filtration and washed twice with a 1:1 mixture of ethanol (2.5 mL×2) and hexanes (2.5 mL×2) and then washed twice with hexanes (5 mL×2). The solid was dried to afford the product as a yellow powder DK-II-48-1 (1.6 g, 67.0%): $^1$H NMR (300 MHz, DMSO) δ 12.81 (s, 1H), 10.29-10.27 (m, 1H), 8.89 (s, 1H), 8.75 (s, 1H), 8.40 (dd, J=8.9, 2.2 Hz, 1H), 8.09 (d, J=8.5 Hz, 1H), 7.86 (s, 1H), 7.68 (d, J=8.1 Hz, 1H), 6.91 (d, J=8.9 Hz, 1H), 3.88 (s, 3H); $^{13}$C NMR (75 MHz, DMSO) δ 161.63, 160.61, 143.11, 140.38, 137.53, 136.95, 131.65, 130.88, 129.74, 124.54, 123.15, 122.26, 118.12, 110.61, 106.58, 53.74; HRMS m/z calculated for C16H12BrN4O2 (M+H)+371.0143 found 371.20.

7-Bromo-2-(6-methoxy-d3-pyridin-3-yl)-2,5-dihydro-3H-pyrazolo[4,3-c]quinolin-3-one [DK-II-58-1]. A mixture of ethyl-7-bromo-4-chloroquinoline-3-carboxylate DK-I-52-1 (1.20 g, 3.8 mmol), 5-hydrazinyl-2-methoxy-d3-pyridine DK-II-56-1 (0.65 g, 4.6 mmol), triethylamine (0.46 g, 4.6 mmol) and xylenes (16 mL) was heated to reflux (138° C.) and held at reflux for 2 h. The resulting yellow-orange slurry was cooled to 100° C. and diluted with ethanol (16 mL). The reaction mixture was then refluxed at 80° C. for 30 min and then cooled to 20-25° C. The solids were collected by filtration and washed twice with a 1:1 mixture of ethanol (2.5 mL×2) and hexanes (2.5 mL×2) and then washed twice with hexanes (5 mL×2). The solid was dried to afford the product as a yellow powder DK-II-58-1 (0.5 g, 35.0%): $^1$H NMR (300 MHz, DMSO) δ 12.77 (s, 1H), 8.88 (d, J=2.3 Hz, 1H), 8.75 (d, J=8.4 Hz, 1H), 8.39 (dd, J=8.9, 2.5 Hz, 1H), 8.07 (d, J=8.5 Hz, 1H), 7.83 (s, 1H), 7.65 (d, J=8.6 Hz, 1H), 6.90 (d, J=8.9 Hz, 1H); $^{13}$C NMR (75 MHz, DMSO) δ 161.60, 160.60, 143.08, 140.33, 137.51, 136.93, 131.63, 130.83, 129.70, 124.50, 123.11, 122.24, 118.10, 110.56, 106.58; HRMS m/z calculated for C16H9D3BrN4O2 (M+H)+374.0329 found 374.20.

7-Methoxy(d3)-2-(phenyl)-2H-pyrazolo[4,3-c]quinolin-3(5H)-one [RV-37]. A mixture of ethyl-4-chloro-7-methoxy-d3-quinoline-3-carboxylate DK-I-57-1 (0.01 mol, 0.324 g), phenylhydrazine hydrochloride (0.012 mol, 0.172 g) and TEA (0.012 mol, 0.12 g) in 40 mL xylene was refluxed for 4 hr, cooled to room temperature. The precipitated compound was collected by filtration. The compound was recrystallized from methanol as a yellow colored compound RV-I-37, yield 75%, 0.22 g: mp>260° C. dec. 1H NMR (500 MHz, MeOD) 8.5 (s, 1H), 8.236 (d, 1H, J=9.0 Hz), 8.102 (d, 2H, J=9.0), 7.492-7.236 (m, 5H); 13C (125 MHz, MeOD) 161.4, 160.8, 156.2, 143.1, 139.3, 137.4, 137.1, 134.1, 124.0, 120.6, 115.8, 114.2, 112.6, 106.8, 102.2, 78.5, 55.69; HRMS m/z calculated for C17H11D3N3O2 295.1274 found 295.1272.

2-(4-Methoxyphenyl)-2H-pyrazolo[4,3-c][1,5]naphthyridin-3(5H)-one [RV-I-071]. A mixture of ethyl 4-chloro-1,5-naphthyridine-3-carboxylate (0.01 mol, 0.236 g), 4-methoxyphenylhydrazine hydrochloride (0.012 mol, 0.153 g), triethylamine (0.012 mol, 0.12 g) and xylenes (40 mL) was heated to reflux (138° C.) and held at reflux for 4 hours. The resulting yellow-orange slurry was cooled to room temperature and the solids were collected by filtration. The solids washed twice with 20 ml water. Drying of the solid afforded the product as a yellow powder RV-I-071 (0.268 g): $^1$H NMR (300 MHz, DMSO) δ 12.9 (s, 1H), 8.79 (s, 1H), 8.77 (s, 1H), 8.11-8.10 (d, 2H, J=9.0), 8.08 (s, 1H), 7.70-7.68 (m, 1H), 7.05-7.03 (d, 2H, J=9.0), 3.80 (s, 3H); $^{13}$C NMR (75 MHz, DMSO) δ 161.49, 160.85, 156.56, 148.79.11, 143.06, 139.81, 136.60, 133.97, 132.95, 127.93, 125.21, 120.91, 114.33, 109.42, 55.72; HRMS m/z calculated for C16H12N4O2 (M+H)+293.1039 found 293.1037.

8-Bromo-6-fluoro-2-(4-methoxyphenyl)-2H-pyrazolo[4,3-c]quinolin-3(5H)-one [MM-I-03]. A mixture of 0.5 g (1.5 mmol) of ethyl 6-bromo-4-chloro-8-fluoroquinoline-3-carboxylate MM-I-02, 0.31 g (1.8 mmol) of (4-methoxyphenyl)hydrazine hydrochloride and Et3N (2 mL) was placed in a flask with xylene (8 mL) and heated for 4 h. The reaction was cooled at rt and filtered. The solid was washed several times with hexane and water. Then, the solid was dissolved in a base solution 3 N NaOH and stirred for 15 min. The base solution was neutralized with 3 N HCl and filtrated. The solid was recrystallized using hot ethanol and dried in vacuo, affording a yellow solid MM-I-03 (0.28 g, 48%): mp 333-334° C.; 1H NMR (300 MHz, DMSO) δ 8.51 (s, 1H; H-6), 8.09 (s, 1H; H-8), 8.03 (d, J=8.9 Hz, 2H; H-15 and H-19), 7.89 (d, J=10.5 Hz, 1H; H-2), 7.01 (d, J=9.0 Hz, 2H; H-16 and H-18), 3.78 (s, 3H; H-24); 13C NMR (75 MHz, DMSO) δ 161.11 (s), 156.65 (s), 140.93 (s), 139.49 (s), 133.57 (s), 124.37 (s), 124.19 (s), 122.02 (s), 121.00 (s), 120.61 (s), 119.08 (q, J=3.3, 1.9 Hz), 118.82 (s), 118.34 (s), 118.22 (s), 114.32 (s), 107.83 (s), 55.73 (s); HRMS m/z calculated for C17H11N3O2FBr 388.0091 found 388.0094.

2-(4-Methoxyphenyl)-7-(trifluoromethyl)-2H-pyrazolo[4,3-c]quinolin-3(5H)-one [MM-I-06]. Treatment of ethyl 4-chloro-7-(trifluoromethyl)quinoline-3-carboxylate MM-I-05 (0.5 g, 1.5 mmol) with (4-methoxyphenyl)hydrazine hydrochloride (0.57 g, 1.8 mmol) and Et3N (2 mL) in 8 mL of xylene under reflux for 4 h afforded the corresponding product. The reaction was cooled at rt and filtered. The solid was washed several times with hexane and water. An acid-base crystallization was needed to remove the triethylamine salt, and it afforded yellow crystals MM-I-06 (0.51 g, 82%): mp 315-316° C.; 1H NMR (300 MHz, DMSO) δ 12.93 (s, 1H; H-7), 8.84 (s, 1H; H-8), 8.40 (d, J=8.4 Hz, 1H; H-6), 8.08 (d, J=9.1 Hz, 2H; H-15 and H-19), 8.03 (s, 1H; H-3), 7.83 (d, J=8.1 Hz, 1H; H-1), 7.03 (d, J=9.1 Hz, 2H; H-16 and H-18), 3.79 (s, 3H; H-22); 13C NMR (75 MHz, DMSO) δ 161.38 (s), 156.60 (s), 141.99 (s), 140.79 (s), 135.83 (s), 133.75 (s), 130.23 (s), 129.80 (s), 125.96 (s), 124.05 (s), 122.66 (q), 122.35 (s), 122.12 (s), 121.00 (s), 117.21 (q), 114.34 (s), 107.42 (s), 55.71 (s); HRMS m/z calculated for C18H12N3O2F3 360.0954 found 360.0943.

2-(4-Chlorophenyl)-7-(trifluoromethyl)-2H-pyrazolo[4,3-c]quinolin-3(5H)-one [MM-I-08]. The reaction of 0.5 g (1.6 mmol) of ethyl 4-chloro-7-(trifluoromethyl)quinoline-3-carboxylate MM-I-05 with (4-chlorophenyl)hydrazine hydrochloride (0.47 g, 3.2 mmol) and 2 mL of Et$_3$N in 8 mL of xylene at reflux for overnight afforded the product. The recrystallization of solid gave yellow crystals MM-I-08 (0.44 g, 75%): mp 346-347° C.; 1H NMR (300 MHz, DMSO) δ 12.98 (s, 1H; H-7), 8.84 (s, 1H; H-8), 8.34 (d, J=8.3 Hz, 1H; H-1), 8.21 (d, J=8.9 Hz, 2H; H-15 and H-19), 7.98 (s, 1H; H-3), 7.80 (d, J=8.3 Hz, 1H; H-6), 7.47 (d, J=8.9 Hz, 2H; H-18 and H-16); 13C NMR (75 MHz, DMSO) δ 161.92 (s), 142.71 (s), 141.03 (s), 139.11 (s), 135.84 (s), 130.51 (s), 130.08 (s), 129.08 (s), 128.45 (s), 125.88 (s), 124.11 (s), 122.72 (q), 122.27 (s), 121.92 (s), 120.40 (s), 117.15 (q), 107.15 (s). HRMS m/z calculated for C17H9N3OF3Cl, 364.0459 found 364.0453.

2-(4-Nitrophenyl)-7-(trifluoromethyl)-2H-pyrazolo[4,3-c]quinolin-3(5H)-one [MM-I-09]. In a flask containing ethyl 4-chloro-7-(trifluoromethyl)quinoline-3-carboxylate MM-I-05 (0.2 g, 0.66 mmol), (4-nitrophenyl)hydrazine (0.25 g, 1.3 mmol) and xylene (8 mL), was added 2 mL of Et3N and the flask was immediately placed in oil bath previously heated at 150° C. After 4 h of heating, the solid was collected by filtration and washed with hexane and water. The same procedure of acid-base crystallization was used affording reddish solid MM-I-09 (0.035 g, 15%): mp>350° C.; 1H NMR (300 MHz, DMSO) δ 13.09 (s, 1H; H-7), 8.89 (s, 1H; H-8), 8.41 (d, J=9.1 Hz, 2H; H-16 and H-18), 8.35 (d, J=8.4 Hz, 1H; H-6), 8.27 (d, J=9.1 Hz, 2H; H-15 and H-19), 7.95 (s, 1H; H-3), 7.82 (d, J=8.2 Hz, 1H; H-1); HRMS m/z calculated for C17H9N4O3F3 375.0700 found 375.0695.

2-(4-(Trifluoromethoxy)phenyl)-7-(trifluoromethyl)-2H-pyrazolo[4,3-c]quinolin-3(5H)-one [MM-I-10]. A mixture of ethyl 4-chloro-7-(trifluoromethyl)quinoline-3-carboxylate MM-I-05 (0.3 g, 1 mmol) with (4-(trifluoromethoxy)phenyl)hydrazine hydrochloride (0.48 g, 2 mmol) and Et3N (2 mL) in 8 mL of xylene was heated at reflux for overnight. The solid was collected by filtration and washed with hexane and water. The solid was dissolved in 3 N NaOH solution (10 mL) and precipitated with 3 N HCl (11 mL) solution. Then, a recrystallization using 15 mL EtOH and 2 mL of water was used and afforded yellow crystals MM-I-10 (0.25 g, 60%): mp 286-287° C.; 1H NMR (300 MHz, DMSO) δ 8.86 (s, 1H; H-8), 8.36 (d, J=8.4 Hz, 1H; H-6), 8.29 (d, J=9.0 Hz, 2H; H-15 and H-19), 7.99 (s, 1H; H-3), 7.81 (d, J=8.3 Hz, 1H; H-1), 7.43 (d, J=8.8 Hz, 2H; H-16 and H-18); 13C NMR (75 MHz, DMSO) 161.98 (s), 144.85 (s), 142.85 (s), 141.22 (s), 139.27 (s), 135.96 (s), 130.54 (s), 130.11 (s), 124.12 (s), 122.78 (s), 122.29 (q, J=2.8 Hz), 121.98 (s), 120.37 (s), 117.25 (q, J=8.4, 4.7 Hz), 107.07 (s); HRMS m/z calculated for C18H9N3O2F6 414.0672 found 414.0674.

2-(4-Fluorophenyl)-7-(trifluoromethyl)-2H-pyrazolo[4,3-c]quinolin-3(5H)-one [MM-I-11]. Treatment of ethyl 4-chloro-7-(trifluoromethyl)quinoline-3-carboxylate MM-I-05 (0.2 g, 0.66 mmol) with (4-fluorophenyl)hydrazine hydrochloride (0.22 g, 1.3 mmol) and Et3N (2 mL) in 8 mL of xylene under reflux for overnight afforded the corresponding product. The yellow crystals MM-I-11 (0.15 g, 65%) were obtained by recrystallization with hot EtOH: mp 296-297° C.; 1H NMR (300 MHz, DMSO) 12.98 (s, 11H; H-7), 8.84 (s, 11H; H-8), 8.36 (d, J=8.3 Hz, 1H; H-6), 8.19 (dd, J=9.0, 5.1 Hz, 2H; H-15 and H-19), 8.00 (s, 1H; H-3), 7.81 (d, J=8.4 Hz, 1H; H-1), 7.27 (t, J=8.9 Hz, 2H; H-16 and H-18); 13C NMR (75 MHz, DMSO) 161.69 (s), 160.85 (s), 157.66 (s), 142.41 (s), 140.94 (s), 136.74 (s), 135.78 (s), 130.21 (q), 124.09 (d), 124.07 (s), 122.73 (q), 121.99 (s), 120.97 (d), 117.14 (q), 115.95 (s), 115.65 (s), 107.21 (s); HRMS m/z calculated for C17H9N3OF4 348.0755 found 348.0766.

2-(3-Methoxyphenyl)-7-(trifluoromethyl)-2H-pyrazolo[4,3-c]quinolin-3(5H)-one [MM-I-12]. The reaction of 0.5 g (1.6 mmol) of ethyl 4-chloro-7-(trifluoromethyl)quinoline-3-carboxylate MM-I-05 with (3-methoxyphenyl)hydrazine hydrochloride (0.575 g, 4.1 mmol) and 2 mL of Et$_3$N in 15 mL of xylene at reflux for overnight afforded the product. Recrystallization gave yellow crystals MM-I-12 (0.762 g, 46%): mp>350° C.; $^1$H NMR (500 MHz, DMSO) δ 8.85 (s, 1H, H-8), 8.43 (d, J=8.3 Hz, 1H, H-6), 8.04 (s, 1H, H-15), 7.88-7.80 (m, 3H, H-1 H-3 and H-19), 7.37 (t, J=8.2 Hz, 1H, H-18), 6.79 (dd, J=8.2, 2.4 Hz, 1H, H-17), 3.82 (s, 3H, H-22).

8-Bromo-2-(4-chlorophenyl)-6-fluoro-2H-pyrazolo[4,3-c]quinolin-3(5H)-one [MM-I-13]. A mixture of ethyl 6-bromo-4-chloro-8-fluoroquinoline-3-carboxylate MM-I-02 (0.2 g, 0.64 mmol) with (4-chlorophenyl)hydrazine hydrochloride (0.18 g, 1.2 mmol) and Et$_3$N (2 mL) in 8 mL of xylene was heated at reflux for overnight. The solid was collected by filtration and washed with hexane and water. The solid was dissolved in 10 mL of DMSO. The solution was poured in 30 mL of H$_2$O, and filtered in order to remove the triethylamine salt. Then, a recrystallization using 15 mL EtOH and 2 mL of water was used and afforded yellow crystals MM-I-13 (0.17 g, 70%): $^1$H NMR (300 MHz, DMSO) δ 8.54 (s, 1H, H-8), 8.22 (d, J=8.9 Hz, 2H, H-15 and H-19), 8.11 (s, 1H, H-6), 7.92 (dd, J=10.6, 1.8 Hz, 1H, H-2), 7.50 (d, J=8.9 Hz, 2H, H-16 and H-18).

8-Bromo-6-fluoro-2-(4-fluorophenyl)-2H-pyrazolo[4,3-c]quinolin-3(5H)-one [MM-I-18]. Treatment of ethyl 6-bromo-4-chloro-8-fluoroquinoline-3-carboxylate MM-I-02 (0.2 g, 0.64 mmol) with (4-fluorophenyl)hydrazine hydrochloride (0.22 g, 1.3 mmol) and Et$_3$N (2 mL) in 8 mL of xylene under reflux overnight afforded the corresponding product. The yellow crystals MM-I-18 (0.120 g, 50%) were obtained by recrystallization with hot EtOH: $^1$H NMR (300 MHz, DMSO) δ 13.02 (s, 1H, H-7), 8.55 (s, 1H, H-8), 8.25-8.15 (m, 2H, H-15 and H-19), 8.12 (s, 1H, H-6), 7.93 (dd, J=10.6, 1.9 Hz, 1H, H-2), 7.29 (t, J=8.9 Hz, 2H, H-16 and H-18).

7-Methoxy-2-(4-(trifluoromethoxy)phenyl)-2,5-dihydro-3H-pyrazolo[4,3-c]quinolin-3-one [CW-02-082]. To a clean and dry flask ethyl 4-chloro-7-methoxyquinoline-3-carboxylate DK-I-40-1 (531 mg, 2 mmol, 1 EQ), (4-(trifluoromethoxy)phenyl)hydrazine hydrochloride (686 mg, 3 mmol, 1.5 EQ), xylene (10 mL), and TEA (607 mg, 6 mmol, 3 EQ) were charged. The mixture was immediately transferred to pre-heated oil bath (150° C.) and heated overnight at which point it was cooled to 0° C. via ice/water bath and hexanes (20 mL) were added in one portion. The yellow solid was filtered and dried (1.35 g product+TEA*HCl). The mixture was purified via general purification method A and B. The solid was dried overnight under high vacuum obtaining the pure product in 75% yield (563 mg) as a yellow powder CW-02-082: $^1$H NMR (300 MHz, DMSO) δ 12.71 (s, 1H), 8.71 (s, 1H), 8.33 (s, 2H), 8.12 (s, 1H), 7.45 (s, 2H), 7.18 (s, 2H), 3.88 (s, 3H); $^{13}$C NMR (75 MHz, DMSO) δ 162.18, 161.10, 144.50, 144.48, 143.97, 139.93, 139.60, 137.61, 124.15, 121.98, 120.12, 115.95, 112.52, 106.45, 102.37, 56.00; HRMS (ESI) (M+H), Calcd. for C18H13F3N3O3 376.0909; Found 376.0914.

7-Methoxy-2-(4-methoxyphenyl)-6-methyl-2,5-dihydro-3H-pyrazolo[4,3-c]quinolin-3-one [CW-02-073]. To a clean and dry flask ethyl 4-chloro-7-methoxy-8-methylquinoline-3-carboxylate (560 mg, 2 mmol, 1 EQ), (4-methoxyphenyl)hydrazine (524 mg, 3 mmol, 1.5 EQ), xylene (10 mL), and TEA (607 mg, 6 mmol, 3 EQ) were charged. The mixture was immediately transferred to pre-heated oil bath (150° C.) and heated overnight at which point it was cooled to 0° C. via ice/water bath and hexanes (20 mL) were added in one portion. The yellow solid was filtered and dried (1.15 g product+TEA*HCl). The mixture was purified via general purification method B. The solid was dried overnight under high vacuum obtaining the pure product in 70% yield (470 mg) as a yellow solid. $^1$H NMR (300 MHz, DMSO) δ 11.80 (s, 1H), 8.37 (s, 1H), 8.08 (dd, J=8.9, 5.1 Hz, 3H), 7.29 (d, J=9.0 Hz, 1H), 7.01 (d, J=9.1 Hz, 2H), 3.92 (s, 3H), 3.78 (s, 3H), 2.36 (s, 3H). 13C NMR (75 MHz, DMSO) δ 161.39, 158.24, 156.22, 143.58, 139.11, 135.37, 134.09, 121.18, 120.66, 114.33, 114.25, 112.80, 111.11, 106.53, 56.65, 55.68, 10.03. HRMS (ESI) (M+H), Calcd. for C19H18N3O3 336.1348; Found 336.1240.

7-Methoxy-6-methyl-2-phenyl-2,5-dihydro-3H-pyrazolo[4,3-c]quinolin-3-one [CW-02-078]. To a clean and dry flask ethyl 4-chloro-7-methoxy-8-methylquinoline-3-carboxylate (560 mg, 2 mmol, 1 EQ), phenylhydrazine hydrochloride (434 mg, 3 mmol, 1.5 EQ), xylene (10 mL), and TEA (607 mg, 6 mmol, 3 EQ) were charged. The mixture was immediately transferred to pre-heated oil bath (150° C.) and heated overnight at which point it was cooled to 0° C. via ice/water bath and hexanes (20 mL) were added in one portion. The yellow solid was filtered and dried (1.17 g product+TEA*HCl). The mixture was purified via general purification method A. The solid was dried overnight under high vacuum obtaining the pure product in 84% yield (513 mg) as yellow crystals. $^1$H NMR (500 MHz, DMSO) δ 11.86 (s, 1H), 8.42 (s, 1H), 8.22 (d, J=8.2 Hz, 2H), 8.11 (d, J=8.8 Hz, 1H), 7.45 (t, J=7.9 Hz, 2H), 7.33 (d, J=8.9 Hz, 1H), 7.17 (t, J=7.3 Hz, 1H), 3.95 (s, 3H), 2.39 (s, 3H). $^{13}$C NMR (126 MHz, DMSO) δ 162.00, 158.41, 144.04, 140.60, 139.43, 135.49, 129.15, 124.29, 121.32, 118.98, 114.42, 112.77, 111.22, 106.48, 56.71, 10.08. HRMS (ESI) (M+H), Calcd. for C18H16N3O2 306.1243; Found 306.1237.

7-Methoxy-6-methyl-2-(4-(trifluoromethoxy)phenyl)-2,5-dihydro-3H-pyrazolo[4,3-c]quinolin-3-one [CW-02-079]. To a clean and dry flask ethyl 4-chloro-7-methoxy-8-methylquinoline-3-carboxylate (560 mg, 2 mmol, 1 EQ), (4-(trifluoromethoxy) phenyl) hydrazine (689 mg, 3 mmol, 1.5 EQ), xylene (10 mL), and TEA (607 mg, 6 mmol, 3 EQ) were charged. The mixture was immediately transferred to pre-heated oil bath (150° C.) and heated overnight at which point it was cooled to 0° C. via ice/water bath and hexanes (20 mL) were added in one portion. The yellow solid was filtered and dried (1.14 g product+TEA*HCl). The mixture was purified via general purification method B. The solid was dried overnight under high vacuum obtaining the pure product in 68% yield (530 mg) as a yellow powder. $^1$H NMR (300 MHz, DMSO) δ 11.92 (d, J=5.8 Hz, 1H), 8.44 (d, J=6.3 Hz, 1H), 8.33 (d, J=9.1 Hz, 2H), 8.09 (d, J=8.9 Hz, 1H), 7.45 (d, J=8.9 Hz, 2H), 7.32 (d, J=9.0 Hz, 1H), 3.94 (s, 3H), 2.37 (s, 3H). $^{13}$C NMR (75 MHz, CDCl$_3$) δ 162.11, 158.52, 144.48, 144.44, 139.74, 139.57, 135.51, 122.35, 122.00, 121.34, 120.10, 114.51, 112.64, 111.31, 106.11, 56.70, 10.05. HRMS (ESI) (M+H), Calcd. for C19H15F3N3O3 390.1066; Found 390.1068.

7-Methoxy-2-(4-methoxyphenyl)-2,5-dihydro-3H-pyrazolo[4,3-c][1,6]naphthyridin-3-one [CW-03-030]. To a clean and dry flask ethyl 4-chloro-7-methoxy-1,6-naphthyridine-3-carboxylate (78 mg, 0.29 mmol, 1 EQ), (4-methoxyphenyl)hydrazine hydrochloride (76 mg, 0.435 mmol, 1.5 EQ), xylene (5 mL), and TEA (89 mg, 0.87 mmol, 3 EQ) were charged. The mixture was immediately transferred to pre-heated oil bath (150° C.) and heated overnight at which point it was cooled to 0° C. via ice/water bath and hexanes (20 mL) were added in one portion. The yellow solid was filtered and dried (product+TEA*HCl). The mixture was purified via FCC (7% MeOH in DCM) and general purification method A. The solid was dried overnight under high vacuum obtaining the pure product in 47% yield (44 mg) as orange crystals. $^1$H NMR (300 MHz, DMSO) δ 12.60 (s, 1H), 9.06 (s, 1H), 8.67 (s, 1H), 8.02 (d, J=9.1 Hz, 2H), 7.02 (d, J=9.1 Hz, 2H), 6.89 (s, 1H), 3.96 (s, 3H), 3.79 (s, 3H). $^{13}$C NMR (75 MHz, DMSO) δ 164.59, 161.30, 156.46, 144.09, 143.92, 141.36, 141.25, 133.63, 120.84, 114.32, 110.13, 108.40, 96.94, 55.72, 54.49. HRMS (ESI) (M+H), Calcd. for C17H15N4O3 323.1144; Found 323.1138.

7-Chloro-2-(4-methoxyphenyl)-2,5-dihydro-3H-pyrazolo[4,3-c][1,6]naphthyridin-3-one [CW-03-033]. To a clean and dry flask ethyl 4,7-dichloro-1,6-naphthyridine-3-carboxylate (120 mg, 0.443 mmol, 1 EQ), (4-methoxyphenyl)hydrazine hydrochloride (116 mg, 0.664 mmol, 1.5 EQ), xylene (5 mL), and TEA (135 mg, 1.33 mmol, 3 EQ) were charged. The mixture was immediately transferred to pre-heated oil bath (150° C.) and heated overnight at which point it was cooled to 0° C. via ice/water bath and hexanes (15 mL) were added in one portion. The yellow solid was filtered and dried (product+TEA*HCl). The mixture was purified via FCC (7% MeOH in DCM) and general purification method B. The solid was dried overnight under high vacuum obtaining the pure product in 61% yield (88 mg) as an orange solid. $^1$H NMR (300 MHz, DMSO) δ 12.87 (s, 1H), 9.21 (s, 1H), 8.81 (s, 1H), 8.03 (d, J=9.1 Hz, 2H), 7.61 (s, 1H), 7.03 (d, J=9.1 Hz, 2H), 3.79 (s, 3H). $^{13}$C NMR (75 MHz, CDCl$_3$) δ 161.08, 156.70, 150.07, 146.16, 143.21, 141.60, 140.52, 133.41, 121.00, 114.38, 114.10, 113.06, 109.77, 55.73. HRMS (ESI) (M+H), Calcd. for C16H12ClN4O2 327.0649; Found 327.0654.

Purification Method A: Crude compound was heated to reflux in ethanol (10 mL/g) and an aqueous ethanolic solution (50% H$_2$O, 50% ethanol) was slowly added until all compound was completely dissolved at reflux. Once dissolved, water was added dropwise at reflux until the solution became slightly cloudy. The solution was cooled slowly to RT and in most cases microcrystals began to accumulate. The solution was further cooled to 0° C. via ice-bath, filtered, and washed with cold aqueous ethanolic solution (50% H$_2$O, 50% ethanol) overnight. If necessary, compounds were further dried under high vacuum.

Purification Method B: Crude compound was dissolved in minimal DMSO and water was added until compound was completely precipitated from the DMSO solution. The product is filtered and washed with water. The amorphous powder was ground with mortar and pestle and dried under high vacuum for 24 hr's or until little trace of water is present in HNMR.

Example 2

Materials and Methods

Animal Experiments

All animal experiments conducted at NTU were approved by the Institutional Animal Care and Use Committee of College of Medicine, National Taiwan University.

C57/B6 (8-10 weeks) mice were used for the PPI test and Wistar rats (8-9 weeks) were used in the migraine model. Animals were housed in an animal room with a 12-h light/12-h dark cycle and free access to food and water.

PPI Test

The PPI test was conducted with a PPI apparatus (SR-LAB, San Diego Instruments, San Diego, Calif.) consisting of a startle chamber equipped with various programming acoustic stimulations. After acclimation, the mouse was gently placed in the startle chamber for a 4 min acclimation period with a background noise of 65 dB, which continued throughout the whole PPI test session. One PPI test session consisted of 4 types of startle trials, including the trial with the startle pulse (115 dB) alone (PULSEALONE; 115 dB, 20 ms), two trials with the startle pulse paired with 71 and 77 dB prepulses, respectively (PREPULSE+PULSE; 71 dB+115 dB and 77 dB+115 dB), and the trial without stimulus (NOSTIM; background 65 dB only). A test session started and ended, respectively, with four NOSTIM trials and four PULSEALONE trials. In between, each of the four types of trials was presented 14 times randomly, that is, 56 trials were given in a test session. The intertrial interval was given randomly from 5 to 20 s. In the PREPULSE+PULSE trial, a 71 or 77 dB prepulse was given 120 ms before the 115 dBpulse. The magnitude of PPI (PPI %) was determined, after summarizing the startle responses in PULSEALONE and PREPULSE+PULSE trials, according to the equation (PULSEALON−PREPULSE+PULSE)/PULSEALONE×100%. The tested compound or vehicle was given to the animal for 15 min, followed by methamphetamine (2 mg/kg). The PPI test was conducted 10 min after injection of methamphetamine. Data were expressed as the mean±S.E.M. Statistical comparisons among groups were analyzed by ANOVA with Tukey post hoc test, and differences between groups were analyzed by Student's t-test. Two-way ANOVA with Bonferroni's post hoc test was used to analyze differences in the time courses of locomotor activity among groups. Differences were considered significant if $P<0.05$.

Locomotor Activity

The locomotor activity of the mouse was measured by its interruptions of infra-red photobeans in a locomotor cage (42 cm×42 cm×36 cm) in the photobeam activity system (San Diego Instruments, San Diego, Calif.). After acclimation, the mouse was treated with ci extract or vehicle for 15 min, followed by ma (2 mg/kg). Then, the mouse was gently placed in the locomotor cage and the horizontal and vertical interruptions were counted every 5 min for 60 min. Total locomotor activity was the sum of interruptions within 60 min.

The Rotarod Test

The motor coordinating activity of the mouse was measured by its performance on a rotarod in the sdi rotor-rodtm system (San Diego Instruments, San Diego, Calif.). The mouse was trained four times a day for 3 days until it could stay on the rotating drum at a rotating speed of 24 rpm for at least 120 sec. Then, the mouse was subjecting to the rotarod test at the rotating speed accelerating gradually from 0 to 30 rpm, and the latency to fall from the rotating drum was recorded. The cut-off time for the latency to fall was 300 sec. Animals were treated with the tested drug or vehicle for 15 min before receiving the test.

The Grip Strength Test

Forelimb grip strength was measured by the grip force of forepaws of the mouse using the sdi grip strength system (San Diego Instrument, San Diego, Calif.). The grip strength was recorded by the maximum of three permissible readings (in grams). The test was conducted every 2 min for three times, and the averaged grip strength was recorded. Animals were treated with the tested drug or vehicle for 15 min before the test.

Apomorphine-Induced Stereotypy Behaviors

The mouse was placed into a lidded cylindrical cage (diameter: 12 cm; height: 14 cm) made with 1 cm-separated metal grids for 1 hour's habituation. Then, the mouse received apomorphine (1 mg/kg, s.c.) Injection. The behaviors of the mouse were videotaped, and the stereotypy behaviors were scored every 5 min for 1 min, starting from 15 min before apomorphine injection until 60 min after injection.

The stereotypy behaviors induced by apomorphine were scored by reference to a previous report (Park et al. 2003) with modifications as the followings: 0: normal behaviors (sleeping, normal sniffing); 1: increased activity and sniffing (grooming, rearing, paw licking, jumping); 2: occasional clinging to the side wall of the cage with forepaws; 3: intermittent clinging to the top lid of the cage with all four paws; 4: uninterrupted climbing with all four paws to the top lid. The highest rating score during the 1 min-recording period was counted.

The Elevated Plus Maze (Epm) Test

The elm test was conducted in a plexiglass maze apparatus (San Diego Instruments, San Diego, Calif.), consisting of a central platform (5×5 cm) with four arms (30×5 cm); two open and two closed arms with 25 cm-high sidewalls. The maze is elevated 38.5 cm from the room's floor. The mouse was placed at the central platform of the maze facing one of open arms and its behaviors in the maze were video-recorded and analyzed every 5 min-test session by the ethovision video tracking system (noldus information technology, wageningen, netherlands). The time spent for each mouse in the open or closed arm or the central platform as well as the distances traveled in the open or closed arm were measured. The degree of anxiety was accessed by the ratio of the time spent or the distance traveled in two open arms in a 5 min-test session.

Sedation Assessment

The degree of sedation was measured by the latency for a mouse to completely step down from a slightly (3 cm) raised plastic platform (11×8 cm) by reference to a previous report (Horan et al. 1991). The mouse was placed on the platform 15 min after receiving i.p. Injection of the tested drug. The latency (in sec) for the mouse to step down the platform with all four paws was recorded. The baseline latency of each mouse before drug treatment was measured and, if longer than 15 sec, the mouse was discarded from the study. A cut-off time of 60 sec was taken as the maximal sedative effect. The percentage of sedation was calculated by the formula: sedation %=(test latency−baseline latency)/(60−baseline latency)×100%.

Bilateral Intra-Cerebellar (i.cb.) Microinjection

Mice were anaesthetized with sodium pentobarbital (60 mg/kg i.p.) And placed in a stereotaxic frame keeping the bregma-lambda axis horizontal. After shaving the hair and exposing the skull surface, the mouse was implanted with two 24-gauge stainless-steel guide cannulas, respectively, directing towards the right and left lateral cerebella (−6.4 mm caudal, ±1.5 mm lateral, −1.0 mm ventral from bregma) according to the stereotaxic coordinate of the mouse (Paxions 2001). The cannulas were fixed on the top of the skull by stainless steel screws and dental cement. The animal was allowed to fully recover after surgery for at least one week before the behavioral test was conducted.

On the day for behavioral tests, a 30-gauge injection cannula connected to a 1 µL hamilton syringe was inserted into the guide cannula for drug injection. The drug solution of 0.5 µL in each side was slowly infused with a microinfusion pump (kds311, kd scientific inc.) For 30 s with a further "hold" time for 60 s. The microinjection site was confirmed by the positive staining of trypan blue, which was injected through the cannula after behavioral tests. Data from mice with offsite injections were discarded.

Methamphetamine and apomorphine were dissolved in normal saline for i.p. And s.c. Injections, respectively. Tested compounds and haloperidol, when given by i.p. Injection, were dissolved in a vehicle containing 20% dmso, 20% Cremophor® el (polyoxyethylene castor, sigma-aldrich) and 60% normal saline. Furosemide was dissolved (20 nmole/ µL) in dimethylsulfoxide for intra-cerebellar microinjection the i.p. or s.c. Injection volume was 10 mL/kg.

The Migraine Model: Capsaicin (i.c.)-Induced Neuronal Activation in the TCC

Intra-cisteral instillation of capsaicin. Under anesthesia with chloral hydrate (400 and 100 mg/kg, i.p., respectively, for inducing and maintaining), the rat received a midline skin incision from the occipital protuberance to the upper cervical area. After catheterization with a catheter (PE-10, SIMS Portex Ltd, Hythe, UK) inserted 3 mm deep into the cisterna magna, the rat was placed in a prone position for 6 h. Then, the capsaicin solution (10 nmol, 100 µL) was instilled through the catheter into the cisterna magna over 1 min. The rat was then placed in a reverse Trendelenburg position (−30 degrees) for 30 min in order to facilitate capsaicin distribution within the subarachnoid space, followed by the prone position for another 90 min. Capsaicin (Sigma Chemical, St. Louis, Mo., USA) was dissolved in the vehicle solution containing 10% ethanol and 10% Tween 80, and sonicated for 5 min, and then further diluted (1:100) in normal saline as a stock solution stored at 4° C. For the control group, 100 µL of the vehicle was administered by i.c. instillation. Valproic acid at the dosage of 30 and 100 mg per kg or topiramate at 10, 30, and 100 mg per kg, dissolved in normal saline, were given at 30 min before caspsaicin administration for pretreatment.

TCC brain sections. Two hours after capsaicin instillation, the rat was euthanized by an overdose of chloral hydrate (1.6 g/kg, i.p.) and then perfused via the ascending aorta with 150 mL 0.5% sodium nitrate, followed by a 500 mL fixative containing paraformaldehyde (4%) in 0.1 M phosphate buffer (PB, pH 7.4). The brainstem with attached cervical cord was dissected, stored overnight in the perfusion fixative, and then dehydrated with 20% and 30% sucrose, in series. Brainstem and upper cervical spinal cord sections (50 µm) were serially sectioned using a cryostat (LEICA CM3050S, Nussloch, Germany) from 1 mm rostral to the obex to the C6 level of the spinal cord.

Immunohistochemistry of c-Fos protein in TCC sections. Free-floating immunohistochemistry of c-Fos protein was conducted using the avidin-biotin method. Briefly, TCC sections were incubated in 1% NaBH4 in 0.1 M PB for 20 min, rinsed thrice with 0.1 M PB for 10 min, and treated with 0.5% hydrogen peroxide in 0.1 M PB for 30 min. The sections were then washed thrice with 0.1 M PB for 10 min, followed by 1 hour incubation with 0.1 M PB containing 5% goat serum and 0.2% triton X-100. The sections were incubated with an anti-c-Fos rabbit polyclonal antibody (Calbiochem, San Diego, Calif., USA.) in 1:7000 dilution with 0.1 M PB containing 5% goat serum and 0.2% triton X-100 at 4° C. for 48 h. After a 10-min rinse with 0.1 M PB thrice, the sections were incubated with biotinylated anti-rabbit IgG (Vector Labs, Burlingame, Calif., USA) in 1:200 dilution with 0.1M PB containing 5% goat serum and 0.2% triton X-100 for 2 h at room temperature. The sections were then washed thrice with 0.1 M PB for 10 min and incubated with horseradish peroxidase avidin D (Vector Labs, Burlingame, Calif., USA) in 1:500 dilution with 0.1M PB containing 5% goat serum and 0.2% triton X-100 for 1 h in the dark at room temperature. Immunoreactions were visualized using the DAB Reagent kit (KPL, Gaithersburg, Md., USA).

Measurement of the total number of C-fos-ir neurons in the TCC. C-Fos-ir neurons, i.e., neurons with stained nuclei, were counted under a microscope (Olympus BX51, Essex, UK) by an observer blinded to the treatment group. Data were confirmed in randomly selected sections by a second investigator who was also blinded to the treatment group. The total number of c-Fos-ir TCC neurons were estimated based on the formular derived in our previous study (Fan et al., 2012): $16(N1+N2)/2+53(N2+N3)/2$, where N1, N2, and N3 were the c-Fos-ir neuronal numbers measured at 0.6, −1.2, and −9 mm from the obex, respectively.

Example 3

Figure 4:
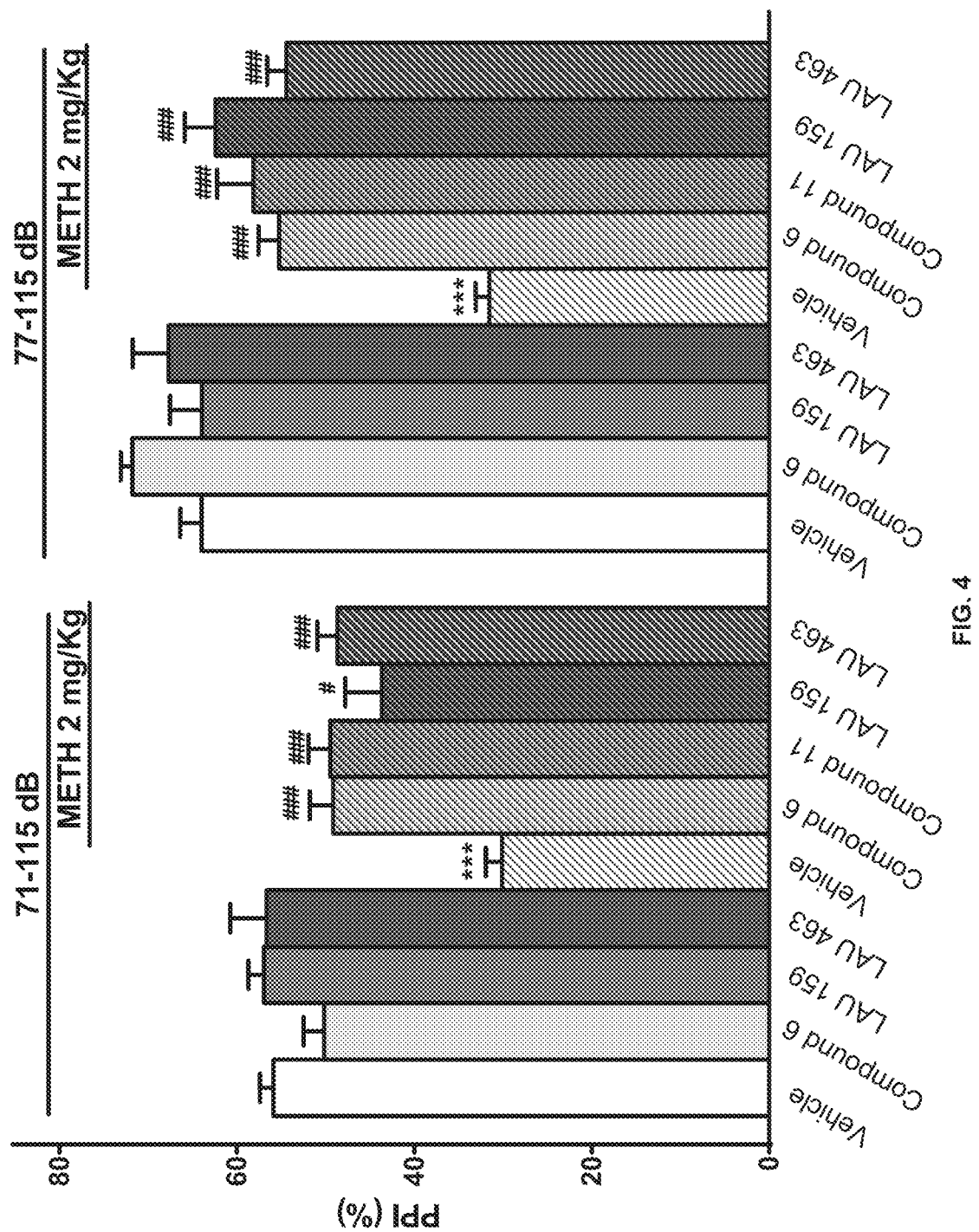
FIG. 4. Effects of Compound 6, LAU 159, LAU 463 and Compound 11, examples of positive allosteric modulators (PAMs) selective to α6GABARs, on the impairment of prepulse inhibition of the startle reflex (PPI) induced by methamphetamine (METH). The magnitudes of PPI in the startle response to a 115 dB acoustic stimulation paired with a prepulse of 71 dB (71-115 dB) or 77 dB (77-115 dB) ahead in 120 ms were measured as describe in Materials and Methods. Mice were pretreated with the tested compound 10 mg/kg (i. p.) or vehicle for 15 min followed by methamphetamine (METH, 2 mg/kg, i. p.) for 10 min. Tested compounds were dissolved in a vehicle containing 20% DMSO, 20% Cremophor® EL (polyoxyethylene castor, Sigma-Aldrich) and 60% normal saline. ***$p<0.001$ vs. the Vehicle without METH group; #$p<0.05$, ####$p<0.001$, vs. the Vehicle with METH group with the 71-115 dB or 77-115 dB protocol (Student's t test). N=6.
Figure 5:
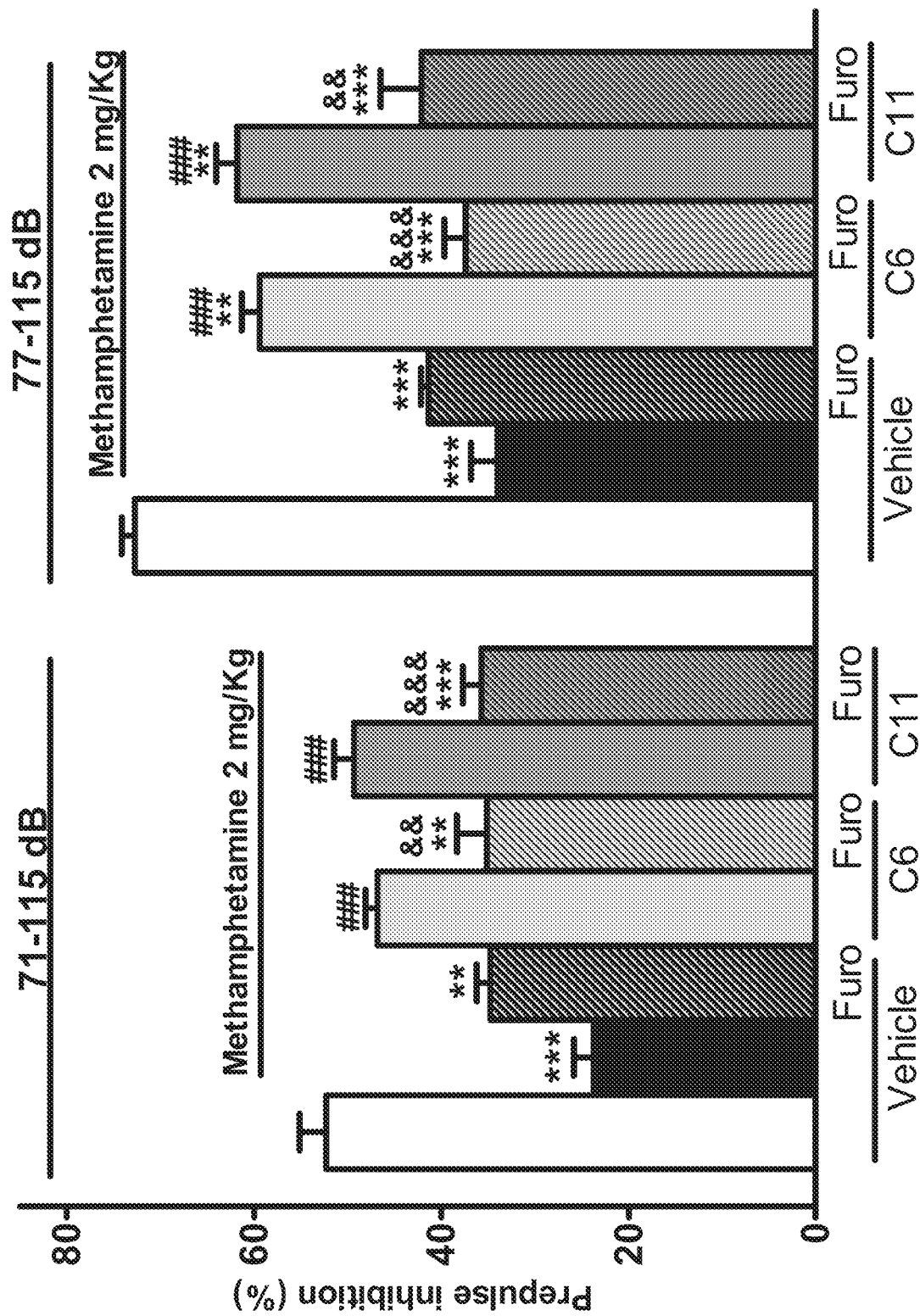
FIG. 5 is a graph showing that Compounds 6 (C6) and Compound 11 (C11) when given by i.p. injection at 10 mg/kg significantly rescued METM-impaired PPI. Effects of both compounds were prevented by intra-cerebellar microinjection of furosemde (10 nmol), a α6GABA$_A$R antagonist. The measurement and analyses of PPI impairment are the same as in FIG. 4. ***$p<0.001$ vs. the Vehicle without METH group; ####$p<0.001$, vs. the Vehicle with METH group; &&$p<0.01$, &&&$p<0.001$ vs. the C6 with METH group.

Effects of α6-Selective Pyrazoloquinolinones in an Animal Model Mimicking Neuropsychiatric Disorders with Sensorimotor Gating Deficit We first examined the effects of two pyrazoloquinolinone compounds on the impairment of PPI induced by METH, an animal model mimicking neuropsychiatric disorders with sensorimotor gating deficit. The compounds were compound 6 (7-methoxy-2-(4-methoxyphenyl)-2Hpyrazolo[4,3-c]quinolin-3(5H)-one) that selectively modulates α6-containing receptors, and compound 11 (8-chloro-2-(4-methoxyphenyl)-2Hpyrazolo[4,3-c]quinolin-3(5H)-one) that also modulates α6-containing receptors to an even higher extent but in addition strongly modulates other $GABA_A$ receptor subtypes. We found that both compounds 6 and 11 when given by i.p. injection at 10 mg/kg significantly rescued ME™-impaired PPI (FIG. 4). Furthermore, the inhibition of this beneficial effect by furosemide provides strong evidence for the involvement of α6-containing receptors, because furosemide is an α6-preferring $GABA_A$ receptor negative modulator (FIG. 5).

Example 4

Compounds with Improved Metabolic Properties Based on "Compound 6"

Figure 21:
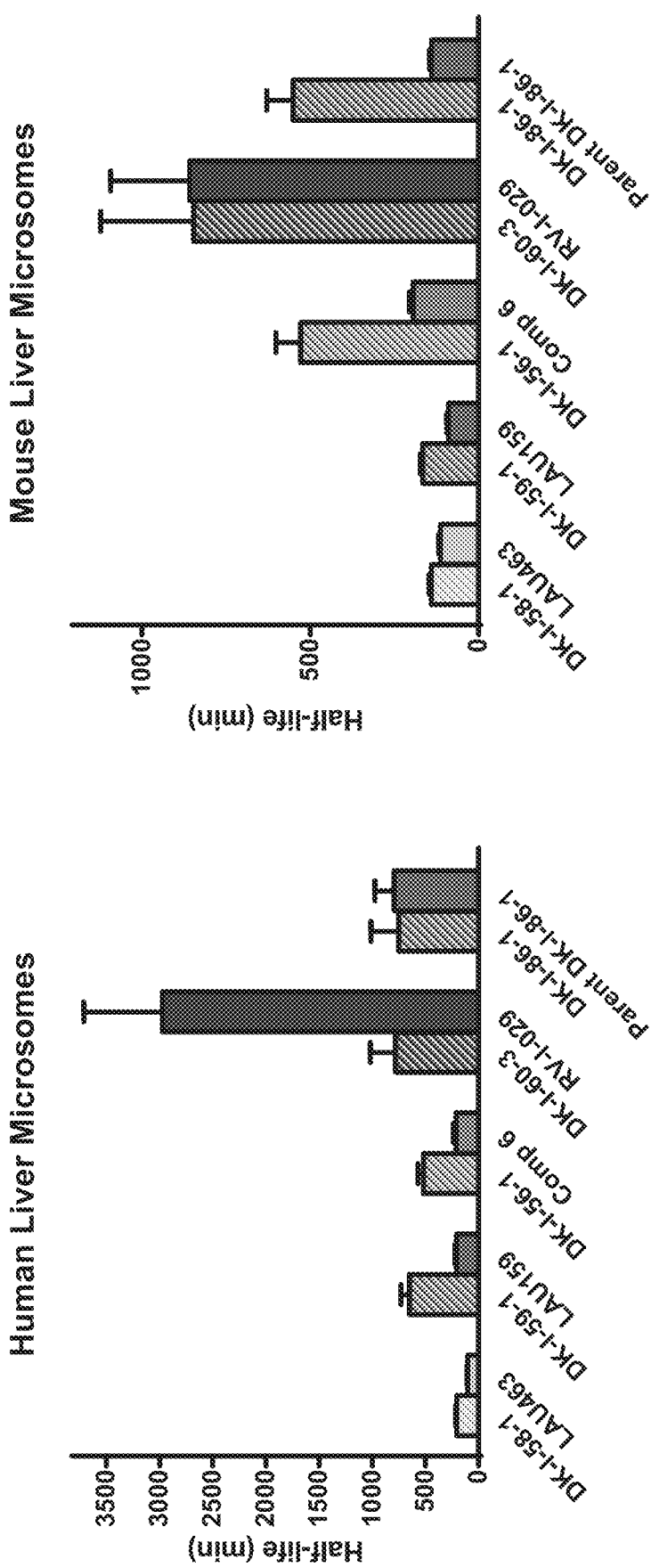
FIG. 21 is a graph of the half-life of compounds in human liver microsomes and mouse liver microsomes.
Figure 22:
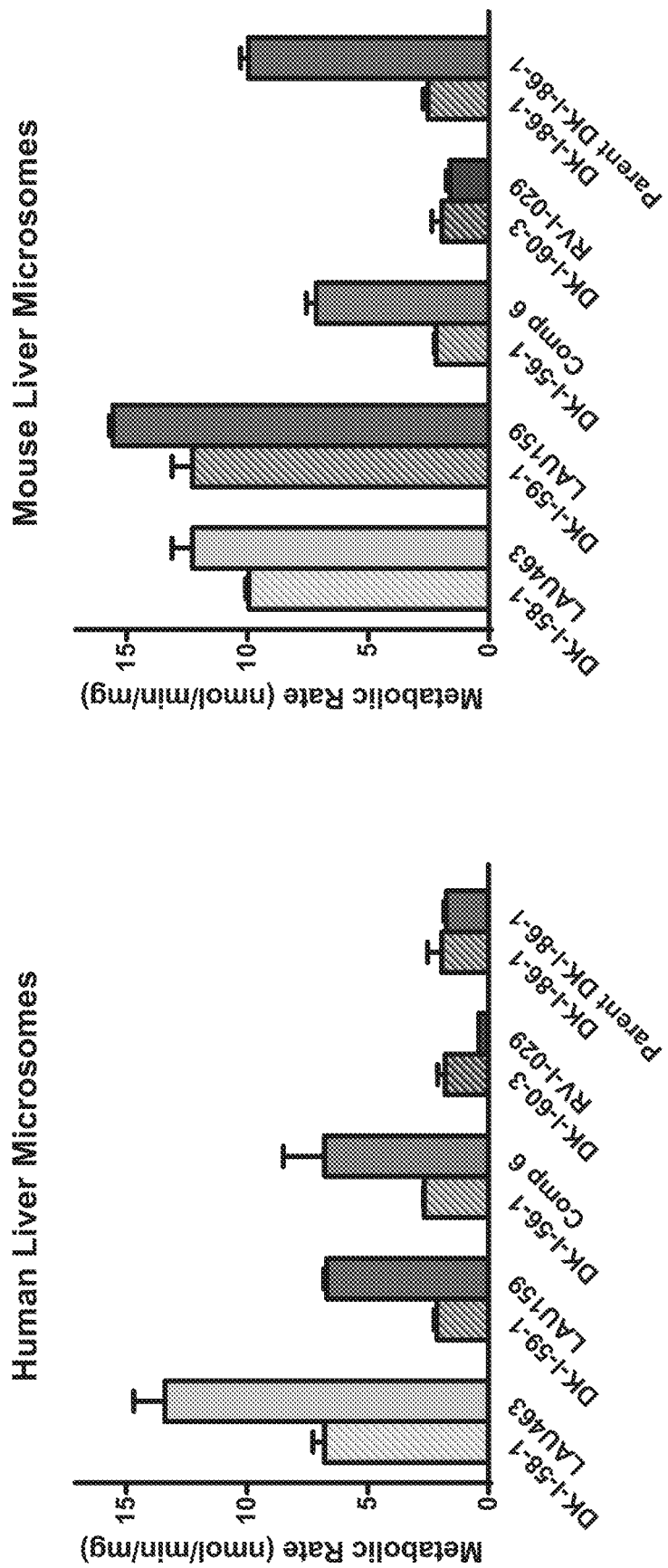
FIG. 22 is a graph of the metabolic rate of compounds of human liver microsomes and mouse liver microsomes.

Metabolic pathways that may disrupt the activity of compounds with aryl methoxy groups were investigated. It was found that deuterated analogs greatly enhanced the half-life of compounds in rat and human liver microsomes. Compound 6 was found to have a half-life of 175 minutes while the deuterated analog RV-I-29 has a half-life of >3000 minutes. This finding is crucial as drugs with a high rate of metabolism likely have a significantly shorter window of activity in vivo (FIG. 21).

Deuterated analogs of compound 6 (including 1-29 and DK-56-1) were tested in the same PPI model as above and found to have similar activity to the non-deuterated analog (FIG. 6), however duration of drug was not tested in these experiments. Experiments to test duration of the drug in vivo are currently underway.

Example 5

Additional α6 Selective Pyrazoloquinolinones

FIG. 4 shows that LAU 463 and LAU 159 displayed a comparable rescue effect as Compound 6 in METH-impaired PPI.

Example 6

Search for Water Soluble α-6 Bz/GABA-A Receptor Selective Ligands

Compound 5 and compound 6 were identified as selective α6β3γ2 receptors. Many different analogues of compound 6 were synthesized and screened to increase the water solubility of the compounds to facilitate their application in vivo.

Compounds were pharmacologically tested for selective activity for α6-subunit-containing receptors.

Several of the compounds exhibited increased water solubility and were investigated for their receptor subtype-selectivity. The ligands screened were sufficiently potent for testing their effectiveness in various animal models of CNS disorders. More potent and soluble candidates that are α6β3γ2 GABA-A receptor selective will be developed. These compounds may be used to develop new therapies for various CNS diseases.

Example 7

Solubility of Compounds

The solubility of the compounds was examined by sonicating 2 mg of each respective compound in 2 mL of DI water at 60° C. for 2 hours. Solutions were cooled to room temperature and then filtered using a syringe filter. The resultant solutions were injected into a mass spectrometer using a SIM method, calibrated to the respective retention times and mass units of each compound. Calibration curves using standard solutions (5 data points) of each compound dissolved in methanol were used to calculate the unknown aqueous concentrations of each compound. The solubilities of the compounds are shown in TABLE 1.

TABLE 1

Solubility of compounds.

OCD3 Compounds

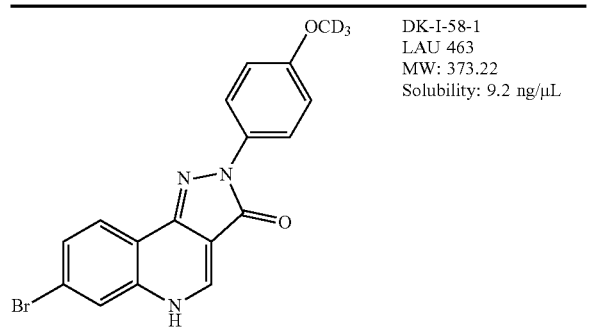

DK-I-58-1
LAU 463
MW: 373.22
Solubility: 9.2 ng/μL

TABLE 1-continued

Solubility of compounds.

OCD3 Compounds

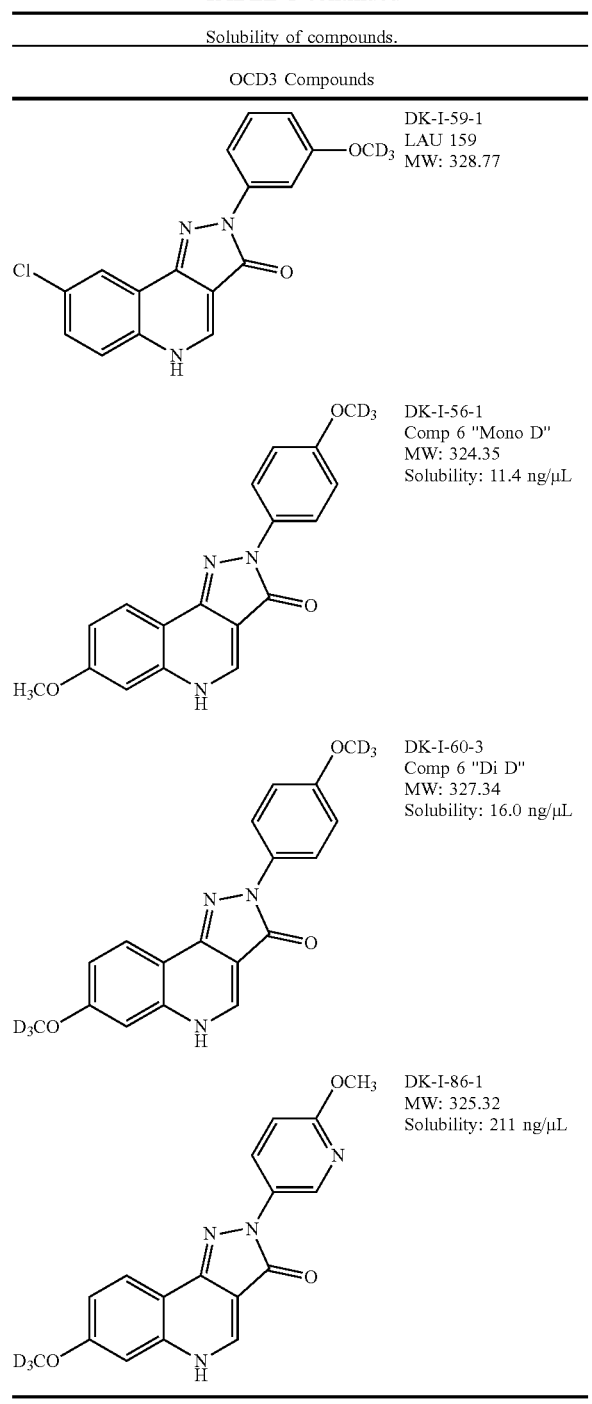

DK-I-59-1
LAU 159
MW: 328.77

DK-I-56-1
Comp 6 "Mono D"
MW: 324.35
Solubility: 11.4 ng/μL

DK-I-60-3
Comp 6 "Di D"
MW: 327.34
Solubility: 16.0 ng/μL

DK-I-86-1
MW: 325.32
Solubility: 211 ng/μL

Example 8

Electrophysiological Experiments with *Xenopus* Oocytes

Mature female *Xenopus laevis* (Nasco, Fort Atkinson, Wis., USA) were anaesthetized in a bath of ice-cold 0.17% Tricain (Ethyl-m-aminobenzoat, Sigma-Aldrich, St. Louis, Mo., USA) before decapitation and transfer of the frog's ovary to ND96 medium (96 mM NaCl, 2 mM KCl, 1 mM MgCl2, 5 mM HEPES; pH 7.5). Following incubation in 1 mg/mL collagenase (Sigma-Aldrich, St. Louis, Mo., USA)

for 30 min, stage 5 to 6 oocytes were singled out of the ovary and defolliculated using a platinum wire loop. Oocytes were stored and incubated at 18° C. in NDE medium (96 mM NaCl, 2 mM KCl, 1 mM MgCl2, 5 mM HEPES, 1.8 mM CaCl$_2$); pH 7.5) that was supplemented with 100 U per mL-1 penicillin, 100 µg per mL-1 streptomycin and 2.5 mM pyruvate. Oocytes were injected with an aqueous solution of mRNA. A total of 2.5 ng of mRNA per oocyte was injected. Subunit ratio was 1:1:5 for αxβγ2 (x=1,2,3,5) and 3:1:5 for α4/6β3γ2 and αβδ receptors. Injected oocytes were incubated for at least 36 h before electrophysiological recordings. Oocytes were placed on a nylon-grid in a bath of NDE medium. For current measurements, the oocytes were impaled with two microelectrodes (2-3MΩ), which were filled with 2 M KCl. The oocytes were constantly washed by a flow of 6 mL per min-1 NDE that could be switched to NDE containing GABA and/or drugs. Drugs were diluted into NDE from DMSO solutions resulting in a final concentration of 0.1% DMSO. Maximum currents measured in mRNA injected oocytes were in the microampere range for all receptor subtypes. To test for modulation of GABA induced currents by compounds, a GABA concentration that was titrated to trigger 3-5% of the respective maximum GABA-elicited current of the individual oocyte (EC3-5) was applied to the cell together with various concentrations of tested compounds. All recordings were performed at room temperature at a holding potential of −60 mV using a Warner OC-725C TEV (Warner Instrument, Hamden, Conn., USA) or a Dagan CA-1B Oocyte Clamp or a Dagan TEV-200A TEV (Dagan Corporation, Minneapolis, Minn., USA). Data were digitized using a Digidata 1322A or 1550 data acquisition system (Axon Instruments, Union City, Calif., USA), recorded using Clampex 10.5 software (Molecular Devices, Sunnyvale, Calif., USA), and analyzed using Clampfit 10.5 and GraphPad Prism 6.0 (La Jolla, Calif., USA) software. Concentration-response data were fitted using the Hill equation. Data are given as mean±SEM from at least three oocytes of two batches.

For selected test compounds full dose response curves were recorded in α1-6β3γ2 receptors. For selected compounds, dose response curves in additional receptor subtypes (α1,4,6β3δ, α6β1,2γ2, α1-6β3) were also obtained. For a wider panel of compounds, a two point screening pharmacology was obtained at 1 and 10 µM compound concentrations.

Figure 2:
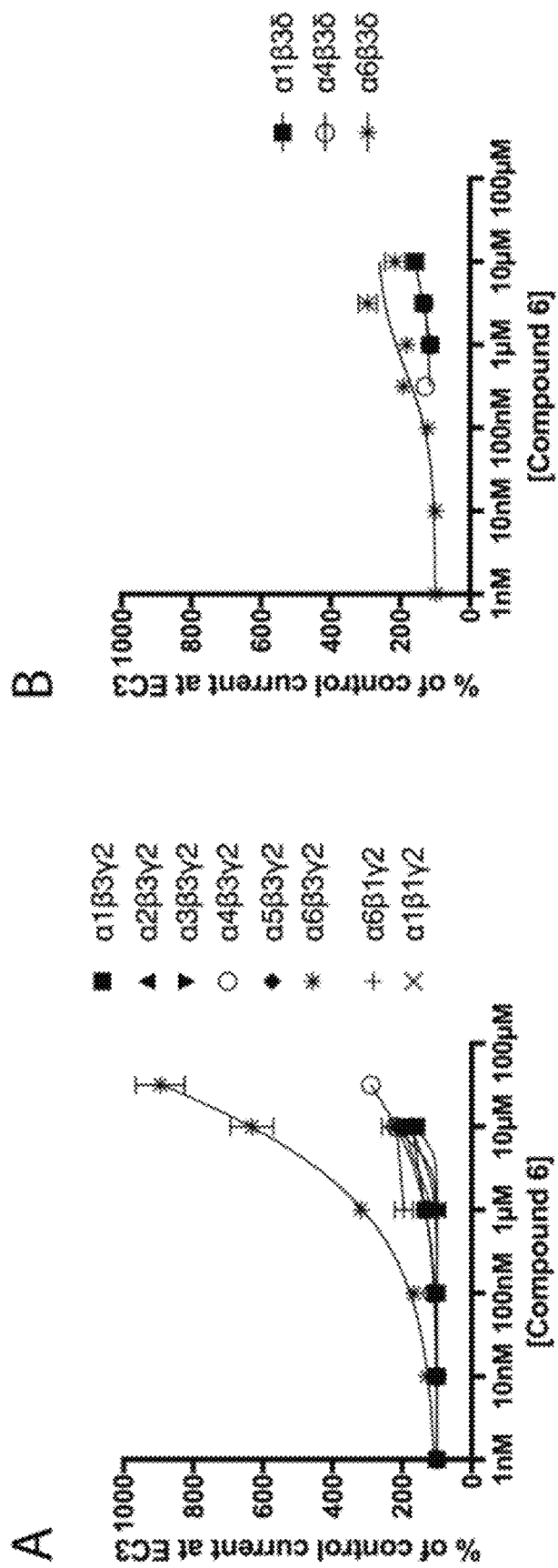
FIG. 2. Dose response curves of the change of GABA EC3 currents (modulation, referenced to 100% for the EC3 current) by increasing compound concentrations in the indicated receptor subtypes. A, C, E: Compound 6, LAU 463, and LAU 159 preferentially modulate GABA currents of α6β3γ2 receptors compared to the corresponding α1,2,3,4,5β3γ2 receptors. B, D, F: Measurements in the α1,4,6β3δ receptors (α1,4,6 are the major subunits that co-assemble with the delta subunit) indicate that compound 6 and LAU 159 also preferentially modulate the α6μ3δ receptor, compared to those containing α1 or α4 subunits. LAU 463 exerts similar effects on all three tested delta-containing receptors that are much smaller than those in the α6β3δ receptor.
Figure 2:
Figure 2:
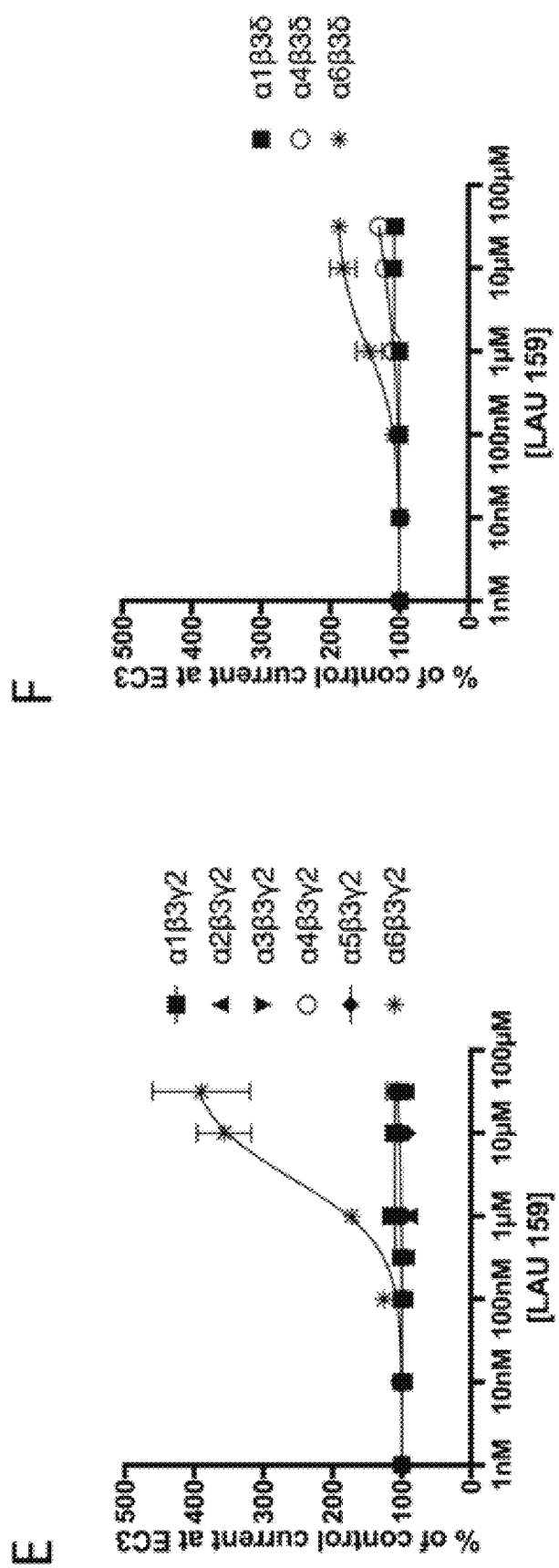
Figure 3:
FIG. 3. A: Dose response curve of the modulation of GABA EC3 (100%) currents by increasing DK-I-86-1 compound concentrations in the α6β3γ2 receptor. Other subtypes were investigated only at 1 and 10 μM to test selectivity. DK-I-86-1 preferentially modulates α6β3γ2 receptors. B: Receptor potentiation in the α6β3δ receptor by DK-I-86-1, note that due to low currents of these receptors it was measured at EC20 and thus appears smaller, however, data indicate that this receptor pool also is modulated.

Compounds were grouped into "parent compounds" (the pyrazoloquinolinones "compound 6", LAU 463, LAU 159, and LAU 165); their deuterated derivatives; and compounds with novel chemotypes. Compound 6, LAU 463, and LAU 159 all displayed among αβγ2 receptors a pronounced selectivity for the α6β3γ2 receptor, and modulated EC3-6 GABA currents strongly with maximum efficacies ranging from ~400% (LAU 159) to ~1000% enhancement of the reference current (FIG. 2 and FIG. 3). In α1,4,6β3δ receptors, they also display α6 preference, but displayed lower efficacy (below 400% at our experimental conditions) (FIG. 2 and FIG. 3).

The primary objectives of the large functional screening shown in FIG. 24 were the following:

(1) Test whether deuterated analogues are as active as the parent compounds in the receptor of interest, the α6β3γ2 receptor. This was the case (within the low precision of the method) for all deuterated compounds.

(2) Verify that the deuterated analogues were as selective as the parent compounds. For all deuterated analogues of these α6 preferring positive modulators we investigated effects at 1 and 10 µM in a series of screening experiments to determine if their efficacy and selectivity is comparable to the parent compounds (FIG. 24). Overall, we obtained satisfactory results for most deuterated analogues, i.e., they display activities very similar to their structural parents.

(3) Test new compounds and select them for further analysis if activity in the α6β3γ2 receptor was observed. Bioisosteric compounds with heteroatoms in the core scaffold and with analogous substituents as compound 6 (CW-03-030a and DK-I-86-1) were thus investigated. The reason for this is the poor solubility of pyrazoloquinolinones, which can be improved by introducing heteroatoms into the backbone of the heterocyclic core. Preliminary screening of CW-03-030a and DK-I-86-1 (FIG. 24) led to a follow up on the more promising DK-I-86-1. While maximum efficacy was lower than for the lead compounds, the selectivity was very good and if bioavailability is superior, the compound may be as good as or better than compound 6 for in vivo studies.

(4) Characterize candidate negative control compounds, which should be inactive in all receptors. Here we identified a putative negative control compound. LAU 165 and its deuterated analogue (DK-I-87-1) were inactive in all receptors that were tested so far (FIG. 24). Thus, these compounds can potentially be used in further in vivo studies as control compounds to demonstrate that inactive compounds of the same chemotype exist, and thus a specific substitution pattern is necessary for both in vitro and in vivo specific activity.

As shown in FIG. 24, in αxβ3γ2 receptors, the parent compounds compound 6, LAU 463 and LAU 159 and their deuterated analogues are (efficacy-) selective for α6β3γ2 receptors over the other αxβ3γ2 receptors. In binary αxβ3 (x=1,2,3,5) receptors, they display low efficacy as well. In β1-containing receptors, data suggests loss of α6-preferences, and increased activity in α1β1-containing receptors compared to α6β1-containing receptors. This observation needs follow up studies, see below.

LAU 165 and the deuterated analogue DK-I-87-1 were shown to be essentially inactive in all tested receptors.

Figure 17:
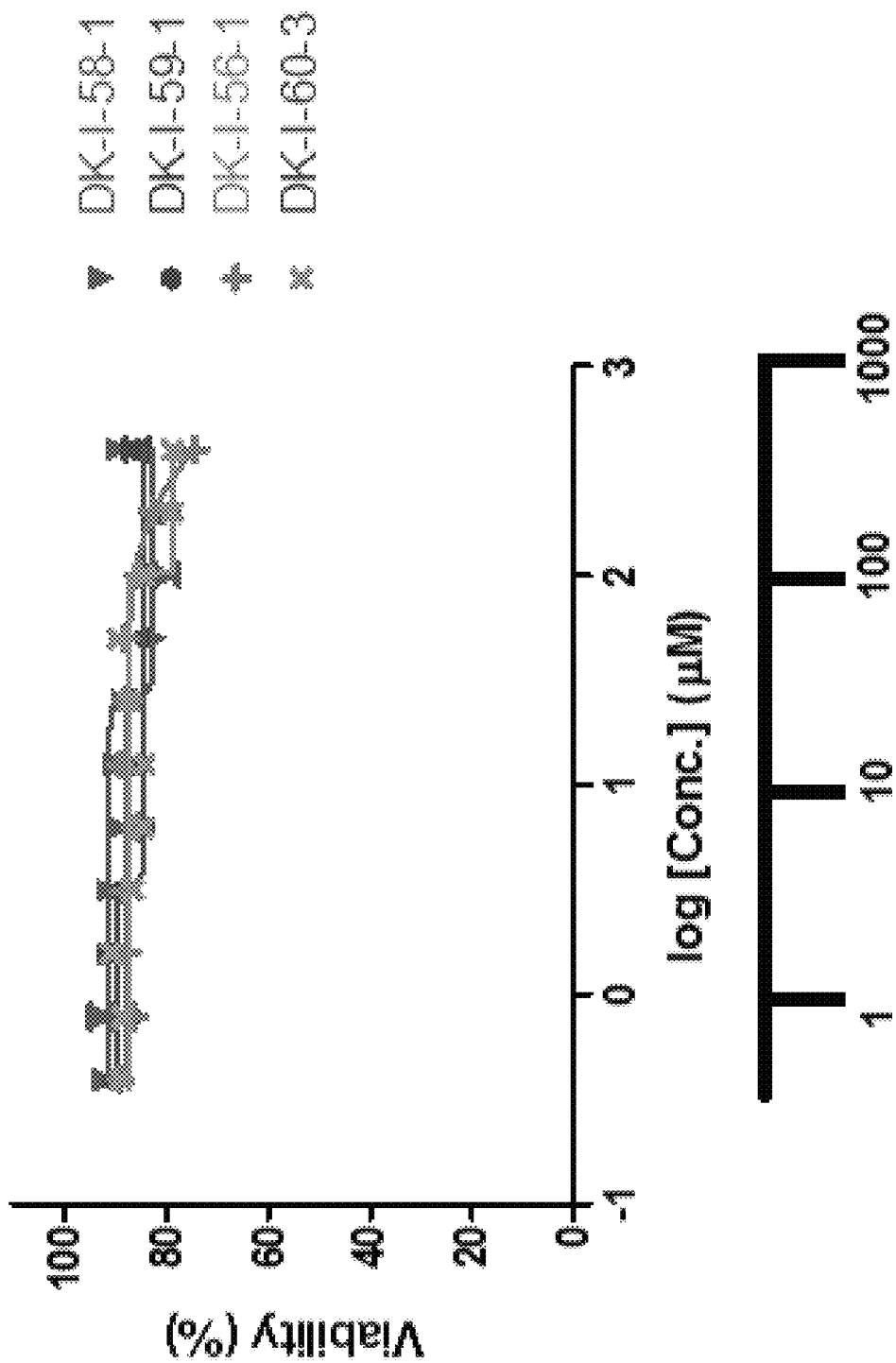
FIG. 17 is a graph of viability versus log[concentration] for cytotoxic analysis for various compounds.
Figure 18:
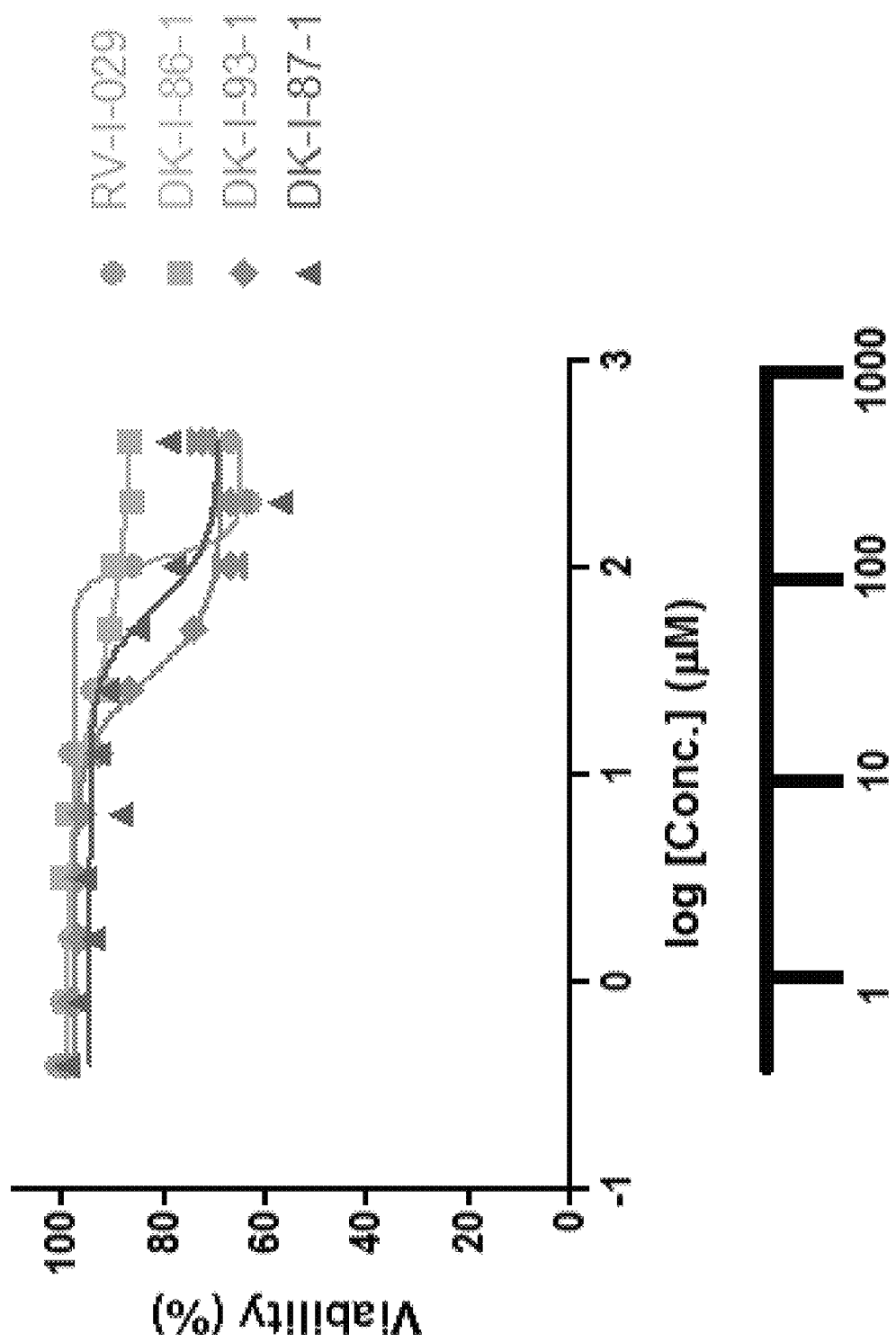
FIG. 18 is a graph of viability versus log[concentration] for cytotoxic analysis for various compounds.

Values at 100 nM and 1 µM reflect modulations that can be expected to occur in vivo, based on the brain free fraction concentrations that were determined (see FIGS. 17 and 18).

Additional pharmacological experiments. Selected compounds of those listed in FIG. 24, as well as additional compounds will be tested also in receptors subtypes containing the β1 and β2 subunits to investigate how alpha selectivity and beta selectivity combine together into a subtype specific response covering all three beta isoforms.

Furthermore, pharmacological testing in delta-containing receptors will also be conducted in more depth. The inactive compound DK-I-87-1 will be tested in co-application experiments with active compound DK-I-56-1 to clarify if it is a non-binder or a silent binder (null modulator) of the binding site used by DK-I-56-1. We keep the option to test selected compounds also in other cells, such as mammalian cells, expressing recombinant receptors if needed to substantiate any claims on efficacy or selectivity. We also optionally test in human recombinant receptors rather than the so far used rat receptors. Furthermore, selected compounds (preferentially these that are active in disease model experiments) can also conceivably be tested electrophysiologically in cultured neurons, or in slices of α6-expressing tissues such as cerebellum, cochlear nucleus, trigeminal ganglion, to study the effects of compounds on native receptors.

Additional experiments to evaluate effect of compounds at GABA$_A$ receptors in dorsal root ganglia: Dorsal root ganglia and trigeminal ganglia from naive and neuropathic pain model rats, where both trigeminal nerve lesions and ischiatic nerve lesions can be employed, will be prepared and worked up immunohistochemically and biochemically using antibodies directed against α6-subunits to explore the expression level of this subunit under normal and pathological conditions. In case that α6 subunits can be detected in dorsal root ganglia as well, follow up studies will be initiated to test effectiveness of the compounds in rodent models of neuropathic pain of spinal nerves.

Example 9

Effects of Subchronic Treatment with DK-I-56-1 in IoN-CCI Rats

Chronic constriction injury (CCI) is a common neuropathic pain model. The unilateral ligature of the infraorbital nerve (IoN) in rats, as an animal model of peripheral neuropathic pain, and more specifically, trigeminal neuralgia and trigeminal neuropathy, was performed as described by Desuere and Hans (Deseure et al. J. Vis. Exp. 2015, 103, e53167). Wistar rats (46 in total) were randomly assigned to one of four experimental groups and then were behaviorally tested in a blinded manner. For studying the effects of subchronic treatment with the nanoemulsion formulation of DK-I-56-1 in IoN-CCI rats, DK-I-56-1 (10 mg/kg i.p.) or its vehicle (placebo nanoemulsion i.p.) were injected daily for 14 consecutive days after surgery. Sham-operated rats were treated in parallel. By a procedure slightly modified from Djordjevic et al. (Int. J. Pharm. 2015, 493, 40-54), biocompatible nanoemulsions were prepared by high pressure homogenization at 50° C. They were composed of medium chain triglycerides, castor oil, soybean lecithin, sodium oleate, polyoxyethylensorbitan monooleate, butylhydroxytoluene, DMSO and ultra-pure water. Treatment was administered at 3:00 PM, after finishing the behavioral testing or handling/habituation for the given day. Two types of behavioral tests in single observation cages were performed repeatedly, on separate days. First, the response to the application of a graded series of three von Frey filaments onto ipsilateral vibrissal pad was measured on pre-operative days −3 and −1 and post-operative days 7, 14, 21, and 28. The response was categorized as score 0 (a complete lack of response), 1 (a stimulus detection), 2 (a withdrawal reaction), 3 (an escape/attack response), or 4 (asymmetric face grooming). The other parameter, face grooming during body grooming, was manually assessed during 10 min of recording on pre-operative day −2 and post-operative days 2, 4, 8, and 15 (i.e. after 1, 3, 7, and 14 applications of treatment). This parameter represents a reliable ethological measure to control for possible confounding by nonspecific treatment effects, such as sedation or motor impairment.

Figure 14A:
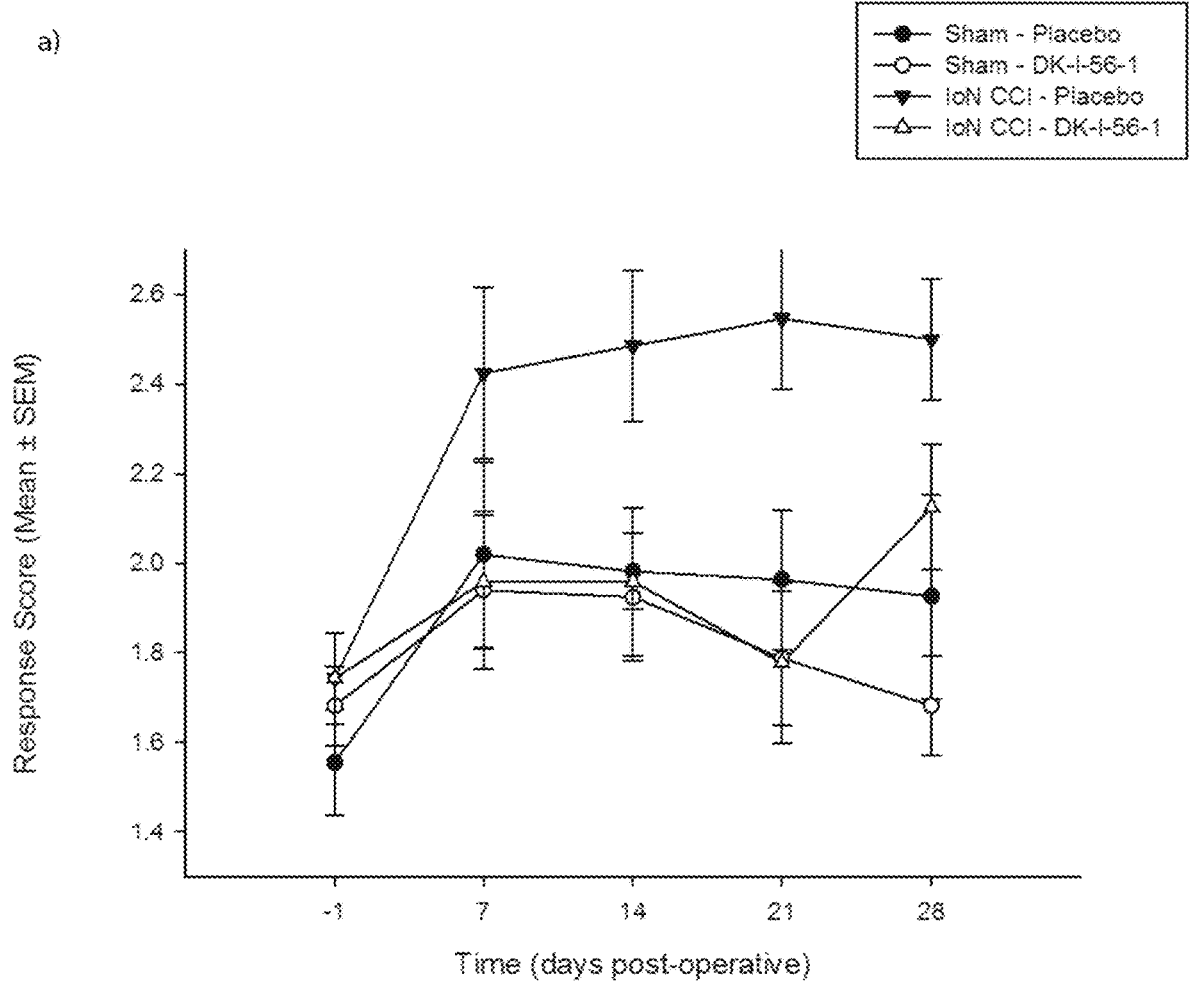
FIG. 14A shows the prophylactic antinociceptive effect of subchronic treatment with DK-I-56-1 in rats with unilateral chronic constriction injury to the infraorbital nerve (IoN-CCI), as assessed by von Frey filaments.
Figure 14B:
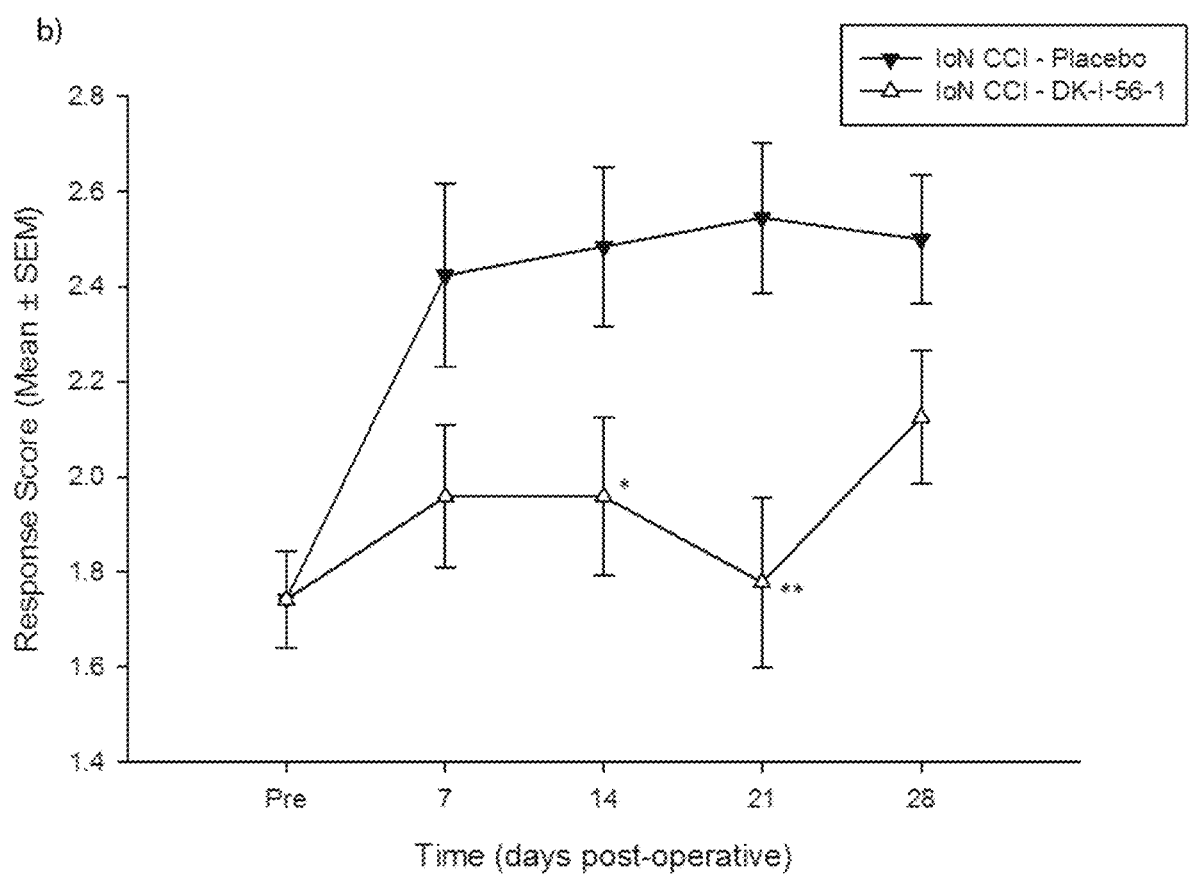
FIG. 14B represents the significances between the treatment (IoN-CCI—DK-I-56-1) and control group (IoN-CCI—Placebo) of operated animals. Each point is the mean±S.E.M. The number of analyzed animals for Sham—Placebo, Sham—DK-I-56-1, IoN-CCI—Placebo and Ion-CCI—DK-I-56-1 group was 9, 11, 11, and 12, respectively. *P<0.05 and **P<0.01 compared to IoN-CCI—Placebo group; two-way ANOVA on the data for the given day, followed by Student Newman Keuls post-hoc test. Further details are given in Example 10.

The results of the assessment of central neuropathic pain are summarized in FIG. 14A (response score to von Frey filament stimulation for all four groups) and FIG. 14B (only for clarity, response score for two groups of IoN-CCI rats). The criterion for exclusion of animals from statistical analyses was predefined for Ion-CCI—Placebo group (consistently decreased reactivity in post-surgery period when compared to the pre-surgery values; 1 animal excluded), and for Sham—Placebo group (consistently increased reactivity in post-surgery period when compared to the pre-surgery values, the mean difference being more than or equal 1.25 score points; 2 animals excluded); the animals treated with DK-I-56-1 could not have been excluded.

As shown in FIG. 14A, basal response scores (pre-operative day −1) were similar among four groups, while the scores of two IoN-CCI groups were virtually the same. Seven days after surgery and afterwards, the response score in the IoN-CCI—Placebo group was consistently increased, at the level of 2.4 score points and above, demonstrating a nociceptive response to the application of stimuli. Repeated treatment with DK-I-56-1 provided a preventive effect on the development of neuropathic pain, and this anti-allodynic effect was statistically significant on post-operative days 14 and 21. On the post-operative day 28, i.e. 14 days after the last dose of DK-I-56-1, the significance of the effect of DK-I-56-1 disappeared (FIG. 14B). Thus, DK-I-56-1 demonstrated a capability to be applied as a prophylactic measure for the management of neuropathic pain related to the impairment of branches of the trigeminal nerve.

Figure 15:
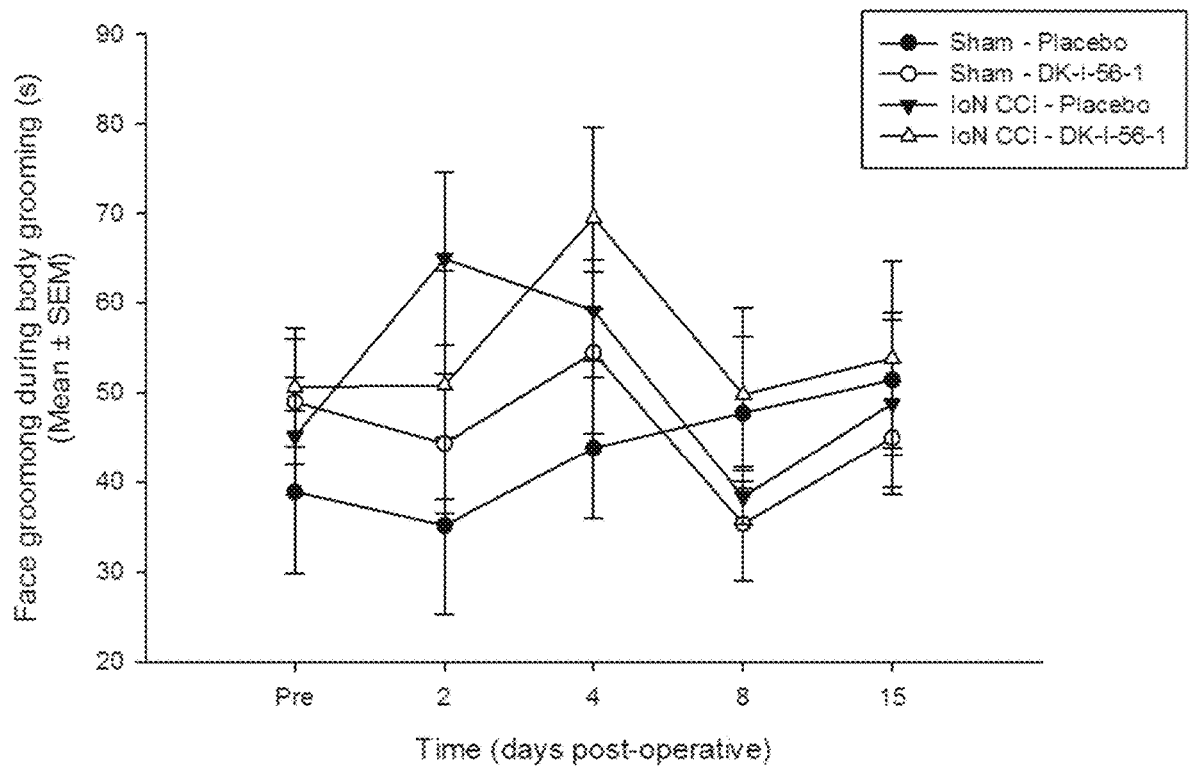
FIG. 15 shows the total time the rats spent in face grooming during body grooming during 10 min of recording. Further details are given in Example 10.
Figure 16A:
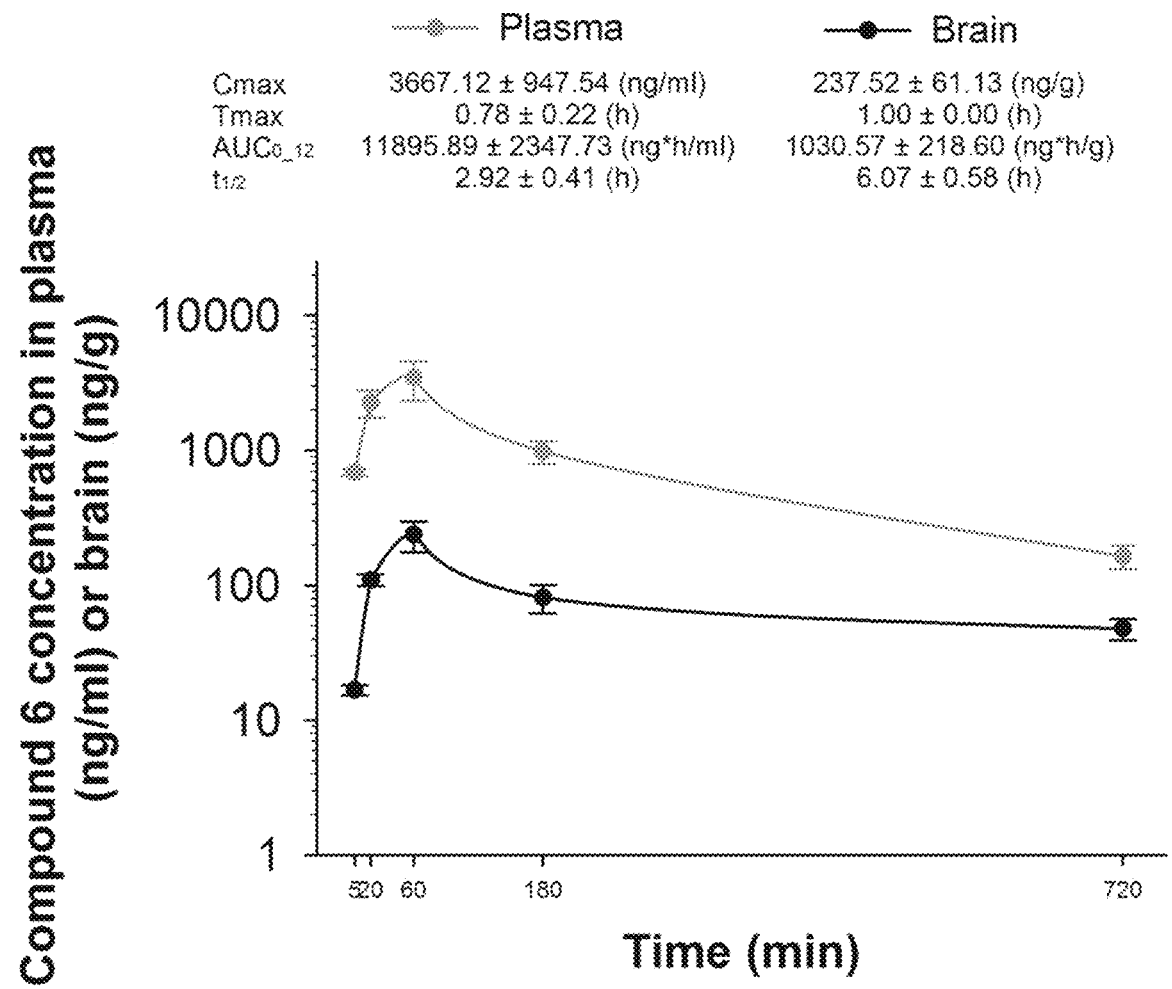
FIG. 16 are graphs (A)-(E) showing concentration-time curves for the plasma and brain levels, as well as the calculated pharmacokinetic parameters in plasma and brain for various compounds.
Figure 16B:
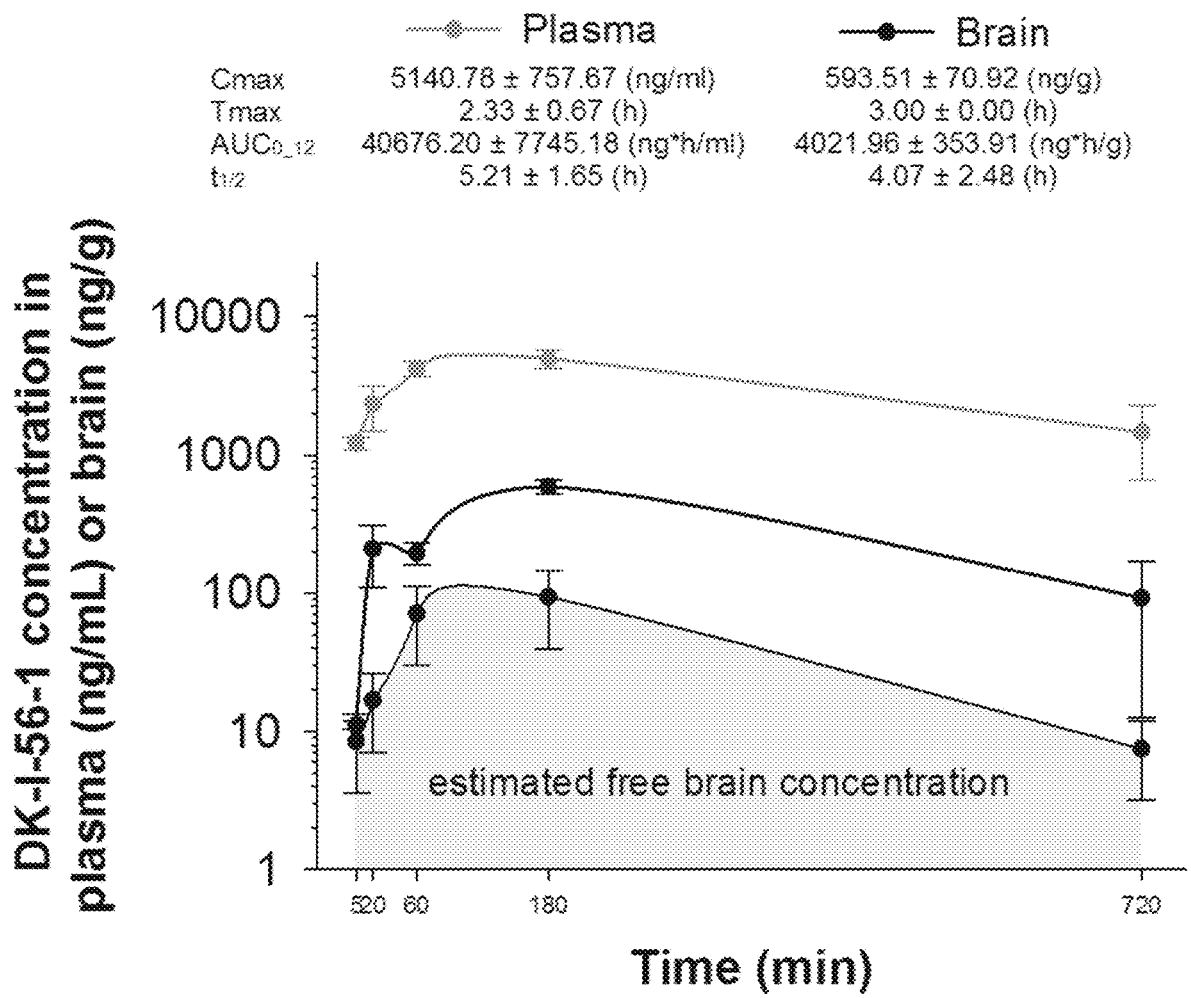
Figure 16C:
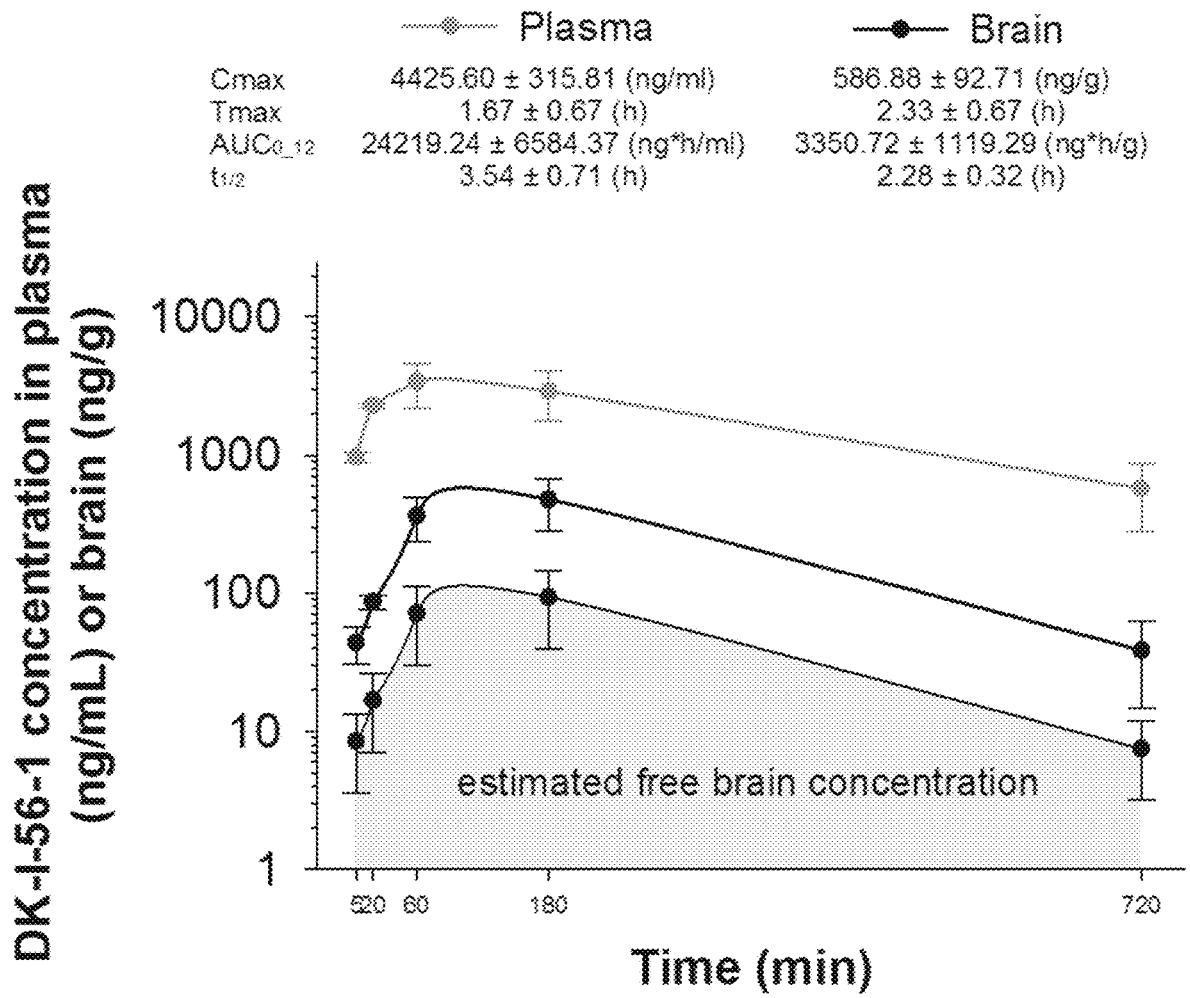
Figure 16D:
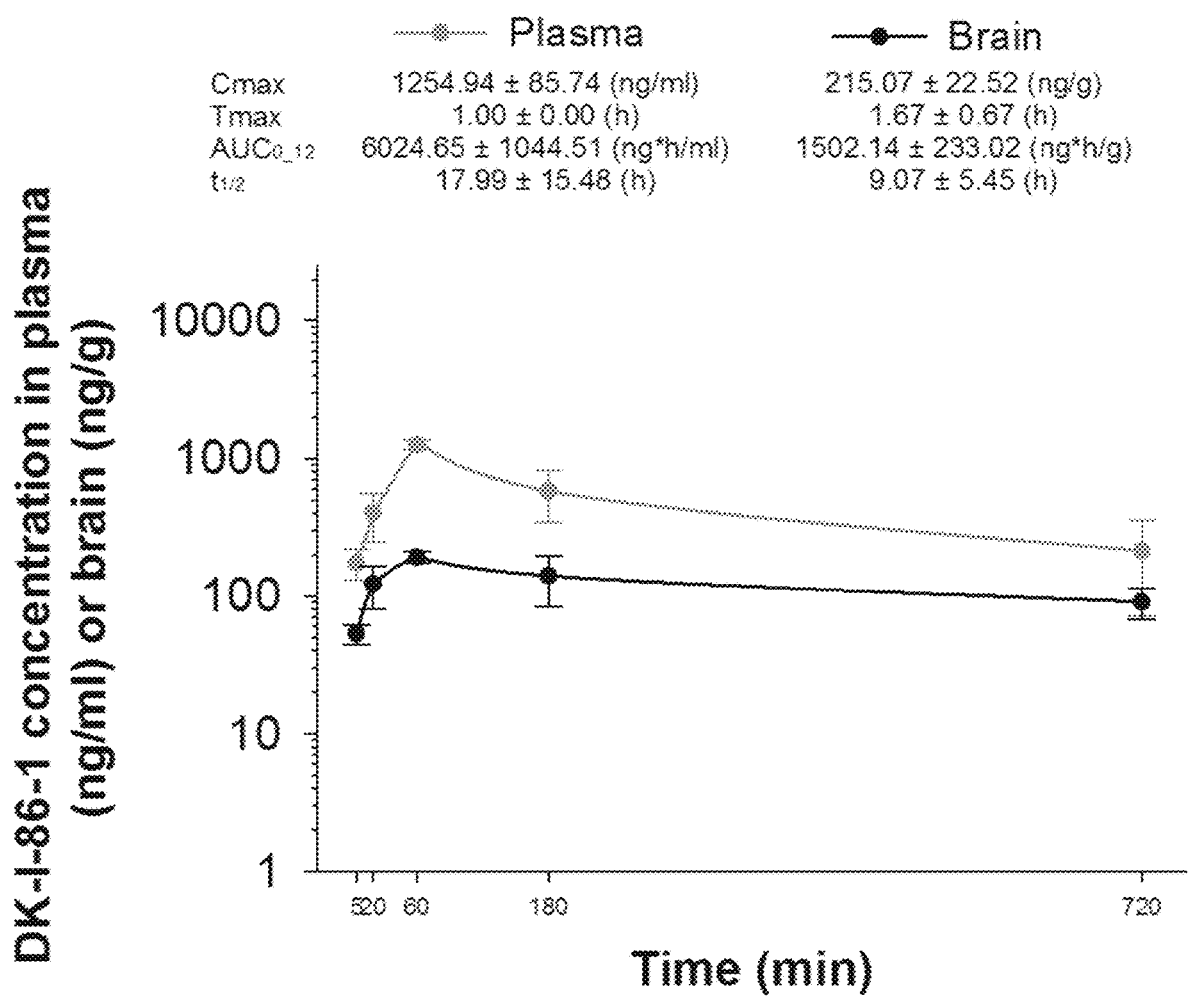
Figure 16E:
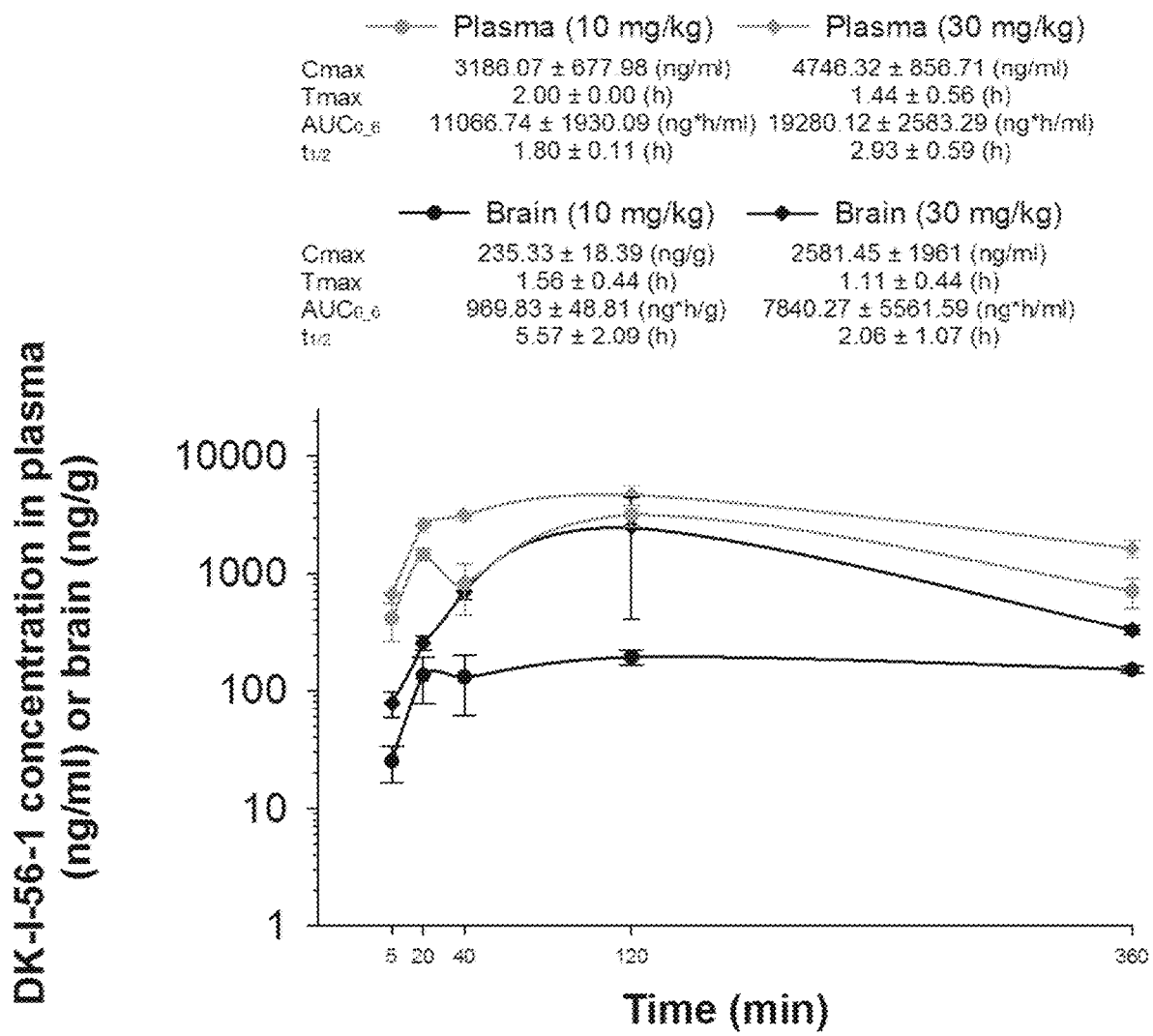

The results of the assessment of face grooming during body grooming, as a physiological manifestation of the rat's behavior on which IoN-CCI has little or no effect, are summarized in FIG. 15. The level of activity was distinct on all of the five days measured, and no significant differences among groups were detected. This parameter, characterized by a substantial variability, demonstrated the lack of sedation-like or motor-impairing influences of DK-I-56-1, at least at the time of behavioral testing. Moreover, in a separate pilot experiment, DK-I-56-1 acutely administered in the dose range 10-55 mg/kg did not impair rotarod performance of male Wistar rats when tested 20 min after treatment administration.

As trigeminal neuralgia and trigeminal neuropathy are chronic types of pain which usually require long-term pharmacotherapy, it is planned to perform an additional experiment, in male Wistar rats subjected exclusively to IoN-CCI. After assessment of the neuropathy (mechanical allodynia to von Frey filaments) on Day 21, the rats would be randomly assigned to three groups: placebo, DK-I-56-1, or DK-I-87-1, the compound inactive at α6-containing $GABA_A$ receptors. The respective treatment would be applied i.p. once daily during 14 days, starting on Day 21. Possible acute effects of the treatment would be estimated on Day 22, while the potential of eliciting chronic analgesic effects would be assessed on post-surgery days 28 and 35. Statistical analysis for each of measurement times would be performed by one-way ANOVA followed by Student Newman Keuls test.

Example 10

Pharmacokinetic Behavior of Compound 6, DK-I-56-1, and DK-I-86-1, in Rats and of DK-I-56-1 in Mice after an Acute Treatment with the Nanoemulsion and/or Suspension Formulation Five pharmacokinetic studies have been performed; four in male Wistar rats and one in male Swiss mice. In experiments in rats, single 10 mg/kg doses of compound 6, DK-I-56-1 or DK-I-86-1 were administered i.p. to three rats per each of five time points. At predetermined time intervals, i.e., 5, 20, 60, 180, and 720 min after dosing, the blood and brain samples of the rat were collected. In the experiment in mice, single 10 mg/kg or 30 mg/kg doses of DK-I-56-1 were administered i.p. to three mice per each of 5 time points. At predetermined time intervals, i.e., 5, 20, 40, 120, and 360 min, the blood and brain samples of the mouse were collected. In rats, two experiments, with compound 6 and DK-I-56-1, were carried out with the 2 mg/mL formulation of a nanoemulsion (as described in Example 10), given at an injection volume of 5 mL/kg. The other two experiments in rats, with DK-I-56-1 and DK-I-86-1, were performed with the suspension formulation, given at an injection volume of 2 mL/kg (the ligands were suspended with the aid of sonication in solvent containing 85% distilled water, 14% propyleneglycol, and 1% Tween 80). The experiment in mice was performed with the 2 mg/mL nanoemulsion formulation of DK-I-56-1. Concentration of compound 6, DK-I-56-1 or DK-I-86-1 extracted from the respective samples by solid phase extraction was determined by ultra-high performance liquid chromatography-tandem mass spectrometry (UHPLC-MS/MS). In a separate in vitro experiment, the rapid equilibrium dialysis assay was used to determine free fraction of DK-I-56-1 in rat plasma and brain tissue.

The results of the assessment of pharmacokinetic behavior of compound 6, DK-I-56-1 and DK-I-86-1 are summarized in FIG. 16-20, which represent concentration-time curves, measured as total concentration in plasma (ng/mL) and brain (ng/g), together with the calculated pharmacokinetic parameters in plasma and brain. In the case of DK-I-56-1 in rats (FIGS. 17 and 18), the estimated free concentrations in brain tissue were also presented.

To ease comparison between the concentrations obtained in vivo and those used in vitro, the description of the kinetic results refers to molar rather than weight concentrations. In rats, compound 6 (FIG. 16) and DK-I-86-1 (FIG. 19) reached high submicromolar concentrations in brain tissue. Such relatively low total brain concentrations attained after administration of the 10 mg/kg dose of compound 6 and DK-I-86-1 in a suspension cannot be solely ascribed to formulation issues, given that DK-I-56-1 reached micromolar concentrations in rat brain tissue after administration of the same dose of both, the nanoemulsion formulation (FIG. 17) and the suspension formulation (FIG. 18). While free fraction of DK-I-56-1 in rat blood is exceptionally low (below 0.5%), its free fraction in rat brain tissue equals 19.45%, which enables reaching pharmacologically relevant free concentrations in the range of 100 nM and above. With submicromolar total concentrations in mouse brain, kinetic behavior of DK-I-56-1 dosed at 10 mg/kg was less favorable for eliciting central nervous system effects in mice than in rats. Nonetheless, the maximum concentration of DK-I-56-1 attained in mouse brain after the dose of 30 mg/kg was as high as 7.5 µmol/L (FIG. 20); this value demonstrates the dose-dependency of brain tissue kinetics of this ligand. Moreover, brain tissue kinetics of DK-I-56-1 is relatively slow, especially in rats, with elimination half-life being approximately 4 h, and time of maximum concentration 3 h. It is worthy of noting that DK-I-86-1 had the longest half-life in rat brain tissue (approximately 9 h). It can be concluded that all four ligands reached substantial micromolar maximum concentrations in plasma of both, the rats and the mice, while their penetration into the central nervous system was slightly restricted, given the consistently moderately lower concentrations in brain when compared to those attained in plasma. Nevertheless, the kinetic studies in rodents have shown that these ligands, and especially DK-I-56-1, possess pharmacokinetic properties beneficial for the proposed neuropsychopharmacological application.

Example 11

Examination of α6-GABA-A Receptor as Target for Neuropsychiatric Syndrome

We found the intractable motor tics in a pediatric patient were subsided within 1 hour after taking the leaf extract of a local herb, Clerodendron inerme Gaertn (CI) (Fan et al., 2009). We then identified an active constituent, hispidulin, from the ethanol extract of Cl leaves, which is a positive allosteric modulator (PAM) of GABA-A receptors, including the α6 subunit-containing GABA-ARs (α6 GABA-ARs). Since hispidulin is not selective for α6 GABA-AR, we obtained the first selective α6 GABA-AR PAM, compound 6. Compound 6, like KLP-1, effectively rescued the impairment of prepulse inhibition of the startle response (PPI) induced by methamphetamine, a measurement of the sensorimotor gating function that is deficit in several neuropsychiatric disorders, including tic disorders and schizophrenia.

We further conducted a comprehensive study examining the effects of compound 6 in various behavioral models mimicking tic disorders, including the hyperlocomotion induced by methamphetamine (a dopamine releaser), stereotypy climbing behaviors induced by apomorphine (a dopamine receptor agonist). Using anatomical and pharmacological approaches by intracerebellar microinjection and pharmacological approaches using furosemide as a non-competitive antagonist and diazepam, that does not act at α63 g2 GABA-ARs, we also confirmed that α6 GABA-AR in the cerebellum is the action target of Compound 6 (FIG. 5).

Figure 7:
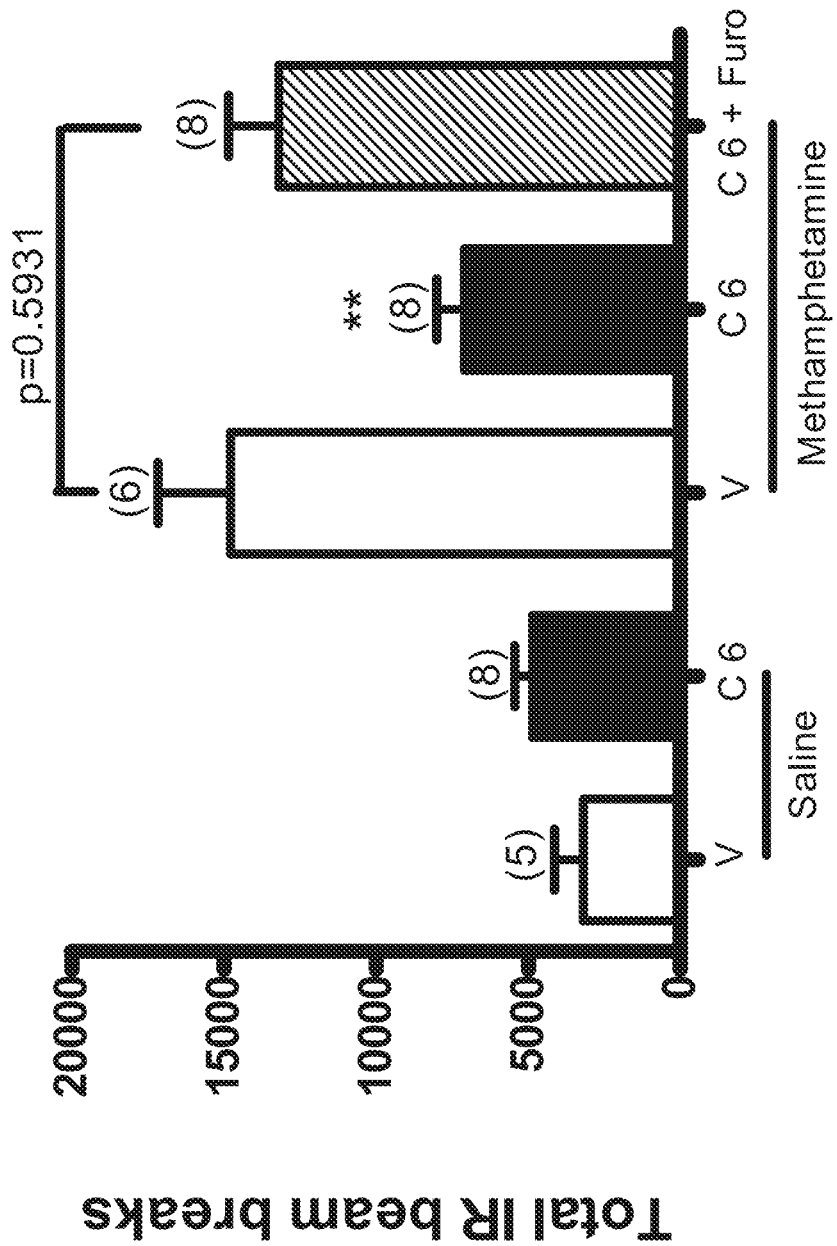
FIG. 7. Effects of Compound 6 on total IR beam breaks in mice under treatment with saline or methamphetamine (2 mg/kg, i.p.) for 60 min. Mice were pretreated with Compound 6 (C6, 3 mg/kg, i.p.) or vehicle (V), or Compound 6+furosemide (10 nmol, intra-cerebellar injection) for 10 min before METH/saline injection. The locomotor activity was measured by the number of infra-red (IR) beam interruptions in the open field chamber every 5 min. The ordinate is total IR beam interruptions recorded during the 60 min-METH treatment period. The number of animal tested in each group is denoted above each bar. **$p<0.01$ vs. the Vehicle with METH group (Student's t test).
Figure 8:
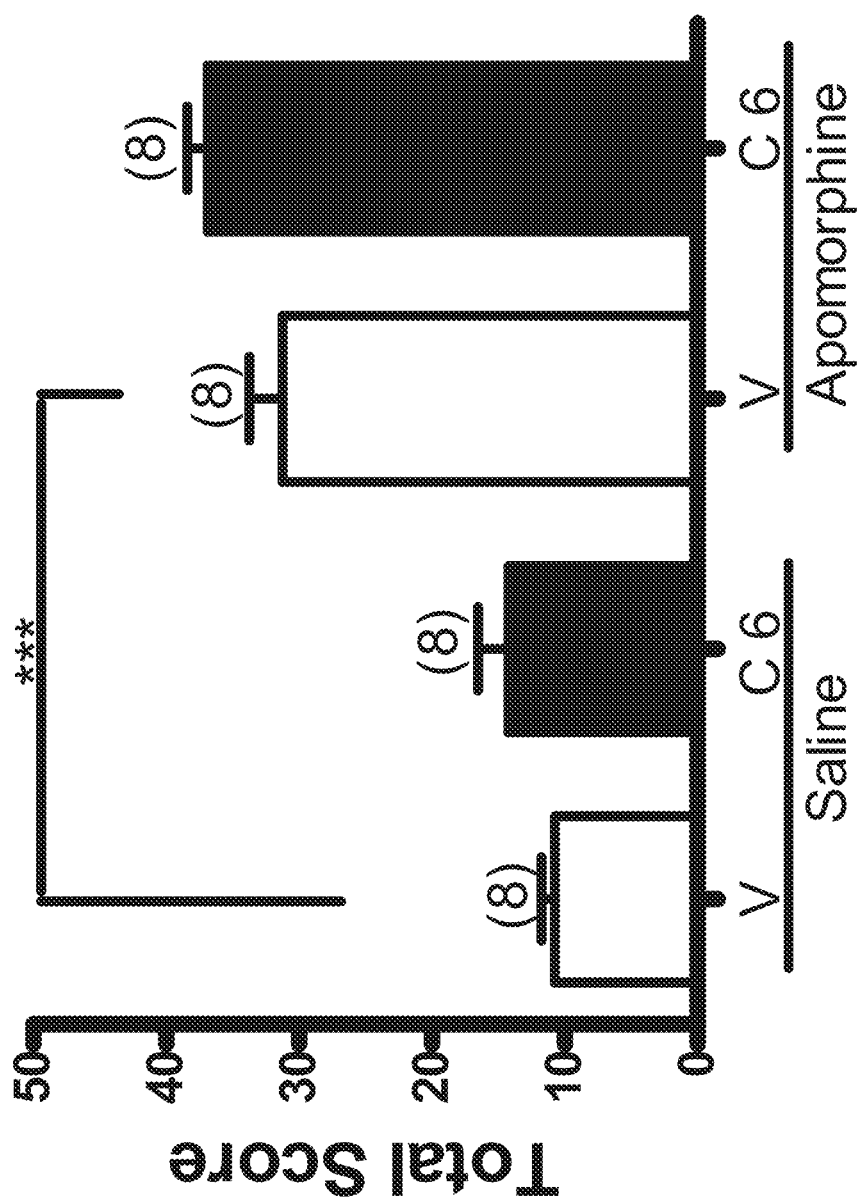
FIG. 8. Total scores of stereotypy behaviors after injection of apomorphine (1 mg/kg, s.c.) or normal saline in groups pretreated with Compound 6 (C6, 3 mg/kg, i.p.) or vehicle (V). Stereotypy climbing behaviors were scored as described in Materials and Methods every 5 min for 1 min before and after apomorphine injection. The ordinate is total scores recorded during the 45 min-apomorphine treatment period in different groups. ***$p<0.001$ vs. the Vehicle without apomorphine group (Student's t test).
Figure 9:
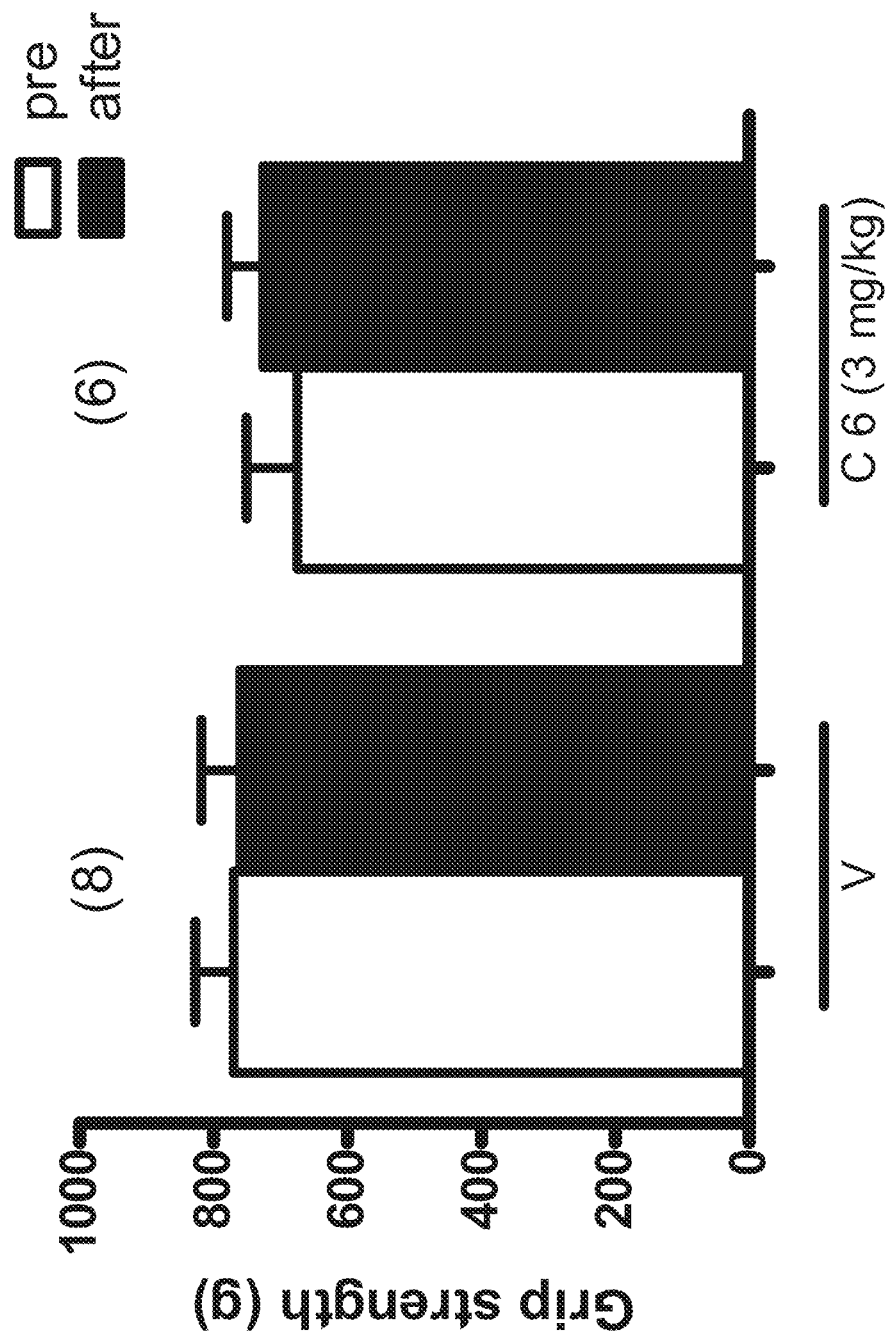
FIG. 9. Effect of Compound 6 on the grip strength (muscle power) of mice. The grip strength of forepaws of the mouse was measured by a grip strength meter three times every 2 min and averaged. The grip strength of the mouse was measured before (pre) or 15 min after treatment with Compound 6 (C6, 3 mg/kg) and vehicle (V).
Figure 10:
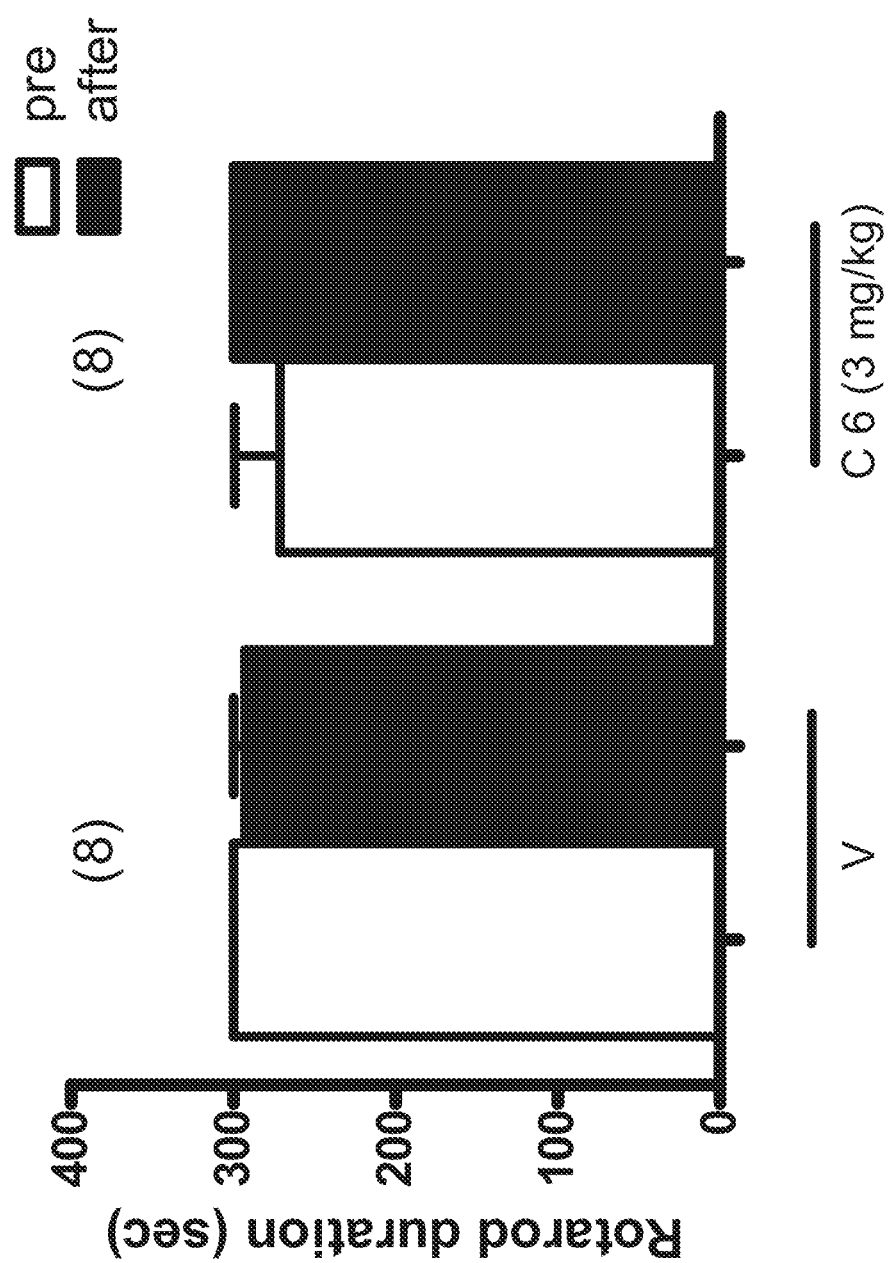
FIG. 10. Effect of Compound 6 on the performance of motor coordination in mice. Motor coordination was measured by the latency to fall in the rotarod test before before (pre) or 15 min after treatment with Compound 6 (C6, 3 mg/kg) and vehicle (V). The mouse was pre-trained until the latency to fall was greater than 120 sec.
Figure 11:
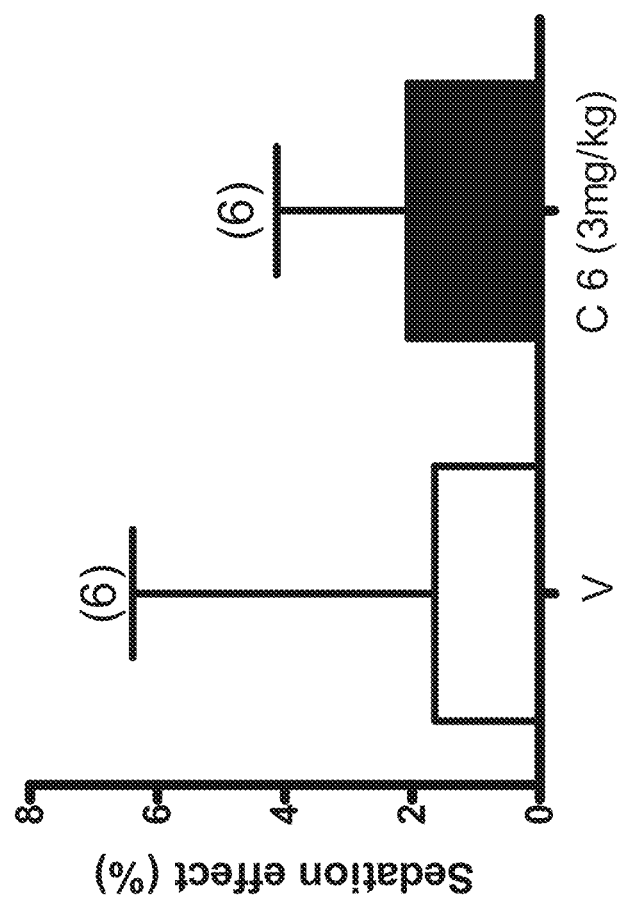
FIG. 11. Effect of Compound 6 on the performance of mice in a sedation assessment. The sedative effect was assessed by the latency for a mouse to step off from a 3 cm-high platform in a 60 sec-session with the formula: Sedation effect %=(Test latency−baseline latency)/(60−baseline latency)×100%. Compound 6 (C6, 3 mg/kg, i.p.) or vehicle (V) was given 10 min before the tests.
Figure 12:
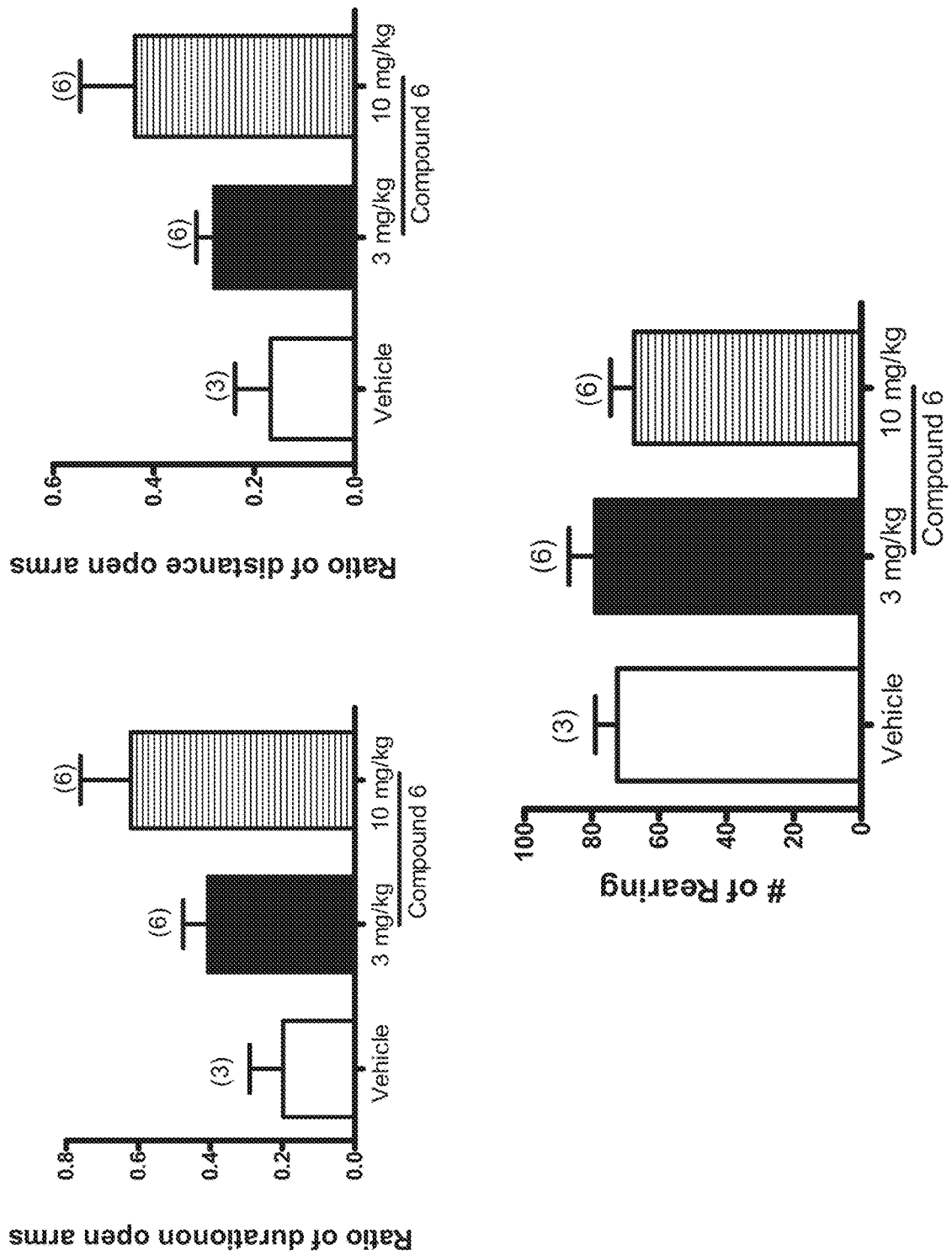
FIG. 12. Effects of Compound 6 on the performance of mice in the elevated plus maze (EPM) test, a measurement for its possible anxiolytic activity. It was assessed by the ratio of the duration (a) or entry distance (b) in open arms of the EPM apparatus. The rearing number of mice (c) in the EPM apparatus was also measured to evaluate their motor function. Compound 6 (3 mg/kg or 10 mg/kg i.p.) was given 10 min before the tests.

Intraperitoneal (i.p.) injection of Compound 6 significantly rescued methamphetamine-induced hyperlocomotion. This effect was significantly antagonized by intra-cerebellum microinjection of furosemide, a selective α6GABA$_A$R antagonist (FIG. 7). On the other hand, Compound 6 (i.p.) did not affect stereotypy climbing behaviors induced by apomorphine, a dopamine receptor agonist. (FIG. 8). However, Compound 6 did not affect the spontaneous motor activity (FIG. 7, the left paired bars), motor coordination in the rotarod test (FIG. 10), or the grip strength (FIG. 9), neither displayed any significant sedation (FIG. 11) or anxiolytic activity (FIG. 12) in the sedation assessment and elevated plus maze test, respectively. These results suggest that compound 6 can successfully pass through the blood brain barrier to rescue methamphetamine-induced hyperlocomotion possibly via enhancing cerebellar inhibitory control on the striatal dopaminergic activity through positively modulating a 6GABA$_A$Rs in cerebellar granule cells, but not affect dopamine receptor response directly. It is also suggested that the α6GABA$_A$R in the cerebellum is a new target for the treatment of TS or tic disorders. The PAM selective to α6GABA$_A$Rs may be a novel class of anti-tic therapy.

Example 12

Figure 13:
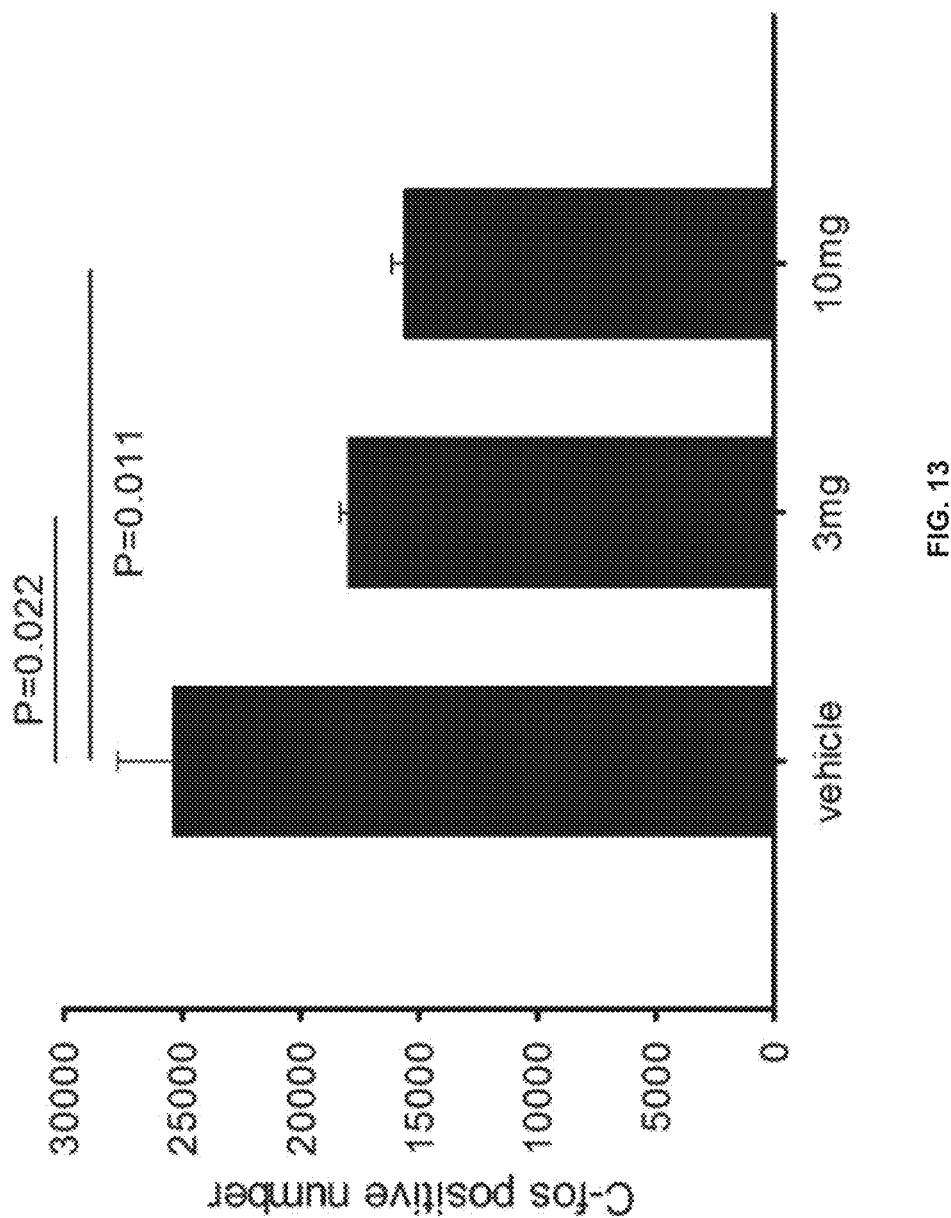
FIG. 13. Compound 6 reduces the number of capsaicin-increased c-fos ir cells in the trigeminal nucleus caudalis. Rats were given i.p. injection of 3 or 10 mg/kg of Compound 6 or its vehicle. The capsaicin (10 nmol, 100 μL) was injected by intracisterna injection. Two hours after capsicine injection, the total number of c-Fos-ir TCC neurons in three groups were estimated based on the formular derived in our previous study (Fan et al., 2012): 16(N1+N2)/2+53(N2+N3)/2, where N1, N2, and N3 were the c-Fos-ir neuronal numbers measured at the level of 0.6, −1.2, and −9 mm from the obex, respectively. Data are mean mean+SE. (One way ANOVA with Tukey posthoc test), n=2 in the vehicle group and n=3 in 10 and 30 mg/kg treated groups, respectively.

The Effect of Compound 6 on i.c. Capsaicin-Induced TNC Neuronal Activation, an Animal Model Mimicking Migraine FIG. 13 shows that Compound 6 when given by i.p. injection at 10 and 30 mg/kg significantly decreased the number of c-Fos-ir neurons in the TNC, a measurement of the number of activated TNC neurons, induced by i.c. capsaicin. This suggests that systemic administration of Compound 6 reduces TNC neuronal activation and has the potential for migraine treatment.

Example 13

Microsomal Stability Assay

4 µL of 1 mM test compound at a final concentration of 10 µM dissolved in DMSO/ACN/Methanol/Ethanol was preincubated at 37° C. for 5 minutes on a digital heating shaking dry bath (Fischer scientific, Pittsburgh, Pa.) in a mixture containing 282 µL of water, 80 µL of phosphate buffer (0.5 M, pH 7.4), 20 µL of NADPH Regenerating System Solution A (BD Bioscience, San Jose, Calif.) and 4 µL of NADPH Regenerating System Solution B (BD Bioscience, San Jose, Calif.) in a total volume of 391.2 µL. Following preincubation, the reaction was initiated by addition of 8.8 µL of either human liver microsomes (BD Gentest, San Jose, Calif.), mouse liver microsomes (Life technologies, Rockford, Ill.), at a protein concentration of 0.5 mg/mL. Aliquots of 50 µL were taken at time intervals of 0 (without microsomes), 10, 20, 30, 40, 50 and 60 minutes. Each aliquot was added to 100 µL of cold acetonitrile solution containing 1 µM/2 µM internal standard. This was followed by sonication for 10 seconds and centrifugation at 10,000 rpm for 5 minutes. 100 µL of the supernatant was transferred into Spin-X HPLC filter tubes (Corning Incorporated, NY) and centrifuged at 13,000 rpm for 5 minutes. The filtrate was diluted 100 fold and subsequently analyzed by LC-MS/MS with Shimadzu LCMS 8040, (Shimadzu Scientific Instruments, Columbia, Md.). The ratio of the peak areas of the internal standard and test compound was calculated for every time point and the natural log of the ratio were plotted against time to determine the linearslope (k). Themetabolicrate (k*$C_0$/C), half-life (0.693/k), and internal clearance (V*k) were calculated, where k is the slope, $C_0$ is the initial concentration of test compound, Cis the concentration of microsomes, and Vis the volume of incubation in µL per microsomal protein in mg. All experiments were repeated three times in duplicates. Results are shown in TABLE 2.

TABLE 2

Half-life of compounds.

| Compound | Half-life (min) (HLM) | % left after 1 hr. (HLM) | Half-life (min) (MLM) | % left after 1 hr. (MLM) |
| --- | --- | --- | --- | --- |
| DK-I-58-1 | 204.6 ± 10 | 81.5 ± 0.11 | 140 ± 7.18 | 73.8 ± 0.15 |
| LAU 463 | 104 ± 4 | 66.86 ± 0.13 | 113.17 ± 5.15 | 69 ± 0.16 |
| DK-I-59-1 | 649 ± 81 | 93 ± 0.09 | 165.74 ± 7.5 | 76.6 ± 0.11 |
| LAU 159 | 206.77 ± 15 | 81.44 ± 0.16 | 89.07 ± 5.22 | 59.83 ± 0.23 |
| DK-I-56-1 | 520 ± 51 | 91.69 ± 0.09 | 628.8 ± 73 | 92.8 ± 0.09 |
| Comp6 | 212.5 ± 25 | 86.1 ± 1.0 | 194.26 ± 11.41 | 80.35 ± 0.14 |
| DK-I-60-3 | 780.73 ± 238 | 91.51 ± 0.18 | 846.85 ± 276 | 93.08 ± 0.19 |
| RV-I-029 | 2972 ± 742 | 95.35 ± 1 | 857.8 ± 235 | 93.17 ± 016 |
| DK-I-93-1 | 640 ± 126 | 92.2 ± 0.15 | 263 ± 5.96 | 85.53 ± 0.07 |
| Comp 11 | 135.4 ± 5 | 72.5 ± 0.11 | 115.6 ± 5.2 | 69.2 ± 0.15 |
| DK-I-86-1 | 752.30 ± 261 | 92.3 ± 0.13 | 550.6 ± 78 | 91.3 ± 0.12 |
| DK-II-13-1 | 794 ± 182 | 93 ± 0.14 | 139.2 ± 5.8 | 74.77 ± 0.12 |
| DK-II-58-1 | 2341 ± 0.001 | 97.8 ± 0.06 | 4250 ± 0.001 | 98.39 ± 0.06 |
| DK-II-48-1 | 727.7 ± 115 | 93.4 ± 0.11 | 680.6 ± 14 | 93.12 ± 0.22 |
| DK-II-59-1 | 725.8 ± 146 | 93 ± 0.12 | 250.62 ± 13 | 85.1 ± 0.10 |
| DK-II-18-1 | 511 ± 44 | 91.6 ± 0.10 | 265 ± 17 | 85.6 ± 0.12 |
| DK-II-60-1 | 592.5 ± 96 | 92.5 ± 0.12 | 640 ± 102 | 92.4 ± 0.12 |
| DK-I-87-1 | 990 ± 159 | 94.7 ± 0.07 | 993 ± 189 | 94.91 ± 0.10 |

DK-I-58-1 and LAU 463 are bromine containing α6 analogs. The deuterated analog is more stable compared to methoxy compound which is nearly 15-20% less stable. The chlorine containing non-deuterated analog (LAU 159) is shown to be less stable indicated nearly 80% stability in Human and even lesser stability (~60%) in mouse microsomes compared to other compounds that have (—$OCH_3$) in the adjacent position without the chlorine and deuterated compound with the deuterium 15-20% more stable in both species and similar stability was observed with the DK-I-93-1 and Comp 11 analogs with the Deuterium containing analog having the higher stability.

The mono (RV-I-029 and DK-I-56-1) and di deuterated (DK-I-60-3) analogs of Comp 6 have shown a higher stability that is more than 90% compared to Comp 6 which is 86% stable in Human and 80% stable in Mouse liver microsomes respectively with significant variation in the mouse species.

DK-I-86-1 and DK-II-13-1 are the pyridine containing compounds. In comparison, the Deuterated (—$OCD_3$ containing DK-I-86-1) has significant higher in the stability (nearly 20%) compared to non-Deuterated (DK-II-13-1) in mouse liver microsomes, however they behave same in Human liver microsomes. The other pyridine containing analogs with the Bromine (DK-II-58-1 and DK-II-48-1) and Chlorine (DK-II-59-1 and DK-I-18-1) behave similarly in the both the species but they have shown significant variation from the corresponding compounds that do not contain the pyridine ring.

The DK-II-60-1 analog with the methoxy substitution in place of bromine in DK-II-58-1 behave similar to it and also DK-I-87-1 with the —$OCD_3$ at the ortho position compared to the DK-I-59-1 analog has significant variation in the stability in the mouse liver microsomes but not in the human species.

In conclusion, the deuterium containing analogs of Alpha 6 compounds have a significant variation and have shown higher stability compared to non-deuterated analogs.

Example 14

Alpha 6 Cytotoxicity Study

Reagents and Instrumentation: Human liver hepatocellular carcinoma (HEPG2) cell line was purchased (ATCC) and cultured in 75 cm2 flasks (CellStar). Cells were grown in DMEM/High Glucose (Hyclone, #SH3024301) media to which non-essential amino acids (Hyclone, #SH30238.01), 10 mM HEPES (Hyclone, #SH302237.01), 5×106 units of penicillin and streptomycin (Hyclone, #SV30010), and 10% of heat inactivated fetal bovine serum (Gibco, #10082147) were added. Cells were harvested using 0.05% Trypsin (Hyclone, #SH3023601), which disrupts the cell monolayer and proteolytically cleaves the bonds between the cells and flask. The cell viability assay was evaluated using CellTiter-Glo™ Luminescent Cell Viability Assay Kit (Promega, Madison, Wis.) which contains luciferase and all its substrate except ATP. The controls for the cytotoxicity assay used were (E)-10-(bromotriphenylphosphoranyl)decyl 4-(4-(tert-butyl)phenyl)-4-oxobut-2-enoate (400 µM in DMSO, positive control) and DMSO (negative control). Cell culture was performed in a Baker Company Class II Biological Safety Cabinet. All luminescence readings were performed on a Tecan Infinite M1000 plate reader. Small volume transfers were performed on the Tecan Freedom EVO liquid handling system with a 100 nL pin tool transfer (V&P Scientific). Serial dilutions were done in 96-well polypropylene plates (Corning, #3365) and assays were conducted in 384-well white optical bottom plates.

Luminescence-Based VDR-Mediated Transcription Assay Protocol: After 48 hours of incubation at 37° C. with 5% CO2, the cells were harvested with 4 mL of 0.05% Trypsin, added to 10 mL of the assay buffer, DMEM/High Modified buffer without phenol red, and spun down for 3 minutes at 1000 rpm. The media was removed and cells were resuspended in the DMEM assay media. To each well, 40 µL of cells were added to yield a final concentration of 15,000 cells per well. The plates were then spun down for 2 minutes at 1000 rpm. After 2 hours, plated cells were treated with 100 nL×4 of small molecules and controls which were added using the pin tool. After 48 hours of incubation at 37° C. with 5% CO2, 20 µL of Cell Titer-Glo™ Luminescence Assay Kit (cytotoxicity assay) were added and luminescence was read. Controls were measured within each plate to determine the z' factor (Equation 1) and to enable data normalization. Three independent experiments were performed in quadruplicate and data was analyzed using non-linear regression with variable slope (GraphPrism, Equation 2). The luminescence intensity of control (untreated) cells was taken as 100% viability, and the relative cell viability compared to control was calculated. Data are presented as the means±SEM of a series of three experiments.

$$Z' = 1 - \left( \frac{3 \times (\text{Standard Deviation Positive} + \text{Standard Deviation Negative})}{|\text{Average Positive} - \text{Average Negative}|} \right) \quad \text{Equation 1}$$

$$\frac{\text{Bottom} + (\text{top} - \text{bottom})}{(1 + 10^{(logIC50 - X)(HillSlope)})} \quad \text{Equation 2}$$

Figure 19:
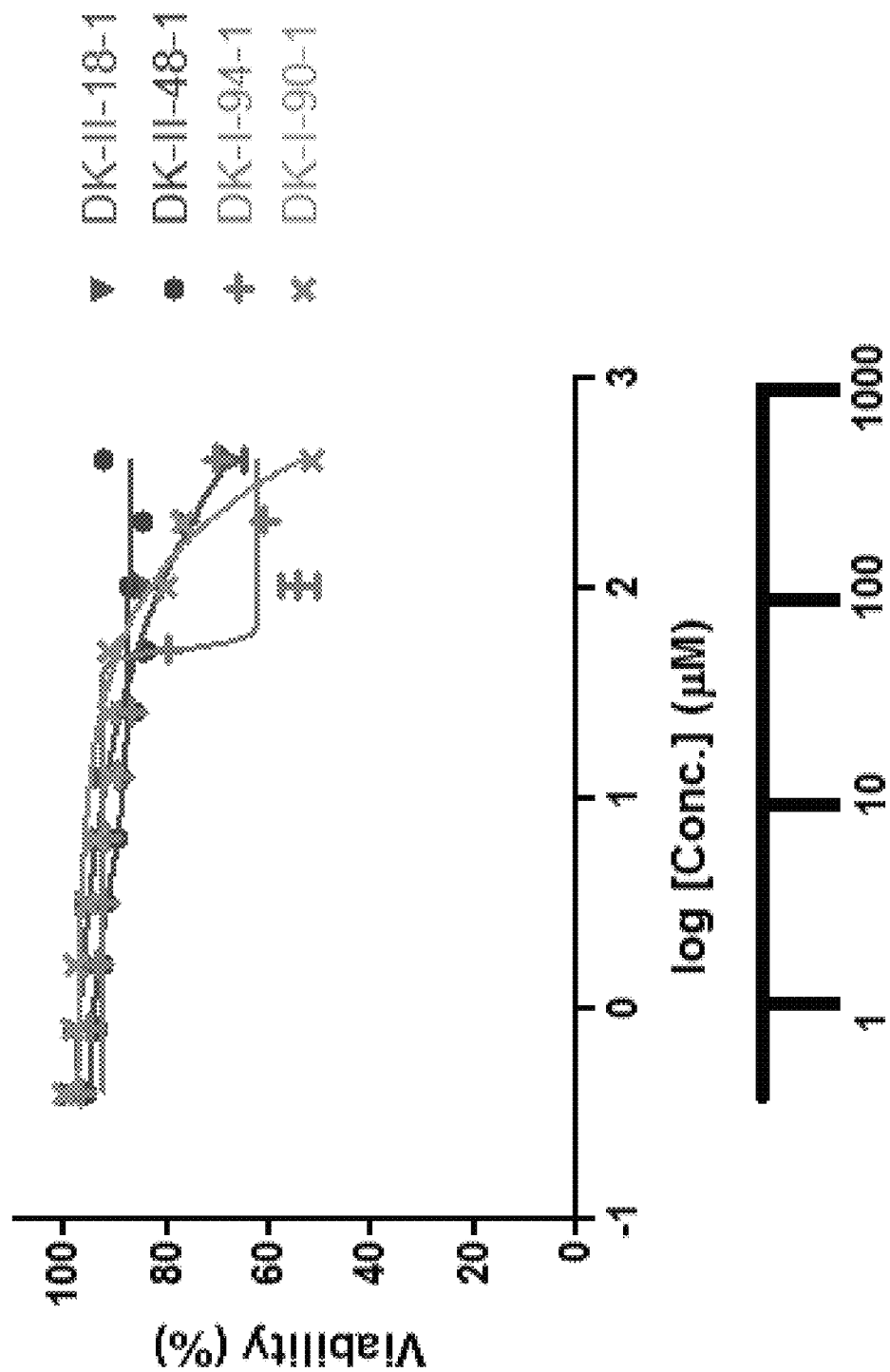
FIG. 19 is a graph of viability versus log[concentration] for cytotoxic analysis for various compounds.

Results are shown in TABLE 3, FIG. 17, FIG. 18, and FIG. 19. The compounds such as DK-I-58-1, DK-I-59-1, DK-I-56-1, DK-I-60-3, DK-I-86-1, and DK-II-48-1 are non-toxic even at 400 µM. The compounds RV-I-029, DK-I-93-1, DK-I-87-1, DK-I-94-1, DK-II-18-1, and DK-I-90-1 are moderately toxic and their LD50 values are more than 200 µM.

TABLE 3

Cytotoxicity study results for HEPG2 cell lines.

| S. No. | Non-toxic at 400 µM | LD$_{50}$ values higher than 200 µM |
|---|---|---|
| 1 | DK-I-58-1 | RV-I-029 |
| 2 | DK-I-59-1 | DK-I-93-1 |
| 3 | DK-I-56-1 | DK-I-87-1 |
| 4 | DK-I-60-3 | DK-I-94-1 |
| 5 | DK-I-86-1 | DK-II-18-1 |
| 6 | DK-II-48-1 | DK-I-90-1 |

Example 15

Rotorod Assay

Figure 20:
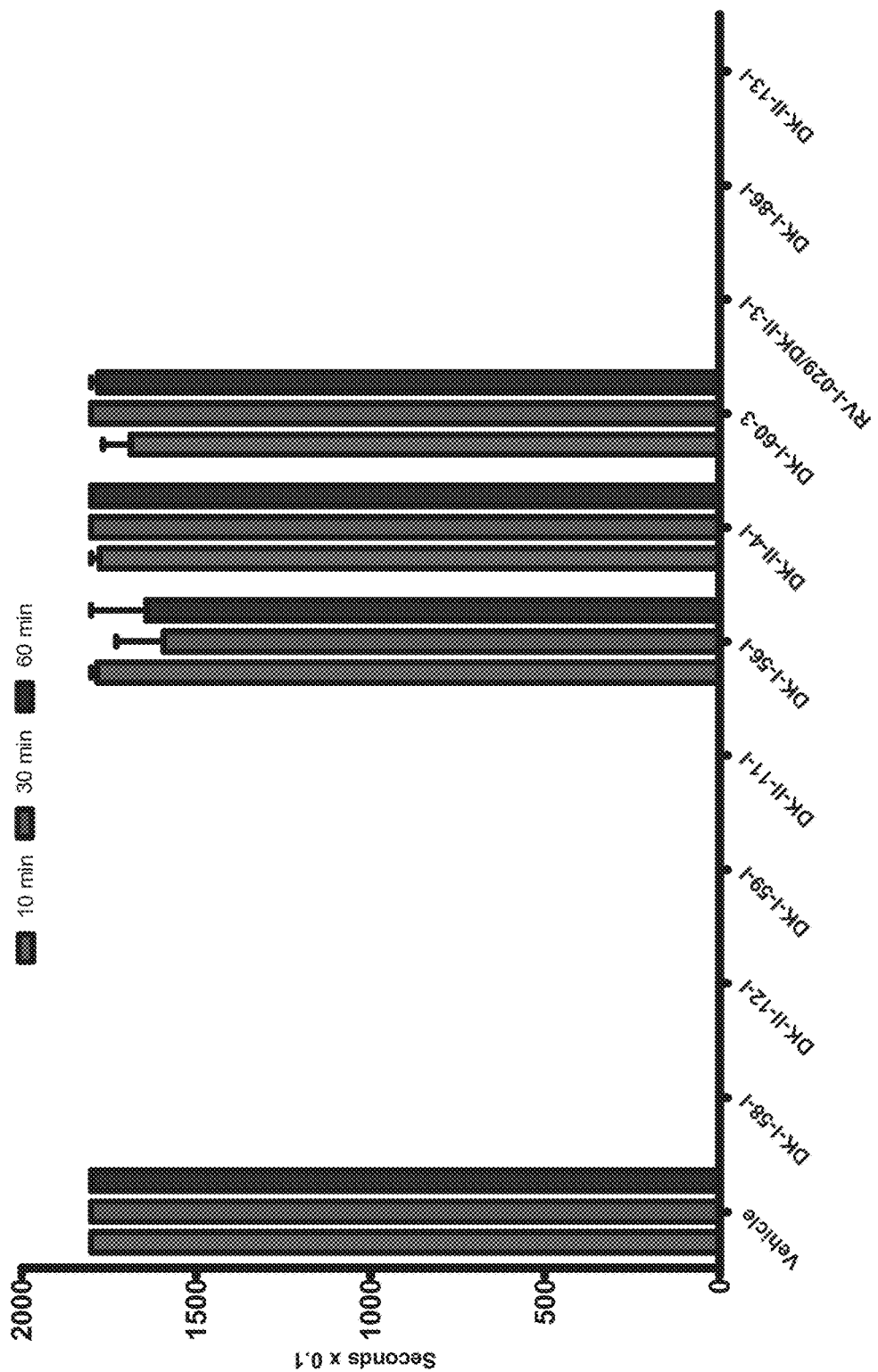
FIG. 20 is a graph of the time mice performed in the rotorod assay.

30 White female Swiss Webster mice were trained to maintain balance at a constant speed of 15 rpm on the rotarod apparatus (Omnitech Electronics Inc., Nova Scotia, Canada) until mice could perform for three minutes at three consecutive time points. Separate groups of mice received intraperitoneal (i.p.) injections of vehicle (40% soybean oil, 10% water, 15% kolliphor, and 35% glycerol), α6 test compounds (1, 5, 20, or 40 mg/kg), and diazepam as a positive control compound (1 mg/kg or 5 mg/kg) in an approximate volume of 100 µL. Ten minutes after each injection, mice were placed on the rotarod for three minutes. A fail was assigned for each mouse that fell from the rotarod prior to 3 minutes. Mice were rested two to three days before administration of another dose or a different compound. The protocol was changed to a 200 µL i.p. injection for vehicle and compounds due to solubility. Results are shown in FIG. 20.

Example 16

Tinnitus Experiment

About 96 rats (Sprague Dawley, 8 weeks old, b.w. 250 to 300 gm) will be used. Animals are randomly divided into 2 groups: (a) group A, loud sound-treated and (b) group B, control. Each group will be housed in a laboratory room. Two groups will be further divided into 3 subgroups to each receive (a) sound treated and additional injection of vehicle (20% DMSO+20% Cremophor® EL+60% saline, Sigma) (b) an additional injection of Compound 6 (@3 mg/kg), and (c) DK-I-56-1 (@ 3 mg/kg).

Half animals (n=48) will be used for assessed by combined studies of Fos-immunoreactivities and tinnitus behavioral test and the rest animal will be used for electrophysiological studies. Animals for electrophysiological measurement will first undergo aseptic surgery under general anesthesia (isoflurane) before the sound or sham treatment.

Loud sound exposure. The narrow band noise with the center frequency at 10 kHz will be chosen since the 10 kHz is the most sensitive frequency of the rat audiogram (Kelly and Mastron, 1977). Sound will be presented to animals through a free-field speaker (TDT, FF1) placed at the ceiling of the sound-treated chamber (W×D×H=60×60 cm×60 cm$^3$). An intensity level of 120 dB SPL will be chosen and confirmed by the measurement with a calibration microphone (B&K 4149) placed at the position of animals. The head will be positioned approximately 40 cm below the center of the speaker. The loud noise will be delivered to the animals for 2 hr. Rats in group A will be anesthetized with 3% isoflurane during the sound exposure. Rats in group B will be anesthetized and put in the sound treated room without sound exposure for 2 hrs.

After the acoustic manipulation, animals will be returned to normal rearing cages and environment until the subsequent experiment.

Surgery for chronic electrode implantation. For the implantation of the dorsal cochlear nucleus and auditory cortex (AC) recording electrode, twos hole (size ~2 mm) will be made between bregma −10.80 to −11.76 and −3.3- to −6.3 mm for access to the DCN and AC respectively. The active recording electrodes were made by Teflon-coated tungsten (A-M Systems, 0.013" OD) Teflon-coated silver (with tip made into a disk shape, A-M Systems, 0.013" OD) wires, will be inserted into DCN and placed on the surface AC. The reference electrodes will be implanted through an opening in the frontal skull. All wires will be connected to a miniature connector and fixed by Histoacryl and reinforced with dental cement (GC Fuji Plus, Tokyo). The resected skin will be closed with fine suture (6/0). Wounds will be checked for possible infections on a daily basis and treated topically with antibiotic (chloramphenicol, 30 mg/kg, once to twice daily when necessary).

Electrophysiological recordings. From 8 to 6 days before loud sound exposed or sham control treatment, all animals, with the recording wires connected will be preconditioned inside a behaving chamber (4 hrs/day) for preconditioning. Then, the control measurements of auditory activities will be made for 5 continuous days (4 hours/day: 1 hr in silence, 3 hrs for auditory threshold measurement). Both the spontaneous and sound evoked activities will be recorded from the AC. The effects of loud sound exposure on AC activities will be will be measured for 7 continuous days (4 hours/day: 1 hr in silence, 3 hrs for auditory threshold measurement). Rats receiving (a) the vehicle, (b) Compound 6 and (c) DK-I-56-1, measurements of spontaneous and sound evoked activities will be again made in sessions each lasting for 6 hrs (2 hrs before to 4 hrs after the drug treatment).

During recording sessions, the miniature connector plug is connected to a chronic head stage (RA16CH, TDT), and fed to a 32-bit neurophysiology base station (RZ5, TDT) that was controlled by an OpenEx software suite (TDT). Signals will be amplified, band-pass filtered (1-3000 Hz), monitored in real time and digitized at 12 kHz, 16-bit resolutions for data storage. FIG. 2 shows the procedures of electrophysiological recordings from the AC of behaving rats.

Acoustic stimuli. Tone bursts (25-msec duration, 2.5 msec rise/fall time) will be delivered through a free-field speaker (Fostex, FE103E) located at the ceiling of a sound-treated room where the animal is housed. Tone bursts have a frequency chosen from a user menu (1, 2, 4, 10, or 16 kHz). Sound intensity will be randomized for presentation within an intensity range (5 to 75 dB SPL, 5 dB steps). The intensity will be calibrated at the site of animal from 0.5 to 30 kHz using a precision microphone system (B&K 5113). Response to each tone presentation will be collected on a single-trial basis for a duration of 1 sec (400 msec before, 600 msec after stimulus onset). The inter trial interval will be 2 sec. A total of 80-100 trials will be collected during a session at a fixed frequency and intensity. The silence sessions will be similarly conducted without the sound stimulation.

Data analysis. Single trials will be first processed by the event-related analysis in the time and spectral domains. For time domain analysis, the average evoked responses will be computed across repeated trials. The response-level function will be generated based on the evoked potential integrals obtained from two time windows (0-5 ms and 15-200 msec).

Activates recorded from the AC will be also analyzed in spectral domain. The total power spectrum and the event related spectral perturbation (ERSP; Makeig, 1993) will be computed to reveal the spontaneous activities and time-locked (but not necessary phase-lock) responses to sound. For the ERSP analysis, the baseline spectrum preceding the stimulus onset will be canceled from the post-stimulus response spectrum to suppress frequency components that are not related to the stimulus sound. Specifically, short time fast Fourier transforms (FFT) will be applied systematically with a running window (256 sample points, 244 points in overlap). In the final step, non-significant parts of ERSP are truncated to zero values through a procedure of bootstrapping. The single trial will be first divided into 200 segments each of 512-point long. Each segment will be convolved with a Hanning window and then zero padded to 1024 points for spectral estimation with FFT. Log power spectra will be computed and normalized against the baseline (straight tunnel segment) log mean power spectra. The time series of each trial will be entered into a time-frequency matrix (1000×2014), with a frequency resolution of 0.05 Hz. Results will be averaged across repeated trials to yield a standard image of ERSP. Significant levels of deviations from pre-stimulus baseline will be assessed by bootstrapping (a nonparametric permutation-based statistical method). Non-significant points will be masked to zero to better reveal the perturbations with significance ($p<0.05$). The inter-trial coherence will be further determined to reflect neural synchrony. To characterize changes in spontaneous activities, the activities collected in the silence sessions will be analyzed in the spectral domain (total spectrum) by FFT. The magnitude of individual frequency components (0-3,000 Hz) will be presented in dB scale. To reveal tinnitus-related changes in the resting state, the power spectra of the SS treatment will be normalized against the control power spectra.

Statistical Analysis. Since the power spectra of silence and sound evoked sessions are not normally distributed, nonparametric statistic tests are used for their analysis. Friedman's test (Matlab statistical toolbox, Mathworks) is used to evaluate the effects of tinnitus percept or sound intensity on EPs. Bootstrapping (EEGLAB toolbox, UCSD) will be used for assessing statistical significance of power changes. To test group statistics, the intrinsic inter-animal EP difference will be reduced by dividing the grand mean of the silence trials (or averaged responses) within the first 200 msec of each trial. The significant level is set at $p<0.05$.

Histological confirmation of cortical recording sites. On day following the end of recording, animals will be euthanized (Nembutal 75 mg/kg) and perfused with 0.9% saline solution followed by 4% paraformaldehyde (Merck), with the removed brains post-fixed overnight, cryoprotected in 30% sucrose, 0.1 M phosphate buffered saline (PBS) solution. Brains will be sectioned (40 μm) with a freezing microtome in the coronal plane, and placed into 0.1 M PBS for later histology. Sections will be mounted on slides, air-dried, mounting with Vectashield medium (Vector Laboratories). To check the electrode positions, low magnifications (×40) images will be digitized (Canon E50) through a microscope (Olympus BX51). The location of electrode will be checked with the Di-I stain together with the location of AC determined by landmarks referenced to the rat brain atlas.

Behavioral test. The paradigm is modified from the Berger et al (2013). The background noise of gap detection will comprise with narrow-band noise (2 kHz bandwidth) with center frequencies varied at 4, 8 and 16 kHz. Evoked stimuli will be short broad-band noise bursts (20 ms; rise/fall time of 1 ms). A single session will consist of 5 presentations of the stimulus preceded by a silence gap, and 5 presentations without a silence gap randomly delivered in a given background noise condition. To avoid habituation, the inter stimulus interval (ISI) will be around 10 min, leading to a single trial taking around 1.5-2 hr. Gap duration of 100 ms (rise/fall time of 2 ms) and a delay of 100 ms between the gap onset and the startle stimulus onset will be used. The background noise will be randomly varied from 5 to 25 dB SPL (5 dB/step) and the evoked stimulus will be presented at either 10 dB SPL louder than the background. The pinna reflex will be measured with a high-resolution video camera system (Image Solution Group model LW-1.3-S-1394-M) and data will be analyzed off-line using custom-made software we developed on movement detection (details see Wu et al., 2000). The baseline of pinna reflex and Gap pre-pulse inhibition will be measured in each animal (at least 6 sessions over a week) before the sound exposure. Effects of mild sound exposure on pinna reflex and Gap pre-pulse inhibition will be subsequently measured at 1-2 weeks after the termination of sound exposure. After finishing the behavioral assessments, animals will be sacrificed and their brains will be processed with Fos-immuno-histochemical studies.

Fos Immuno-histochemical staining. One day after finished the behavioral assessment, the experimental and control rats will be preconditioning inside the sound treated room for 8 hrs. Then, animals will be sacrificed with overdose urethane (2.0 g/kg) and perfused via an intra-aortic catheter (with physiological saline PBS; pH 7.2, followed by 4% para-formaldehyde solution). The removed brains will be cryoprotected overnight in a sucrose-buffer (30% in PBS). Frozen sections (40 m) will be cut in coronal plane and alternated sections incubated in solutions as listed below, interspersed PBS rinses: (a) normal goat serum at a dilution of 1:100 (Vector) for 2 hrs; (b) Fos antibody (1:4000, Santa Cruz) in PBS for 48 hrs at 4° C.; (b) PBS wash 3×5 min; (c) biotinylated anti-rabbit IgG or biotinylated anti-mouse IgG (Vector) at 1:500 in PBS with 1% normal goat serum, incubated for 3 hrs; (d) rinsed with PBS 3×5 min; (e) incubated with ABC Kit reagent (Vector) for 2 hrs; (f) rinsed with PBS 3×5 min; (g) 3× rinses with acetate buffer (0.1M, pH=6.0); (h) developed with nickel-DAB-glucose oxidase solution for 5-10 min; (I) 2× rinses in acetate buffer for 5 min. The sections will be mounted on the slide for the microscopic analysis.

All sections will be analyzed using light microscopy. Digital photomicrographs will be taken using a digital camera (Canon E50) mounted on an Olympus microscope (BX 51). Pictures will be digitally adjusted for color, brightness, or contrast at the time that the photograph was taken, but no further digital adjustments will be made to the photograph of the tissue. High magnification (100×) composite images will be created by compiling photographic stacks using Image Pro Plus software (Media Cybernetics, Silver Spring, Md., USA). Locations of labeled cells will be manually digitized (SummaSketch III, Xu et al., 1990) and reconstructed with software specially developed to visualize their 3D patterns of distribution (Wu et al., 2003). This approach will allow the examination of all labeled neurons along the auditory relays from CN to AC.

The role of α6GABA$_A$Rs in depression. Finally, in the meantime evidence accumulated indicating that α6-GABA$_A$ receptors are widely distributed throughout the brain, although with a much lower concentration than that found in the granule cells of cerebellum (Allen brain atlas). It can be assumed that low abundance receptors exhibit quite specific and important functions in the brain by modulating only those neurons on which they are located.

Since linkage studies indicate that the gene for α6-subunits is associated with female patients with mood disorders (Yamada et al., 2003), α6-containing receptors might also have some beneficial effects in mood disorders such as depression. Experiments are underway investigating whether compounds in this patent application are able to ameliorate symptoms of depression in several animal models of depression.

The invention claimed is:

1. A deuterium enriched compound

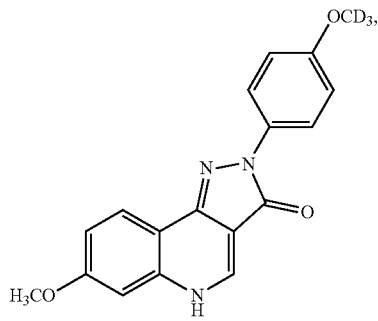

wherein the —OCD$_3$ is deuterium enriched.

2. A pharmaceutical composition comprising the compound of claim 1 and a pharmaceutically acceptable carrier.

* * * * *